(12) United States Patent
Long et al.

(10) Patent No.: US 10,517,742 B2
(45) Date of Patent: Dec. 31, 2019

(54) PUNCH, IMPLANT AND ASSOCIATED METHOD

(71) Applicant: DePuy Synthes Products, Inc., Raynham, MA (US)

(72) Inventors: Jack F. Long, Warsaw, IN (US); Joseph P. Iannotti, Cleveland, OH (US); Gerald R. Williams, Philadelphia, PA (US)

(73) Assignee: DePuy Synthes Products, Inc., Rayham, MA (US)

( * ) Notice: Subject to any disclaimer, the term of this patent is extended or adjusted under 35 U.S.C. 154(b) by 0 days.

(21) Appl. No.: 15/835,913

(22) Filed: Dec. 8, 2017

(65) Prior Publication Data

US 2018/0104073 A1    Apr. 19, 2018

Related U.S. Application Data

(60) Division of application No. 13/361,517, filed on Jan. 30, 2012, now Pat. No. 9,849,000, which is a division
(Continued)

(51) Int. Cl.
*A61B 17/16* (2006.01)
*A61F 2/46* (2006.01)
(Continued)

(52) U.S. Cl.
CPC ........ *A61F 2/4684* (2013.01); *A61B 17/1604* (2013.01); *A61B 17/1684* (2013.01);
(Continued)

(58) Field of Classification Search
CPC ............ A61B 17/1604; A61B 17/1742; A61B 17/175
See application file for complete search history.

(56) References Cited

U.S. PATENT DOCUMENTS

| 788,362 A | 4/1905 | Lavery |
| 1,023,542 A | 4/1912 | Winter |

(Continued)

FOREIGN PATENT DOCUMENTS

| DE | 2041929 | 3/1971 |
| DE | 4228710 A1 | 3/1993 |

(Continued)

OTHER PUBLICATIONS

European Search Report in corresponding European application (i.e., EP 10 18 7319), dated Jan. 13, 2011, 8 pages.
(Continued)

*Primary Examiner* — Christopher D. Prone
*Assistant Examiner* — Christine L Nelson
(74) *Attorney, Agent, or Firm* — Maginot, Moore & Beck, LLP

(57) ABSTRACT

A method of performing joint arthroplasty includes preparing a flat surface on a long bone, providing an instrument having a body and a punch extending from the body, the punch including a portion thereof having a shape similar to a stem of an implant, positioning a stop on the flat surface, rotating the stop with respect to the surface of the long bone based upon an indicia on one of the body and the stop so as to position the punch rotationally with respect to the surface to a desired orientation when the instrument is at least partially inserted into the stop, using the instrument to form a cavity in the long bone with the punch at the desired rotational orientation with the instrument inserted at least partially within the stop, the cavity having a shape similar to the stem of the implant, and implanting the stem into the cavity.

18 Claims, 44 Drawing Sheets

Related U.S. Application Data of application No. 10/794,628, filed on Mar. 5, 2004, now Pat. No. 8,105,327, which is a continuation-in-part of application No. 10/403,364, filed on Mar. 31, 2003, now Pat. No. 7,338,498.

(51) Int. Cl.
| | | |
|---|---|---|
| *A61F 2/36* | (2006.01) | |
| *A61F 2/40* | (2006.01) | |
| *A61B 17/17* | (2006.01) | |
| A61B 17/00 | (2006.01) | |
| A61F 2/28 | (2006.01) | |
| A61F 2/30 | (2006.01) | |
| A61B 90/00 | (2016.01) | |

(52) U.S. Cl.
CPC ........ *A61B 17/1778* (2016.11); *A61F 2/3603* (2013.01); *A61F 2/4003* (2013.01); *A61F 2/4612* (2013.01); A61B 2017/00469 (2013.01); A61B 2090/033 (2016.02); A61F 2/3601 (2013.01); A61F 2/4607 (2013.01); A61F 2002/2835 (2013.01); A61F 2002/30163 (2013.01); A61F 2002/30245 (2013.01); A61F 2002/30299 (2013.01); A61F 2002/30616 (2013.01); A61F 2002/30841 (2013.01); A61F 2002/30878 (2013.01); A61F 2002/30884 (2013.01); A61F 2002/4007 (2013.01); A61F 2002/4623 (2013.01); A61F 2002/4677 (2013.01); A61F 2002/4681 (2013.01); A61F 2230/0028 (2013.01); A61F 2230/0071 (2013.01); A61F 2230/0093 (2013.01)

(56) References Cited

U.S. PATENT DOCUMENTS

| | | | |
|---|---|---|---|
| 1,345,443 A | 7/1920 | Hood | |
| 1,669,701 A | 5/1928 | Estwing | |
| 2,200,120 A | 5/1940 | Nauth | |
| 2,222,517 A | 11/1940 | Price | |
| 2,243,718 A | 5/1941 | De G. Moreira | |
| 2,718,228 A | 9/1955 | Van Steenbrugghe | |
| 2,725,878 A | 12/1955 | Reiter | |
| 2,804,895 A | 9/1957 | Clement | |
| 2,934,065 A | 4/1960 | Townley | |
| 3,002,514 A | 10/1961 | Deyerle | |
| 3,605,527 A | 9/1971 | Gambale | |
| 3,702,611 A | 11/1972 | Fishbein | |
| 3,840,904 A | 10/1974 | Tronzo | |
| 3,855,638 A | 12/1974 | Pilliar | |
| 3,979,778 A | 9/1976 | Stroot | |
| 4,042,980 A | 8/1977 | Swanson et al. | |
| 4,206,517 A | 6/1980 | Pappas et al. | |
| 4,271,849 A | 6/1981 | Rehder | |
| 4,274,164 A | 6/1981 | Rehder et al. | |
| 4,328,593 A | 5/1982 | Sutter et al. | |
| 4,332,036 A | 6/1982 | Sutter et al. | |
| 4,335,429 A | 6/1982 | Kawakatsu | |
| 4,355,429 A | 10/1982 | Mittelmeier et al. | |
| 4,432,358 A | 2/1984 | Fixel | |
| 4,441,492 A | 4/1984 | Rydell et al. | |
| 4,502,474 A | 3/1985 | Comparetto | |
| 4,550,450 A | 11/1985 | Kinnett | |
| 4,601,289 A | 7/1986 | Chiarizzio et al. | |
| 4,714,471 A | 12/1987 | Grundei | |
| 4,722,330 A | 2/1988 | Russell et al. | |
| 4,752,296 A | 6/1988 | Buechel et al. | |
| 4,787,378 A * | 11/1988 | Sodhi .................. | A61B 17/742 606/67 |
| 4,795,473 A | 1/1989 | Grimes | |
| 4,801,289 A | 1/1989 | Sugimoto et al. | |
| 4,805,607 A | 2/1989 | Engelhardt et al. | |
| 4,846,841 A | 7/1989 | Oh | |
| 4,865,605 A | 9/1989 | Dines et al. | |
| 4,865,609 A | 9/1989 | Roche | |
| 4,893,619 A | 1/1990 | Dale et al. | |
| 4,919,669 A | 4/1990 | Lannelongue | |
| 4,987,904 A | 1/1991 | Wilson | |
| 4,995,883 A | 2/1991 | Demane et al. | |
| 5,041,117 A | 8/1991 | Engelhardt | |
| 5,064,427 A | 11/1991 | Burkinshaw | |
| 5,070,623 A | 12/1991 | Barnes | |
| 5,108,396 A | 4/1992 | Lackey et al. | |
| 5,116,339 A | 5/1992 | Glock | |
| 5,141,520 A | 8/1992 | Goble et al. | |
| 5,226,915 A | 7/1993 | Bertin | |
| 5,250,051 A | 10/1993 | Maryan | |
| 5,258,033 A | 11/1993 | Lawes et al. | |
| 5,282,865 A | 2/1994 | Dong | |
| 5,282,866 A | 2/1994 | Cohen et al. | |
| 5,312,411 A | 5/1994 | Steele et al. | |
| 5,314,479 A | 5/1994 | Rockwood, Jr. et al. | |
| 5,358,525 A | 10/1994 | Fox et al. | |
| 5,374,269 A | 12/1994 | Rosenberg | |
| 5,405,349 A | 4/1995 | Burkinshaw et al. | |
| 5,423,827 A | 6/1995 | Mumme et al. | |
| 5,454,816 A | 10/1995 | Ashby | |
| 5,470,336 A | 11/1995 | Ling et al. | |
| 5,476,467 A | 12/1995 | Benoist | |
| 5,486,178 A | 1/1996 | Hodge | |
| 5,490,852 A | 2/1996 | Azer et al. | |
| 5,507,817 A | 4/1996 | Craig et al. | |
| 5,514,139 A | 5/1996 | Goldstein et al. | |
| 5,540,696 A | 7/1996 | Booth, Jr. et al. | |
| 5,549,704 A | 8/1996 | Sutter | |
| 5,569,263 A | 10/1996 | Hein | |
| 5,662,476 A | 9/1997 | Ingber et al. | |
| 5,683,395 A | 11/1997 | Mikhail | |
| 5,690,636 A | 11/1997 | Wildgoose et al. | |
| 5,702,460 A | 12/1997 | Carls et al. | |
| 5,723,018 A | 3/1998 | Cyprien et al. | |
| 5,735,905 A | 4/1998 | Parr | |
| 5,769,852 A | 6/1998 | Branemark | |
| 5,776,194 A | 7/1998 | Mikol et al. | |
| 5,776,201 A | 7/1998 | Colleran et al. | |
| 5,779,710 A | 7/1998 | Matsen, III | |
| 5,800,437 A | 9/1998 | Gustilo et al. | |
| 5,800,557 A | 9/1998 | Elhami | |
| 5,830,216 A | 11/1998 | Insall et al. | |
| 5,893,850 A | 4/1999 | Cachia | |
| 5,957,926 A | 9/1999 | Masini | |
| 6,013,104 A | 1/2000 | Kampner | |
| 6,045,582 A | 4/2000 | Prybyla | |
| 6,063,124 A | 5/2000 | Amstutz | |
| 6,071,311 A | 6/2000 | O'Neil et al. | |
| 6,093,124 A | 7/2000 | Eyley | |
| 6,102,916 A | 8/2000 | Masini | |
| 6,110,200 A | 8/2000 | Hinnenkamp | |
| 6,127,596 A | 10/2000 | Brown et al. | |
| 6,129,764 A | 10/2000 | Servidio | |
| 6,132,469 A | 10/2000 | Schroeder | |
| 6,156,069 A | 12/2000 | Amstutz | |
| 6,168,628 B1 | 1/2001 | Huebner | |
| 6,187,012 B1 | 2/2001 | Masini | |
| 6,190,390 B1 | 2/2001 | McAllister | |
| 6,200,319 B1 | 3/2001 | Storer et al. | |
| 6,206,884 B1 | 3/2001 | Masini | |
| 6,283,999 B1 | 9/2001 | Rockwood, Jr. | |
| 6,319,104 B1 | 11/2001 | Emter | |
| 6,334,874 B1 | 1/2002 | Tornier et al. | |
| 6,355,045 B1 * | 3/2002 | Gundlapalli ....... | A61B 17/1764 606/86 R |
| 6,364,910 B1 | 4/2002 | Shultz et al. | |
| 6,368,353 B1 | 4/2002 | Arcand | |
| 6,508,840 B1 | 1/2003 | Rockwood, Jr. et al. | |
| 6,508,841 B2 | 1/2003 | Martin et al. | |
| 6,554,865 B2 | 4/2003 | Grusin et al. | |
| 6,620,197 B2 | 9/2003 | Maroney et al. | |
| 6,709,439 B2 | 3/2004 | Rogers et al. | |
| 6,740,120 B1 | 5/2004 | Grimes | |
| 6,755,865 B2 | 6/2004 | Tarabishy | |
| 6,783,549 B1 | 8/2004 | Stone et al. | |

(56) References Cited

U.S. PATENT DOCUMENTS

| | | |
|---|---|---|
| 6,875,222 B2 | 4/2005 | Long et al. |
| 6,942,699 B2 | 9/2005 | Stone et al. |
| 6,979,299 B2 | 12/2005 | Peabody et al. |
| 7,097,397 B2 | 8/2006 | Keightley |
| 7,112,204 B2 | 9/2006 | Justin et al. |
| 7,338,498 B2 | 3/2008 | Long et al. |
| 7,517,364 B2 | 4/2009 | Long et al. |
| 7,527,631 B2 | 5/2009 | Maroney et al. |
| 7,670,382 B2 | 3/2010 | Parrott et al. |
| 8,211,113 B2 | 7/2012 | Brown et al. |
| 8,366,713 B2 | 2/2013 | Long et al. |
| 8,444,646 B2 | 5/2013 | Long et al. |
| 2001/0009971 A1 | 7/2001 | Sherts et al. |
| 2001/0013823 A1 | 8/2001 | Hatakeyama et al. |
| 2001/0037152 A1 | 11/2001 | Rockwood, Jr. |
| 2001/0047210 A1 | 11/2001 | Wolf |
| 2002/0016634 A1 | 2/2002 | Maroney et al. |
| 2002/0099381 A1 | 7/2002 | Maroney |
| 2002/0099445 A1 | 7/2002 | Maroney et al. |
| 2002/0183849 A1 | 12/2002 | Grusin et al. |
| 2003/0018341 A1 | 1/2003 | Deloge et al. |
| 2003/0114859 A1 | 6/2003 | Grusin et al. |
| 2003/0163202 A1 | 8/2003 | Lakin |
| 2003/0212403 A1 | 11/2003 | Swanson |
| 2004/0122521 A1 | 6/2004 | Lee et al. |
| 2004/0193277 A1 | 9/2004 | Long et al. |
| 2004/0193278 A1 | 9/2004 | Maroney et al. |
| 2005/0065612 A1 | 3/2005 | Winslow |
| 2006/0052791 A1 | 3/2006 | Hagen et al. |
| 2006/0142870 A1 | 6/2006 | Robinson et al. |
| 2006/0149390 A1 | 7/2006 | Long et al. |
| 2008/0004701 A1 | 1/2008 | Axelson et al. |
| 2013/0138109 A1 | 5/2013 | Long et al. |
| 2013/0245776 A1 | 9/2013 | Long et al. |

FOREIGN PATENT DOCUMENTS

| | | |
|---|---|---|
| DE | 4220217 A1 | 12/1993 |
| DE | 10233204 A1 | 1/2004 |
| EP | 0888752 A2 | 1/1999 |
| EP | 0903128 A1 | 3/1999 |
| EP | 0845250 A2 | 6/1999 |
| EP | 1064890 A1 | 1/2001 |
| EP | 1228739 A2 | 8/2002 |
| EP | 1518519 A2 | 3/2005 |
| FR | 2 418 644 | 9/1979 |
| FR | 2418684 A1 | 9/1979 |
| FR | 2578739 A1 | 9/1986 |
| FR | 2737107 A1 | 1/1997 |
| FR | 1 470 802 A1 | 10/2004 |
| FR | 2898267 A1 | 9/2007 |
| GB | 764600 A | 12/1956 |
| GB | 2259253 A | 3/1993 |
| WO | 9415551 A1 | 7/1994 |
| WO | 9522302 A1 | 8/1995 |
| WO | 9087393 A1 | 2/1998 |
| WO | 9937254 A1 | 7/1999 |
| WO | 0113823 A2 | 3/2001 |
| WO | 0113823 A3 | 3/2001 |
| WO | 0217822 A1 | 3/2002 |

OTHER PUBLICATIONS

Japan Patent Office, Notification of Reasons for Refusal, corresponding to Japanese patent application No. 2004-099913, dated Feb. 9, 2010 (3 pages).

Australian Government—IP Australia, Examiner's First Report on Australian patent application No. 2004201349, dated Jun. 4, 2009 (7 pages).

DePuy Orthopaedics, Inc., Moreland Cemented Hip Revision Instrumentation, (12 Pages Total), 2.3M500, 0602-28-000 (REV.6) USA.

DePuy Orthopaedics, Inc., Moreland Cementless Hip Revision Instrumentation, (12 Pages Total), USA.

Smith & Nephew, Inc., Orthopaedic Catalog (25 Pages Total) Prepared Oct. 16, 2003, USA.

DePuy Ace, Engineering Drawings, Title: Articulated Tension Device Outline Drawings—Large Fragment System, P/N 13710-010, Dec. 11, 1998 (REV. C) USA.

Biomet Brochure (engineering drawings).

DePuy Orthopaedics, Inc. Global Advantage CTA Humeral Head, 2000, 3.5M0406, 0612-03-050 Rev 3), USA (6 pages).

EPO Search Report for EPO Application 04251913.2-2310, dated Dec. 5, 2005 (2 pages).

Biomet Orthopaedics, Inc., Introducing the Copeland Humeral Resurfacing Head, 2001.

Biomet Merck, Ltd., Copeland Surface Replacement Shoulder Arthroplasty, (date unknown).

Endotec, Inc. Buechel-Pappas Resurfacing Shoulder System Surgical Procedure by Frederick F. Buechel, M.D. 2001.

Biomet Orthopaedics, Inc., Copeland Humeral Resurfacing Head (date unknown).

European Search Report for European Application No. 04251871.2-1526, dated Sep. 8, 2004, 3 pages.

European Search Report for European Application No. 05251328.0-2310, dated Jul. 21, 2005, 4 pages.

Australian Government—IP Australia, Examiner's First Report on Australian patent application No. 2004201199, dated Jan. 9, 2009 (2 pages).

Australian Examiner's Report corresponding to Australian Application No. 2009213073, dated Feb. 25, 2011 (2 pages).

\* cited by examiner

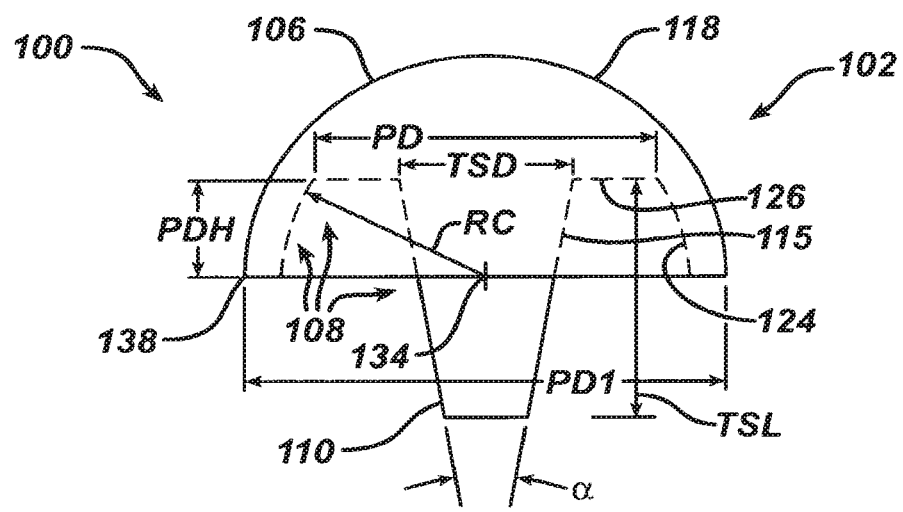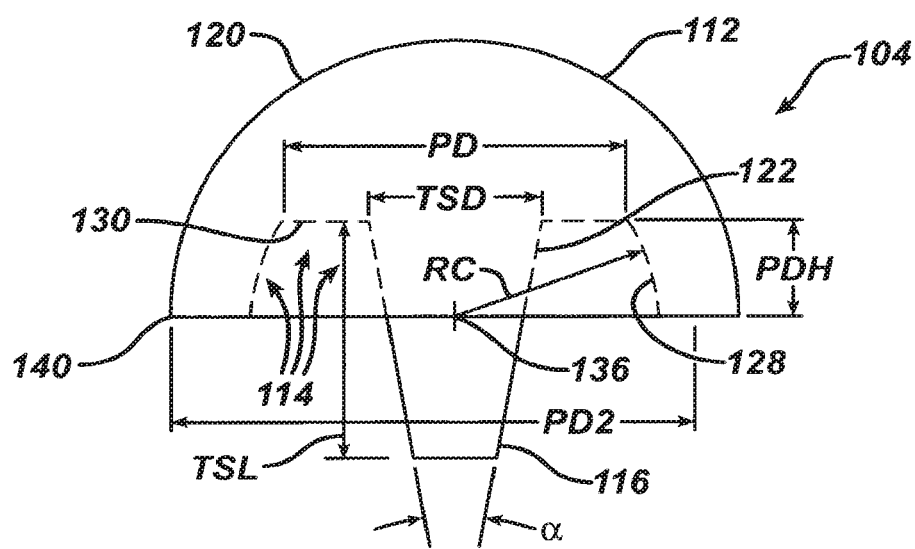
FIG. 1

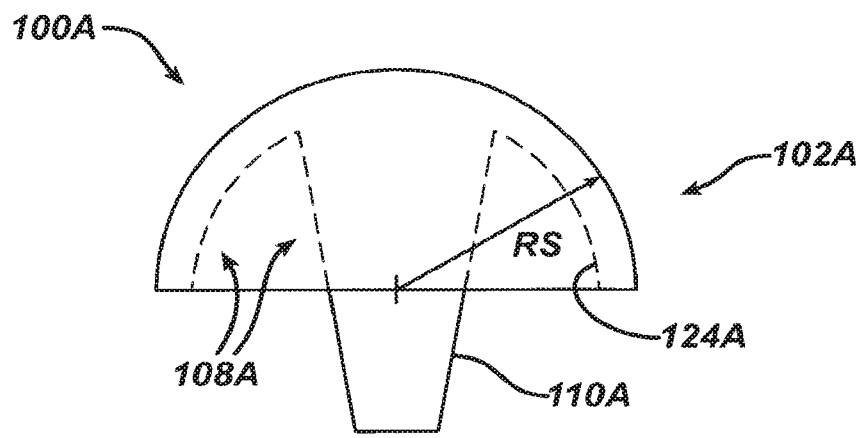
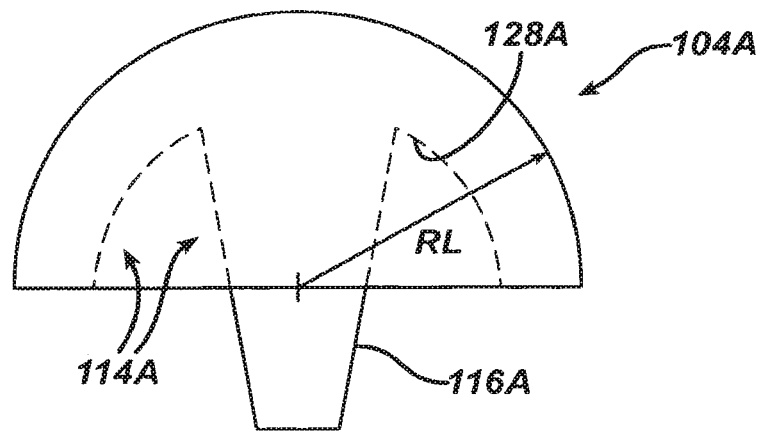
FIG. 1A

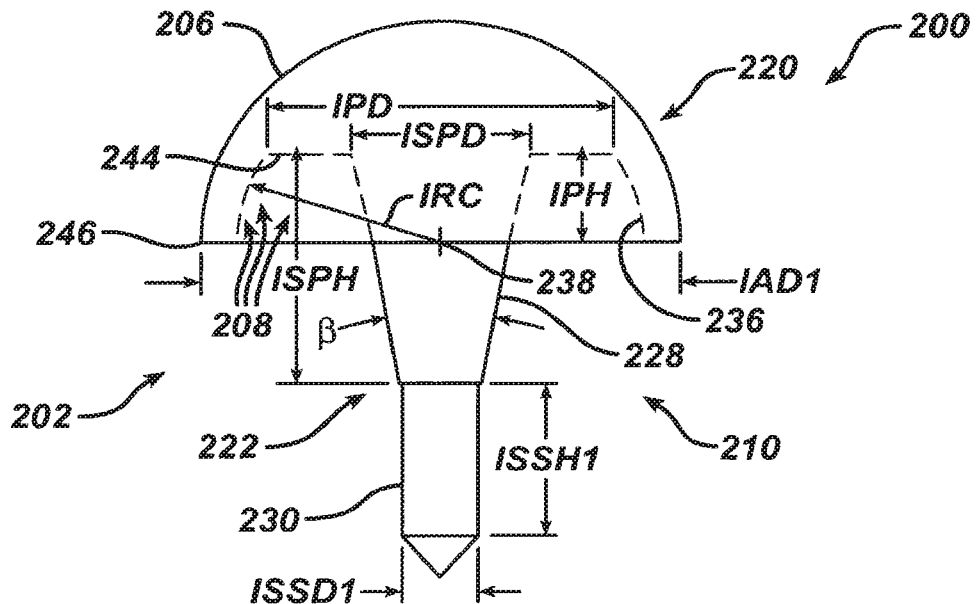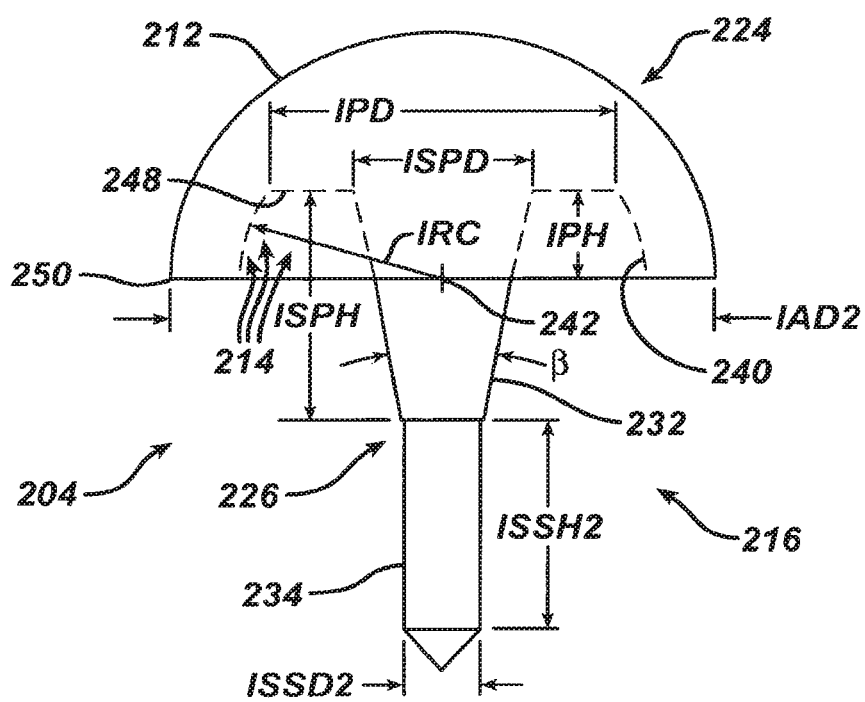
FIG. 5

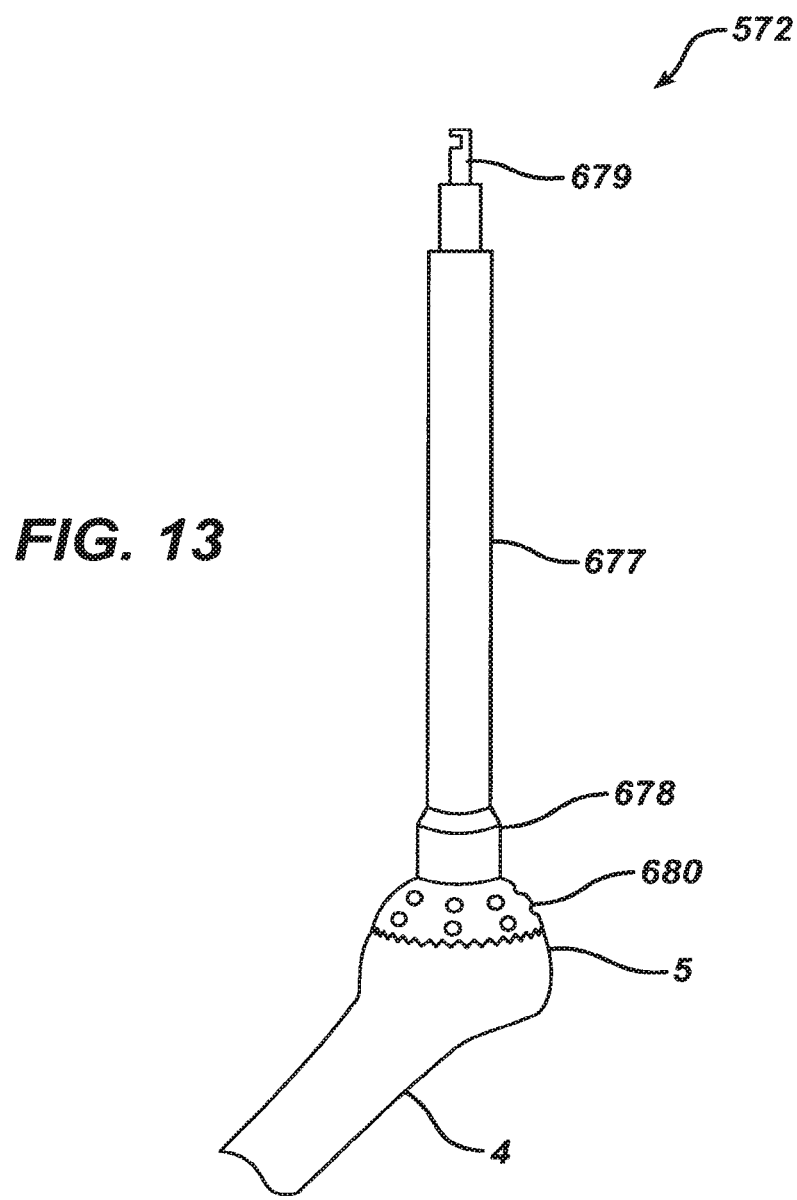

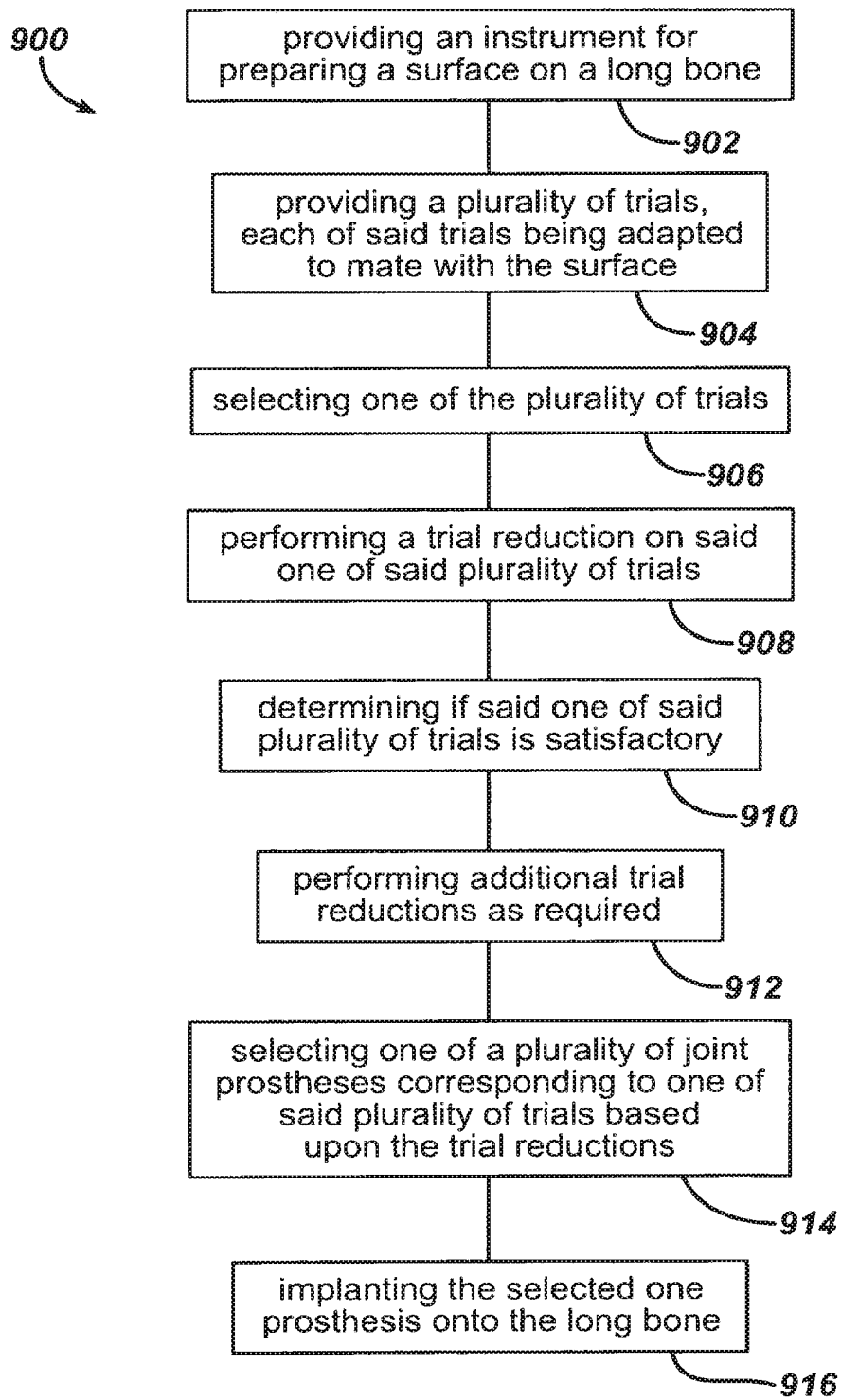

PUNCH, IMPLANT AND ASSOCIATED METHOD

CROSS REFERENCE TO RELATED APPLICATIONS

This application is a divisional of co-pending application Ser. No. 13/361,517, filed on Jan. 30, 2012 (now U.S. Pat. No. 9,849,000), which is a divisional of application Ser. No. 10/794,628, filed on Mar. 5, 2004 (now U.S. Pat. No. 8,105,327), which in turn is a continuation-in-part of application Ser. No. 10/403,364, filed on Mar. 31, 2003 (now U.S. Pat. No. 7,338,498), the disclosures of the above-identified patents and patent applications are hereby totally incorporated by reference in their entirety.

Cross reference is made to the following applications: U.S. patent application Ser. No. 10/403,707 filed Mar. 31, 2003, entitled "ARTHROPLASTY SIZING GAUGE" (now U.S. Pat. No. 7,527,631 issued May 5, 2009), U.S. patent application Ser. No. 10/403,750 filed Mar. 31, 2003, entitled "ARTICULATING SURFACE REPLACEMENT PROSTHESIS" (now abandoned), U.S. patent application Ser. No. 10/403,577 filed Mar. 31, 2003, entitled "MODULAR ARTICULATING SURFACE REPLACEMENT PROSTHESIS" (now abandoned), U.S. patent application Ser. No. 10/403,710 filed Mar. 31, 2003, entitled "ARTHROPLASTY INSTRUMENT AND ASSOCIATED METHOD" (now U.S. Pat. No. 8,366,713 issued Feb. 5, 2013), U.S. patent application Ser. No. 10/403,708 filed Mar. 31, 2003, entitled "EXTENDED ARTICULATION ORTHOPAEDIC IMPLANT AND ASSOCIATED METHOD" (now U.S. Pat. No. 7,517,364 issued Apr. 14, 2009), and U.S. patent application Ser. No. 11/900,682 filed Sep. 13, 2007, entitled "PROSTHETIC IMPLANT, TRIAL, AND ASSOCIATED METHOD" (now abandoned), the disclosures of the above-identified patents and patent applications are hereby totally incorporated by reference in their entirety.

TECHNICAL FIELD

The present invention relates generally to the field of orthopaedics, and more particularly, to an implant for use in arthroplasty.

BACKGROUND

The invention relates to implantable articles and methods for implanting such articles. More particularly, the invention relates to a bone prosthesis and a method for implanting the same.

There are known to exist many designs for and methods for implanting implantable articles, such as bone prostheses. Such bone prostheses include components of artificial joints, such as elbows, hips, knees and shoulders. An important consideration in the design and implanting of virtually any implantable bone prosthesis is that the bone have adequate fixation when implanted within the body.

Earlier designs of implantable articles relied upon the use of cement, such as polymethylmethacrylate (PMMA) to anchor the implant. The use of such implants can have some advantages, such as providing a fixation that does not develop free play or does not lead to erosion of joining faces postoperatively. However, the current trend is to use the cement to a lesser extent because of its tendency to lose adhesive properties over time. There is also a possibility that cement contributes to wear debris within a joint.

Recently, implantable bone prostheses have been designed to encourage the growth of hard bone tissue around the implant. Such implants are often implanted without cement and the bone grows around surface irregularities, for example, porous structures on the implant.

One such implantable prosthesis is a shoulder prosthesis. During the lifetime of a patient, it may be necessary to replace the natural humeral head and associated glenoid cavity with a prosthesis. Such a shoulder replacement procedure may be necessary to be performed on a patient as a result of, for example, diseases such as osteoarthritis and rheumatoid arthritis, or trauma.

Most shoulder replacement surgeries today involve the implantation of a total shoulder prosthesis. In a total shoulder replacement procedure, a humeral component having a head portion is utilized to replace the natural head portion of the upper arm bone or humerus. The humeral component typically has an elongated intramedullary stem which is utilized to secure the humeral component to the patient's humerus. In such a total shoulder replacement procedure, the natural glenoid surface of the scapula is restructured or otherwise replaced with a glenoid component that provides a bearing surface for the head portion of the humeral component.

With the average age of patients requiring shoulder arthroplasty surgery decreasing, orthopaedic implant manufacturers are developing "bone-sparing" implants for the initial treatment of the degenerative arthritis. While bone-sparing implants for the treatment hip and knee arthroplasty are becoming quite common, bone-sparing shoulder arthroplasty techniques and prostheses are also being developed.

Shoulder surface replacement prostheses are being developed to replace the articulating surface of the proximal humerus with a minimal bone resection and minimal disruption of the metaphysis and the diaphysis. Current designs use a semi-spherical articular dome with a small stem for rotational stability. The under surface of the articular head is also semi-spherical and meets with a spherically machined humeral head.

Typically, however, arthritis of the gleno-humeral joint causes flattening of the humeral head with a large medial osteophyte. The flat humeral head can cause voids in the bone under the prosthesis resulting in limited contact between the prosthesis and the resected bone and may limit the load transfer capability between the prosthesis and the humerus.

Referring now to FIG. 2, a healthy long bone or, in the form of, for example, a humerus 1 is shown. The humerus 1 includes a head 2 on the proximal end of the humerus 1. The head 2 of a healthy humerus has an arcuate outer periphery. The arcuate outer periphery is generally hemispherical and meets with a concave glenoid cavity 3.

Referring now to FIG. 3, a diseased humerus 4 is shown. The diseased humerus 4 includes a head 5. The head 5 is flattened as shown in FIG. 3. The humerus 4 also has developed a large medial osteophyte 7.

Referring now to FIG. 4, a prior art prosthesis 8 is shown in position on the head 5 of diseased humerus 4. The head 5 includes a flattened humeral head area or bony defect 9 which leads to a void 6 between the prosthesis 8 and the bony defect 9.

Due to variations in the size and bone configuration of patients, as well as, to the variations in the progress of the diseased long bone and the resultant amount of flattening of the humeral head, a wide variety of sizes and shapes of prostheses are necessary to have a proper fitting prosthesis for most patients.

So that a surgeon may determine and have available the proper prosthesis for a patient, preoperatively, the surgeon may use radiographic techniques such as x-rays to obtain an image of the bone and from that image select the appropriate size prosthesis.

Typically, the surgeon will have available at the operating room the predetermined prosthesis and perhaps the next available size or two both smaller and larger. To verify that the preselected prosthesis is best suited for the patient, orthopaedic prosthesis manufacturers have developed non-implanting substitute prostheses or trials that have the same dimensions as the respective implants and are used to replicate a prosthesis. After the surfaces and cavities are prepared for receiving the prosthesis, the trial is implanted. The arm is then moved through the normal range of motion to determine the appropriateness of the trial and the resulting prosthesis. Such a procedure is called a trial reduction.

Sometimes, the trial reduction will determine that the preselected prosthesis is not optimum for the patient. A larger and sometimes a smaller prosthesis will be more optimum than that preselected. Trials are available with proportional dimensions as they become larger. Thus, a conservative or bone sparing humeral head prosthesis for a smaller articulating surface may also have a smaller stem.

The surgeon first prepares the cavity to receive the stem and the surface to receive the head. If a prosthesis smaller than that originally predicted is required for the patient, the resulting smaller prosthesis and a similarly sized smaller prosthetic trial needs to be placed in the patient. Such a smaller trial does not fit snugly in the prepared cavity. Thus, bone graft needs to be placed in the cavity and the prosthesis placed between the bone graft material and the bone. Such a procedure takes added time in the operating room, causes greater expense and may cause error in positioning, as well as, may not optimize the fixation of the prosthesis.

Referring now to FIG. 6, the prior art prosthesis 8 is shown on the head 5 of the diseased humerus 4. Stem 10 of the prosthesis 8 extends from body 11 of the prosthesis 8. As can be seen, the prosthesis 8 is, for example, a smaller prosthesis than the prosthesis that the head was prepared to receive. A smaller prosthesis was determined to be required after the initial trial reduction with the larger prosthesis. Therefore, a prepared tapered cavity 14 into which the stem 10 is to fit is much larger than the stem 10. Since the cavity 14 was prepared for a larger prosthesis with a correspondingly larger stem, bone graft material 15 is required within the cavity 14 to provide for a secure fitting of the stem 10 to the humerus 4. It should be appreciated that because of the placing of the bone graft and the difference in size between the cavity 14 and the stem 10, the stem 10 and the corresponding prosthesis 8 may be misplaced from its ideal central location in the direction of arrow 16 or rotationally in the direction of arrow 18.

Once a humerus is prepared to receive a partial or conservative and replacing the prosthesis the accurately placing of the prosthesis onto the prepared humeral head is important in proper operation of the prosthesis and the proper range of motion that the prosthesis will permit. Typically, the stem head replacing prosthesis is tapped into positioned into the humeral cavity that maybe prepared. Even a slight mis-positioning of the prosthesis in the prepared head will make a significant difference in the range of motion and the proper positioning of prosthesis.

The present invention is aimed to improving the ability to properly position the head replacing implant.

SUMMARY

The present invention provides for a surgical technique, as well as, for a kit of trials and a kit of implants that eliminate excess reaming of the cavity to receive a conservative or bone sparing long bone head prosthesis. Trials and prostheses with different articulating surface dimensions utilize a common stem geometry such that the prepared cavity can be identical for a range of implant trials and resultant prosthesis. This method provides for an elimination of the excess reaming due to different size trial stems.

According to the present invention, a tool is provided to assist in the proper placement of the prosthetic head replacement implant, for example, a humerus or a femur. Such an instrument maybe in the form of punch. The conservative prosthesis cruciate punch may be used to create an axial impression of the implant's distal tip in the proximal humerus or femur. The impress is used as a pilot to insure the implant is correctly oriented for impaction seating. The cruciate implant stem is designed to increase the initial fixation and rotational stability of the implant once the implant is seated. The conservative stem punch creates an axial of the distal stem of the implant into the proximal humerus. The conservative prosthesis cruciate punch may be used with or without a guide wire. A punch therefore may have a center opening to receive a guide wire. The device may include laser markings that indicate the depth of the stem, and the angular orientation of the cruciate stem fin.

According to one embodiment of the present invention, a kit for use in performing joint arthroplasty on a head of a long bone is provided. The kit includes a first trial including a first trial articulating surface and an opposed first trial mounting surface having a first trial location feature. The kit also includes a second trial including a second trial articulating surface and an opposed second trial mounting surface having a second trial location feature. The first trial articulating surface and the second trial articulating surface have different geometries and the first trial location feature and the second trial location feature have substantially identical geometries whereby different trials may be used with a common location feature.

According to another embodiment of the present invention, a kit for use in performing joint arthroplasty on a head of a long bone is provided. The kit includes a first implant including a first implant articulating surface and an opposed first implant mounting surface having a first implant location feature. The kit also includes a second implant including a second implant articulating surface and an opposed second implant mounting surface having a second implant location feature. The first implant articulating surface and the second implant articulating surface have different geometries and the first implant location feature and the second implant location feature have substantially identical geometries whereby different implants may be used with a common location feature.

According to a further embodiment of the present invention, a kit for use in selecting one of a plurality of humeral shoulder joint implants for use in shoulder arthroplasty is provided. The kit includes an instrument for preparing a surface on a humerus and a first trial. The first trial cooperates with the humerus. The first trial has a first trial first portion fittable with the surface of the humerus and has a first trial second portion for cooperation with the glenoid cavity. The kit also includes a second trial for cooperation with the humerus. The second trial has a second trial first portion fittable with the surface of the humerus and has a second trial second portion for cooperation with the glenoid cavity. The first portion of the first trial and the first portion of the second trial are substantially identical and the second portion of the first trial and the second portion of the second trial are substantially different.

According to yet another embodiment of the present invention a kit for use in shoulder arthroplasty is provided. The kit includes a first trial for cooperation with the humerus. The first trial has a first trial first portion fittable with the surface of the humerus and has a first trial second portion for cooperation with the glenoid cavity. The kit also includes a second trial for cooperation with the humerus. The second trial has a second trial first portion fittable with the surface of the humerus and has a second trial second portion for cooperation with the glenoid cavity. The first portion of the first trial and the first portion of the second trial are substantially identical and the second portion of the first trial and the second portion of the second trial being substantially different.

According to a further embodiment of the present invention, a method for providing joint arthroplasty is provided. The method includes the steps of providing an instrument for preparing a surface on a long bone, providing a plurality of trials, each of said trials being adapted to mate with the surface, selecting one of the plurality of trials, performing a trial reduction on said one of said plurality of trials, determining if said one of said plurality of trials is satisfactory, performing additional trial reductions as required, selecting one of a plurality of joint prostheses corresponding to one of said plurality of trials based upon the trial reductions, and implanting the selected one prosthesis onto the long bone.

According to a yet another embodiment of the present invention, a humeral trial for use in performing joint arthroplasty on the head of a long bone is provided. The trial includes a body having an arcuate articulating surface and an opposed mounting surface. The mounting surface includes a portion of the mounting surface which is generally planar.

According to another embodiment of the present invention, there is provided an implant for use in performing joint arthroplasty on the head of a long bone. The implant includes a body having arcuate articulating surface and an opposed mounting surface. The mounting surface includes a portion of the mounting surface, which is generally planar.

According to another embodiment of the present invention, there is provided an instrument for preparing a cavity for a stem of a prosthetic implant for use in performing joint arthroplasty on a head of a long bone. The instrument includes a body and a punch extending from the body. The punch includes a portion of the punch having a shape similar to the stem of the implant.

According to another embodiment of the present invention, there is provided a kit for use in performing joint arthroplasty on a head of a long bone. The kit includes a first implant having a first implant articulating surface and an opposed first implant mounting surface having a first implant location feature. The kit also includes an instrument for preparing a cavity in the head of the long bone. The instrument has a body and a punch extending from the body. The punch has a portion of the punch having a shape similar to the first implant location surface of the implant.

According to another embodiment of the present invention, there is provided a method for providing joint arthroplasty. The method includes the steps of preparing a surface on a long bone, providing an implant having a stem. The method further includes the step of providing an instrument for cooperation with the surface of the long bone, the instrument having a body and a punch extending from the body. The punch includes a portion thereof having a shape similar to the stem of the implant. The method also includes the steps of using the instrument to prepare the surface for the implant and implanting the implant onto the long bone.

The technical advantages of the present invention include improved positioning of the trial and implant during the surgery. For example, according to one aspect of the present invention, various size implants and trials all use a common stem size. By providing the common stem size, a stem cavity can be prepared and utilized, not only for the preselected and trial size, but for a smaller trial which may otherwise be in a condition of moving into an offset center position or not perfectly positioned with the bone graft is placed to fill the space between the over-reamed cavity and the smaller stem. Thus, the present invention provides for improved location of the trial.

The technical advantages of the present invention further include improved support for the prosthesis and resultant improved fixation. For example, according to another aspect of the present invention, a plurality of trials and a plurality of corresponding implants are provided with a common size and geometry stem. The long bone is prepared with a common cavity to receive the plurality of trials and resulting stems. Thus, for a variety of trials, even a smaller trial which would otherwise have a smaller stem and require bone graft between the cavity and the stem, the trial stems and implant stems are firmly fitted to the cavity and provide adequate support for the trial and the implant and improved fixation. Thus, the present invention provides for improved support and improved fixation of the prosthesis.

Another technical advantage of the present invention includes reduced time in the operating room. For example, according to one aspect of the present invention, a plurality of trial sizes and implant sizes utilize a common size stem. Thus, the change in the trial size determined by a trial reduction will result in a smaller trial with the same size stem. The use of the same size stem will obviate the need of bone graft material being placed between the stem and the cavity and thus reduce the amount of time to perform such bone grafting in the operating room. Thus, the present invention reduces time in the operating room.

The technical advantages of the present invention further include a reduction in cost in performing the arthroplasty. For example, according to one aspect of the present invention, a plurality of trials and prostheses utilize a common stem. The stem may be provided with a common reamer. Since a common reamer can be used for various size trials and prostheses, the costs associated with a greater number of reamers can be reduced.

The technical advantages of the present invention include improved rotational stability of the surface replacement prosthesis. For example, according to one aspect of the present invention, a punch and an implant are provided with corresponding or matching fins in the punch and implant, with the punch making an impression to match the implant. Therefore, the present invention provides for rotational stability of a head resurfacing implant.

The technical advantages of the present invention, further include the ability of the present invention to permit accurate axial alignment of a surface replacement prosthesis. For example, according to one aspect of the present invention, a stop is provided on the punch to limit the depth of insertion of the punch into the pre-reamed hole of the stem of the orthopaedic implant. The stop includes first and second selectable positions. In the first position, the punch has a short depth for matingly fitting into the pre-reamed hole of the long bone. The punch further includes an axial marker on the periphery of the stop for pre-selection of the location of depression on the punch. The stop further includes a second position in which the punch may be further inserted into the long bone to provide the depressions and the opening for the insertion of the implant. The present invention provides for accurate axial alignment of the implant.

Yet another technical advantage to the present invention includes the superior implant fixation and accurate alignment provided by the punch. For example, according to one aspect of the present invention, a stop is provided to set a punch depth with the implant depth. The stop permits the punch to prepare an opening for receiving the stem of the implant in which opening has a depth and a depression. The punch provides for accurate alignment while permitting additional depth to be obtained for improved fixation by first positioning or tapping the implant into the cancellous bone of the long bone. Thus, the present invention provides for superior fixation with accurate alignment of the implant into the long bone.

The technical advantages of the present invention further include the ability to easily angularly orient the surface replacement implant and its associated instruments. For example, according to another aspect of the present invention, the implant is provided with a plurality of fins in the stem portion, which correspond to depressions formed in the long bone created by matting fins in the stem of the punch. Further the punch may include laser markings in alignment with the fins located, for example, in the outer periphery of the stop of the punch. By visually positioning the punch and corresponding laser marking on the punch in the desired orientation, the angular orientation of the resulting implant may be easily determined. Thus the present invention provides for a method to easily orient the implant.

The technical advantages to the present inventions further include the inability to inadvertently misalign an implant during installation onto a long bone. For example, according to another aspect of the present invention, the implant includes a plurality of fins on the stem, which correspond with a depression formed in the cavity of the long bone for receiving the implant. The cavity is provided by a stem on a punch with fins. The punch fins match or correspond to the fins on the implant. Further the punch may include a stop with two positions with the stop set to correspond to a partial depth of the punch to provide for alignment yet provide superior fixation. The punch, thus, provides for installation of an implant that cannot be inadvertently misaligned.

The technical advantages of the present invention, further includes the ability to provide a pocket for receiving a stem of a prosthesis that includes an undisturbed impression. For example, according to one aspect of the present invention a punch for providing an impression includes a portion for striking with, for example, a hammer having an inside face to permit striking in the direction opposed to the punch. Thus, the punch may be moved without disturbing the impression. Thus the present invention provides an undisturbed impression or hole for receiving a stem of an implant.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 1 is a plan view of a trial kit according to the present invention for use in performing shoulder arthroplasty on a diseased humerus;

FIG. 1A is a plan view of another embodiment of a trial kit according to the present invention for use in performing shoulder arthroplasty on a diseased humerus;

FIG. 5 is a plan view of an implant kit according to the present invention for use in performing shoulder arthroplasty on a diseased humerus;

FIG. 13 is a view of the reamer of FIG. 9 show in position on a humerus;

FIG. 14 is a process flow chart for a method of performing shoulder arthroplasty surgery according to another embodiment of the present invention;

DETAILED DESCRIPTION

Figure 2:
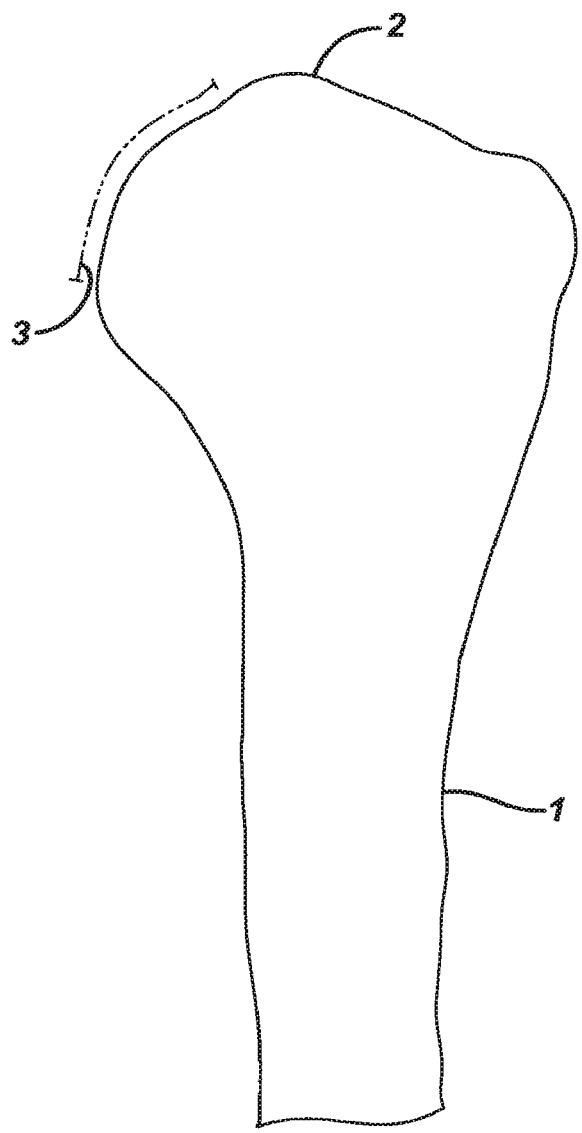
FIG. 2 is a plan view of a healthy humerus.
Figure 3:
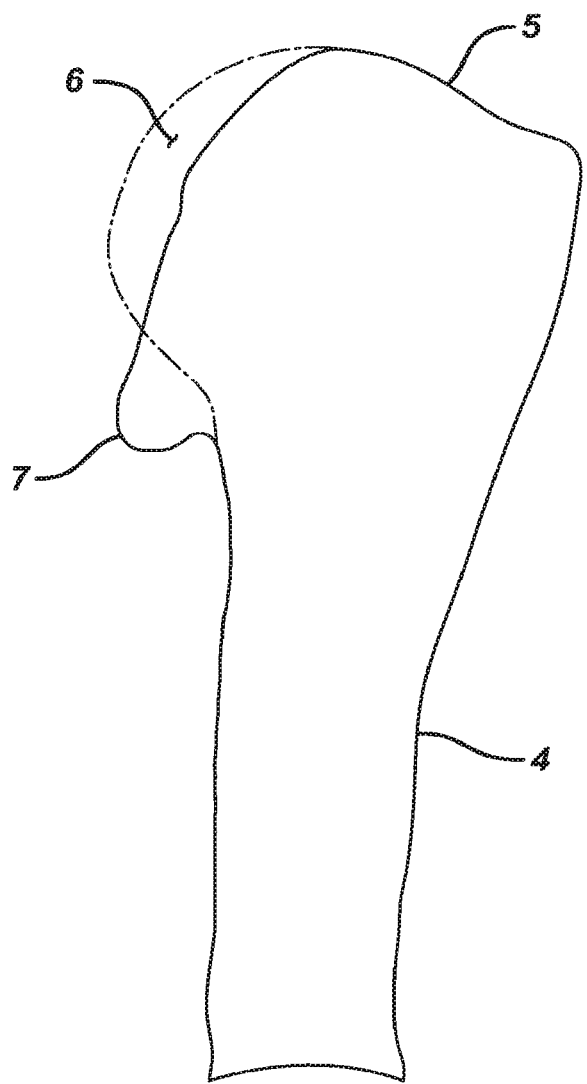
FIG. 3 is a plan view of a diseased humerus.
Figure 4:
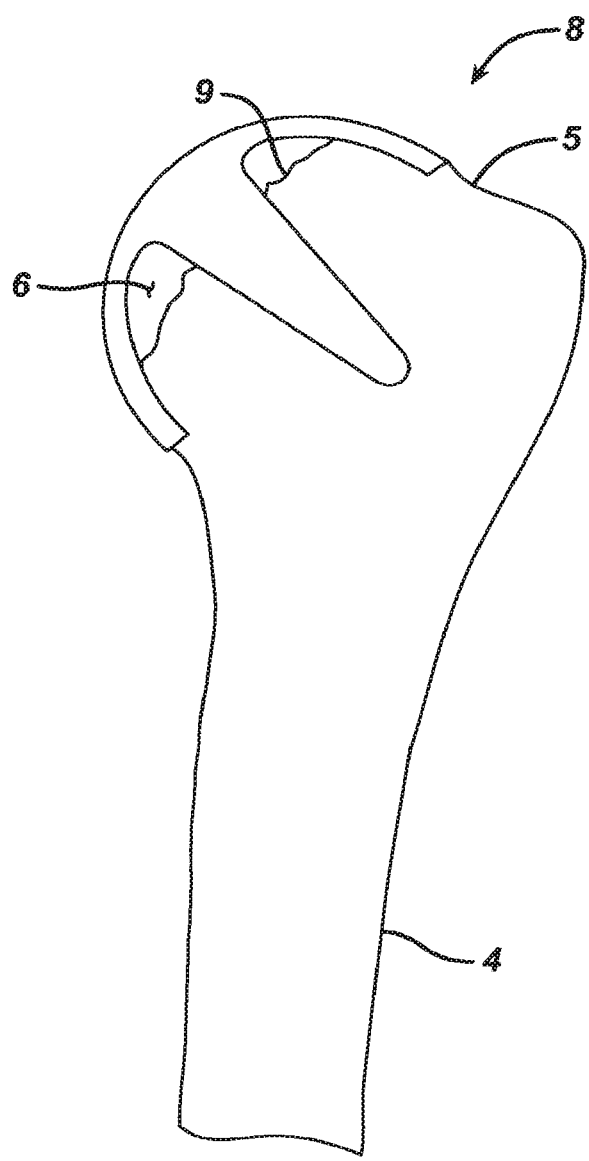
FIG. 4 is a plan view of a prior art surface replacement prosthesis.
Figure 6:
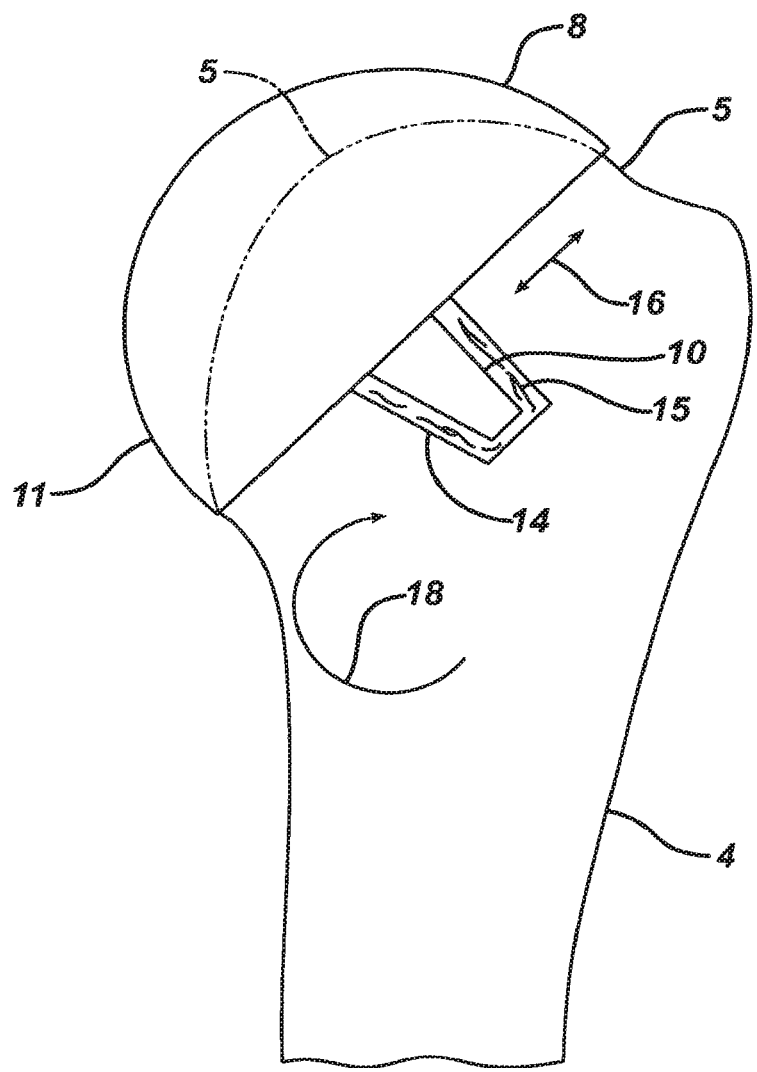
FIG. 6 is a plan view of a small shoulder prior art implant in position on a resected humerus with a tapered opening sized for a large prior art shoulder implant.

Embodiments of the present invention and the advantages thereof are best understood by referring to the following descriptions and drawings, wherein like numerals are used for like and corresponding parts of the drawings.

Referring now to FIG. 1, an embodiment of the present invention is shown as trial kit 100. The kit 100 is used for performing joint arthroplasty on a head of a long bone. The trial kit 100 includes a first trial 102 as well as a second trial 104. The first trial 102 includes a first trial articulating surface 106 and an opposed first trial mounting surface 108. The first trial mounting surface 108 includes a first trial location feature 110.

The second trial 104 includes a second trial articulation surface 112 and an opposed second trial mounting surface 114. The second trial mounting surface 114 includes a second trial location feature 116. The first trial articulating surface 106 and the second trial articulating surface 112 have different geometries. The first trial location feature 110 and the second trial location feature 116 have substantially identical geometries.

Since the first trial 102 and the second trial 104 have location features 110 and 116, respectively, which are substantially identical, a common reamer 680 (see FIG. 10) and a resulting identical cavity can be prepared and utilized for both the first trial 102 and the second trial 104. If, for example, the surgeon were to determine from radiograph techniques that the second trial 104 and its corresponding implant is ideal for the patient, the second trial 104 is implanted into the patient and a trial reduction is performed. The trial reduction may show that, in fact, a smaller prosthesis and corresponding trial would be preferred. Thus, the first trial 102 could be placed in the patient after the second trial 104 was removed. The first trial 102 would have the same location feature and be securely fittable to the cavity prepared for the second trial 104.

The first trial 102 and the second trial 104 may have any suitable shape capable of performing the trial function. For example and as shown in FIG. 1, the first trial may include a body 118 and a stem 115 extending from the body 118. Similarly, the second trial 104 may include a body 120 and a stem 122 extending from the body 120.

As shown in FIG. 1, the body 118 of the first trial 102 may be arcuate. The first trial articulating surface 106 may be convex and the body 118 may have a concave portion 124 of the first trial mounting surface 108 that is concave. For example and as shown in FIG. 1, the body 118 may be generally in the shape of a hollow hemisphere. The first trial mounting surface 108 may include a planar portion 126 to correspond with, for example, a resected portion of the humerus to accommodate the flattened head resulting from osteoarthritis.

As shown in FIG. 1, the first trial 102 and the second trial 104 of the trial kit 100 preferably include the first trial mounting surface 108 and the second trial mounting surface 114 on the first trial 102 and the second trial 104, respectively, that are identical. For example, the second trial 104 may include a concave portion 128 that is identical in geometry to the concave portion 124 of the first trial 102. Similarly, the second trial 104 may include a planar portion 130 which has substantially identical dimensions with the planar portion 126 of the first trial 102.

As shown in FIG. 1, the location features 110 and the location features 116 may be, for example, in the form of a tapered protrusion, for example, in the form of a truncated cone or a tapered cylinder.

As shown in FIG. 1, the first trial mounting surface 108 and the second trial mounting surface 114 may be dimensionally identical. For example, the concave portion 124 of the first trial mounting surface 108 may be defined by a radius RC extending from origin 134 and the concave portion 128 of the second trial mounting surface 114 is similarly defined by radius RC originating from origin 136. It should be appreciated that the origin 134 and the origin 136 are geometrically positioned in a like position with respect to the first trial mounting surface 108 and the second trial mounting surface 114, respectively.

Similarly, the planar portion 126 of the first trial mounting surface 108 is defined by a diameter PD positioned at a dimension PDH from periphery 138 of the body 118. The planar portion 130 of the second trial mounting surface 114 is identical in size and shape to the planar portion 126 of the first trial mounting surface 108. The second trial mounting surface planar portion 130 is thus defined by diameter PD located at a distance PDH from periphery 140 of the second body 120.

The tapered protrusion 110 of the first trial mounting surface 108 is identical in size and shape to the location feature 116 of the second trial mounting surface 114. The location feature 110 of the first trial mounting surface 108 may be defined by diameter TSD and the height TSL. The location feature 110 is further defined by an included angle "α". Similarly, the location feature 116 of the second trial mounting surface is identically defined by location feature diameter TSD and location feature height TSL. The location feature 116 is further defined by included angle "α".

As shown in FIG. 1, the periphery 138 of the first trial 102 defines a periphery diameter PD1. Similarly, the periphery 140 of the second trial 104 defines a periphery diameter PD2. As shown in FIG. 1, the periphery diameter PD2 is greater than the periphery diameter PD1. It should be appreciated that additional trials (not shown) may be provided having periphery diameters smaller or larger or between the sizes of the periphery diameters PD1 and PD2. Thus, a wide variety of trials may be provided with identical mounting surfaces.

While the trials, according to the present invention, may include planar portions, conifrustrical portions and arcuate portions as shown in the trials 102 and 104 of FIG. 1, other configurations of the mounting surfaces may be provided.

Referring now to FIG. 1A, another embodiment of the present invention is shown as trial kit 100A. Trial kit 100A includes a first trial 102A and a second trial 104A. The first trial 102A includes a first trial mounting surface 108A and the second trial 104A includes a second trial mounting surface 114A. The first trial mounting surface 108A is identical to the second trial mounting surface 114A. As shown in FIG. 1A, the first trial mounting surface 108A includes location feature 110A and concave portion 124A. The first trial mounting surface 108A does not include a planar portion like that of the first trial 102 of the trial kit 100 of FIG. 1. The second trial mounting surface 114A of the second trial 104A, similarly, does not include a planar portion, but includes a concave portion 128A and a location feature 116A.

Referring now to FIG. 5, another embodiment of the present invention is shown as implant kit 200. The kit 200 includes a first implant 202 and a second implant 204. The first implant 202 includes a first implant articulating surface 206 and an opposed first implant mounting surface 208. The first implant mounting surface 208 includes a first implant location feature 210.

The second implant 204 includes a second implant articulating surface 212, and an opposed second implant mounting surface 214. The second implant mounting surface 214 includes a second implant location surface 216.

As shown in FIG. 5, the first implant articulating surface 206 and the second implant articulating surface 212 have different geometries or sizes. Also, the first implant location feature 210 and the second implant location feature 216 have substantially identical geometries. Therefore, as shown in FIG. 5, the first implant 202 and the second implant 204 may be used with location features 210 and 216, which are common or identical.

The first implant 202 and the second implant 204 may have any geometry suitable for resurfacing the head of a long bone. For example, as shown in FIG. 5, the first implant 202 may include a body 220 and a stem 222 extending from the body 220. Similarly, the second implant 204 may include a body 224 and a stem 226 extending from the body 224.

The bodies 220 and 224 of the implants 202 and 204, respectively, may have any suitable shape and may, for example, be in the form of a truncated hollow sphere. The stems 222 and 226 of the first implant 202 and the second implant 204, respectively, may have any suitable shape and may be in the form of, for example, a tapered cylinder.

For example, and as shown in FIG. 5, the stem 222 may include a positioning portion 228 which has a generally tapered cylindrical shape and a securing portion or anchoring feature 230 which is generally cylindrical. Similarly, the stem 226 of the second implant 204 may include a positioning portion 232 extending from the body 224. The positioning portion 232 may have a generally tapered cylindrical shape. The stem 226 may further include a securing portion or anchoring feature 234 having a generally cylindrical shape and extending from the positioning portion 232.

As shown in FIG. 5, the first implant articulating surface 206 may be defined by diameter IAD1. Similarly, the second implant articulating surface 212 may be defined by IAD2. The dimensions of IAD1 and IAD2 may be substantially different with, for example, the dimension IAD2 being significantly larger than the dimension IAD1. It should be appreciated that additional implants (not shown) may be provided with identical dimensions for the mounting surfaces and different dimensions for the implant articulating surfaces. For example, prostheses may be provided with dimensions smaller than IAD1, larger than IAD2 and with dimensions having sizes between IAD1 and IAD2.

As shown in FIG. 5, the first implant mounting surface 208 may include a concave portion 236 being defined by dimension IRC extending from origin 238. Similarly, the second implant mounting surface 214 may include a concave portion 240 being defined by a radius IRC extending from origin 242. It should be appreciated that the origins 238 and 242 are positioned relative to the other dimensions of their respective implants identically.

As shown in FIG. 5, the first implant mounting surface 208 may include a planar portion 244 defined by diameter IPD and by height IPH extending from periphery 246 of the body 220. Similarly, the second implant mounting surface 214 includes a planar portion 248. The planar portion 248 is identical in size and shape to the planar portion 244 of the first implant 202. The planar portion 248 is defined by diameter IPD and height IPH extending from periphery 250 of the second body 224.

Again referring to FIG. 5, the first implant mounting surface includes positioning portion 228 of the stem 222. The positioning portion 228 may serve as the first implant location feature 210. The positioning portion 228 of the stem 222 may be defined by a diameter ISDP and a height ISPH. The positioning portion 228 of the stem 222 may further be defined by included angle "β". The positioning portion 232 of the stem 226 of the second implant 204 is identical in size and shape to the positioning portion 228 of the stem 222 of the first implant 202. The positioning portion 232 of the stem 226 is similarly defined by the diameter ISPD and the height ISPH. The stem 226 is further defined by included angle "β".

Referring now to FIGS. 1 and 5, the trial kit 100 may be used in conjunction with the implant kit 200. For example, the first trial 102 may correspond to the first implant 202 and the second trial 104 may correspond to the second implant 204.

For example, and continuing to refer to FIGS. 1 and 5, the dimensions PD and PDH of the trials 102 and 104 may correspond to the dimensions IPD and IPH, respectively, of the first implant 202 and the second implant 204. Similarly, the dimension PD of the planar portion 126 and 130, respectively, of the first trial 202 and the second trial 204 may correspond to the dimension IPD of the first implant 202 and the second implant 204. Similarly, the dimensions TSD and TSL of the first trial 102 and the second trial 104 may correspond to the dimensions ISPD and ISPH of the first implant 202 and the second implant 204. Further, the angle "α" of the kit 100 may be equal to the angles "β" of the kit 200.

As shown in FIG. 5, to provide for ample securing of the implants 202 and 204 into the head of the long bone, the implants 202 and 204 may include securing portions 230 and 234, respectively. The securing portions 230 and 234 of the implants 202 and 204, respectively, are utilized to provide ample securing of the implants into the bone. Therefore, the securing portions 230 and 234 are pressed into un-reamed portions of the cancellous bone. Since the area in which the securing portion is placed into bone is not prepared by the reamer and does not correspond to a portion of the trials, the securing portions for an implant may be different implant to implant and not interfere with the kits and method of the present invention.

To provide for the optimum securing of the implants, the securing portions may be longer than the corresponding trial stems to provide for adequate fixation. Also, since most bone configurations are proportional, the larger implants should have a corresponding longer stem. Thus, the use of a longer stem with a larger prosthesis is still possible with the common trial locating features and generally common implant features of the kit and method of the present invention.

For example, and as shown in FIG. 5, the securing portion 230 of the first implant 202 and the securing feature 234 of the second implant 204 may have different lengths. For example, the securing portion 230 of implant 202 may have a length ISSH1. Similarly, the securing portion 234 of the second implant 204 may have a different length, for example, a longer length, for example ISSH2. The securing portions 230 and 234 of the first implant 202 and the second implant 204, respectively, may have common diameters or may have different diameters, for example, ISSD1 for first implant 202 and ISSD2 for second implant 204.

The implants 202 and 204 may be made of any suitable, durable material that is compatible with the human body. The implants 202 and 204 may, for example, be made of a metal, for example, a cobalt chromium alloy, a stainless steel alloy or a titanium alloy.

Figure 7:
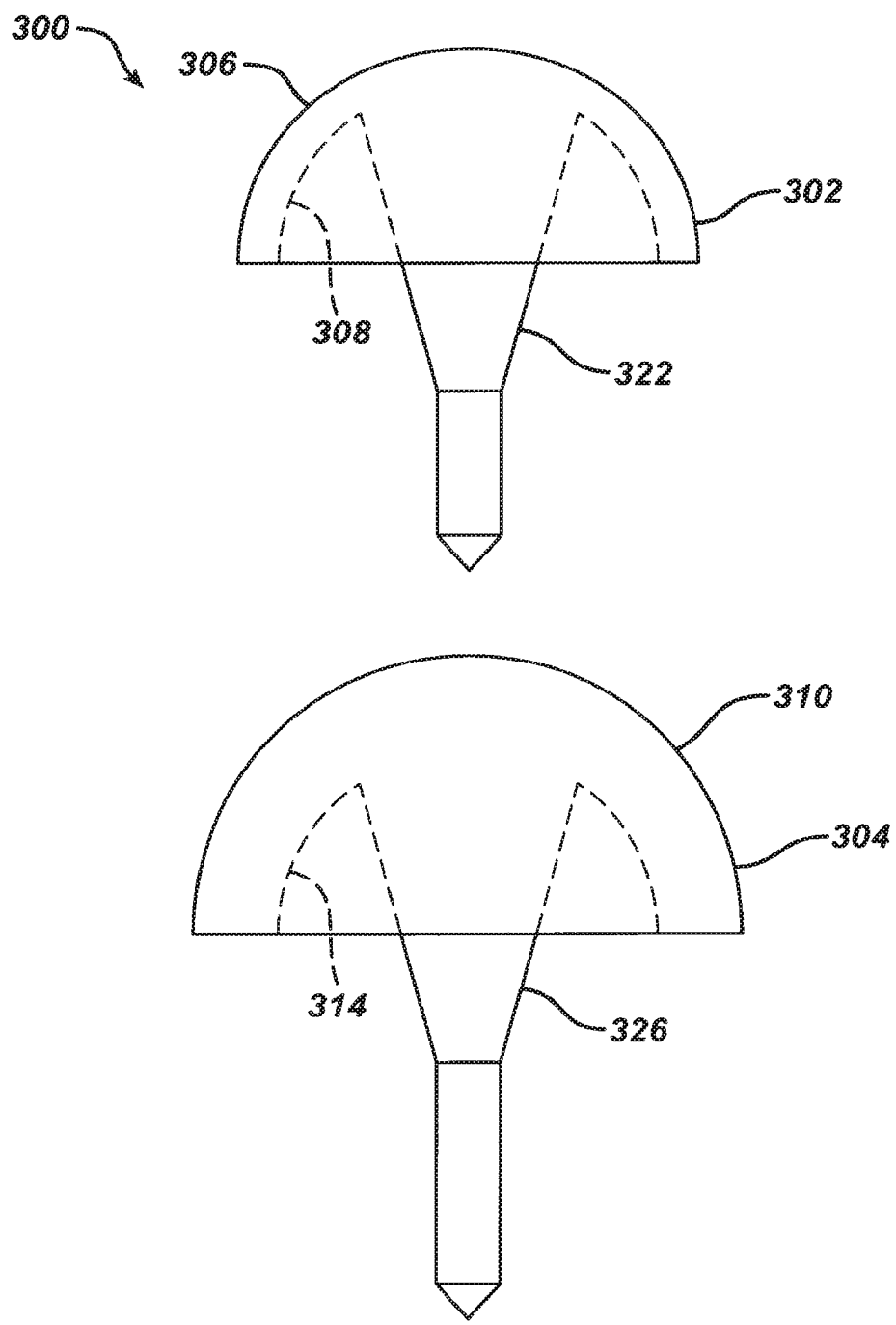
FIG. 7 is a plan view of another embodiment of an implant kit according to the present invention for use in performing shoulder arthroplasty on a diseased humerus.

Referring now to FIG. 7, another embodiment of the present invention is shown as implant kit 300. Implant kit 300 includes a first prosthesis 302 and a second implant 304. The first implant 302 includes a first prosthesis articulating surface 306 and a stem 322. The first prosthesis 302 further includes a mounting surface 308. It should be appreciated that the mounting surface 308 is different than the mounting surface 208 of the first implant 202 of the implant kit 200 of FIG. 5. Mainly, the first implant 302 does not include a planar portion. Similarly, the second prosthesis 304 includes a second prosthesis articulating surface 310 and an opposed mounting surface 314. The second prosthesis 304 also includes a stem 326. The mounting surface 314 of the second prosthesis 304 also does not include a planar portion. It should be appreciated that the implant kit 300 may be utilized with the trial kit 100A of FIG. 1A.

Figure 7A:
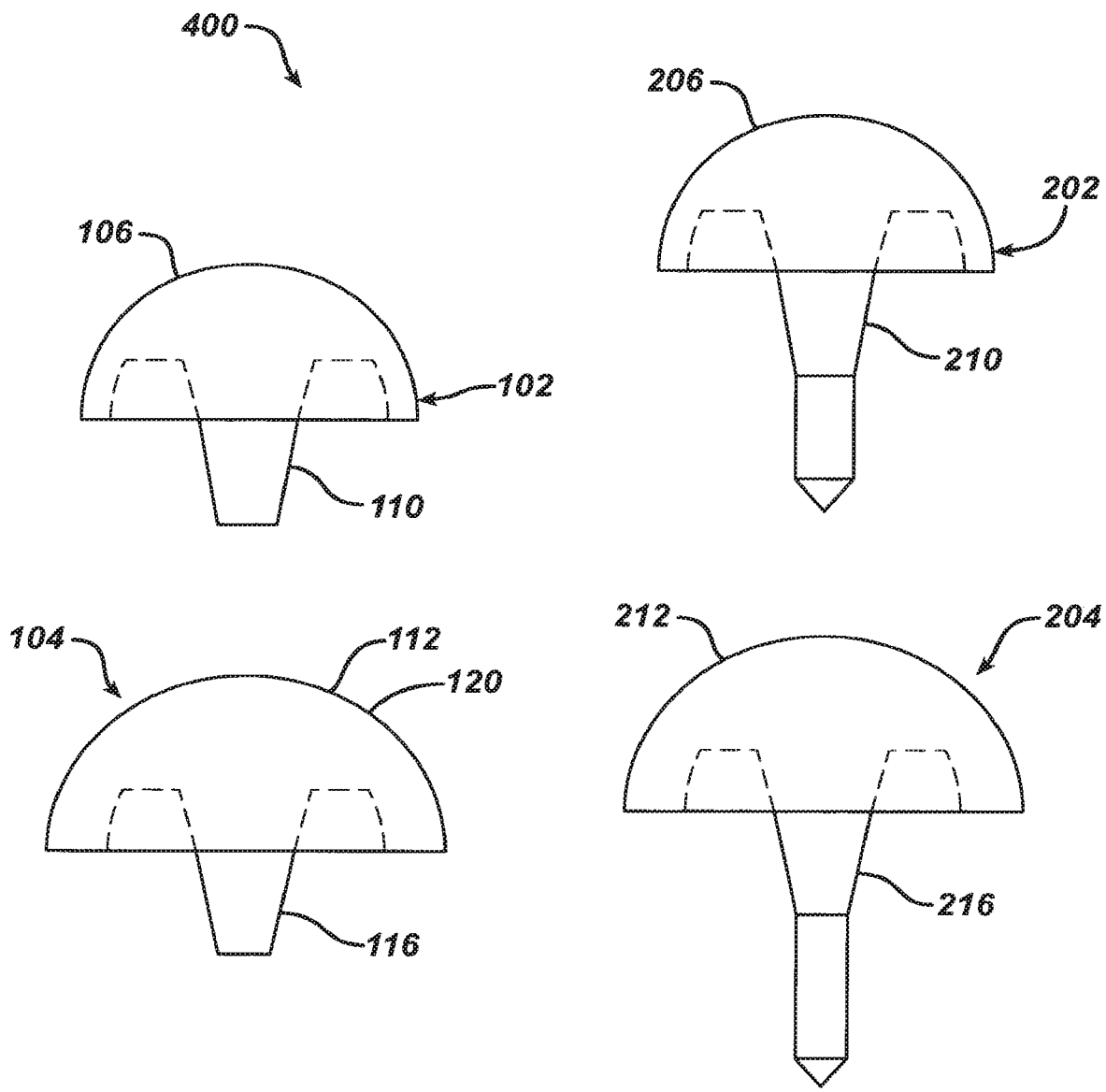
FIG. 7A is a plan view of a trial and implant kit according to another embodiment of the present invention for use in performing shoulder arthroplasty on a diseased humerus.

Referring now to FIG. 7A, another embodiment of the present invention is shown as trial and implant kit 400. As shown in FIG. 7A, the kit 400 includes the first trial 102, the second trial 104, the first implant 202 and the second implant 204. The first trial 102 has articulating surface 106 that is substantially smaller than articulating surface 112 of the second trial 104. The locating feature 110 of the first trial and the locating feature 116 of the second trial 104 are substantially similar in size and shape. Therefore, the first trial 102 and the second trial 104 can both be placed into the same prepared cavity of a head of, for example, a humerus.

Similarly, the first implant 202 has an articulating surface 206 that is substantially smaller than articulating surface 212 of the second implant 204. The first implant 202 has a locating feature 210 that is substantially the same in size and shape as location feature 216 of the second implant 204. It should be appreciated that the location features 110, 116, 210 and 216 are all of substantially the same size and shape. The articulating surface 106 of the first trial 102 corresponds to articulating surface 206 of the first implant 202 and similarly the articulating surface 112 of the second trial 104 corresponds to the articulating surface 212 of the second implant 204.

It should be appreciated that using the trial and implant kit 400 of the present invention provides for the ability to switch from a first trial to a second trial without affecting the fit of the trial to the cavity formed in the head of the humerus. Therefore, a surgeon in the operating room can freely pick from a range of trials without a need to re-ream or to fit bone graft around a cavity to change from a larger to a smaller trial.

Figure 8:
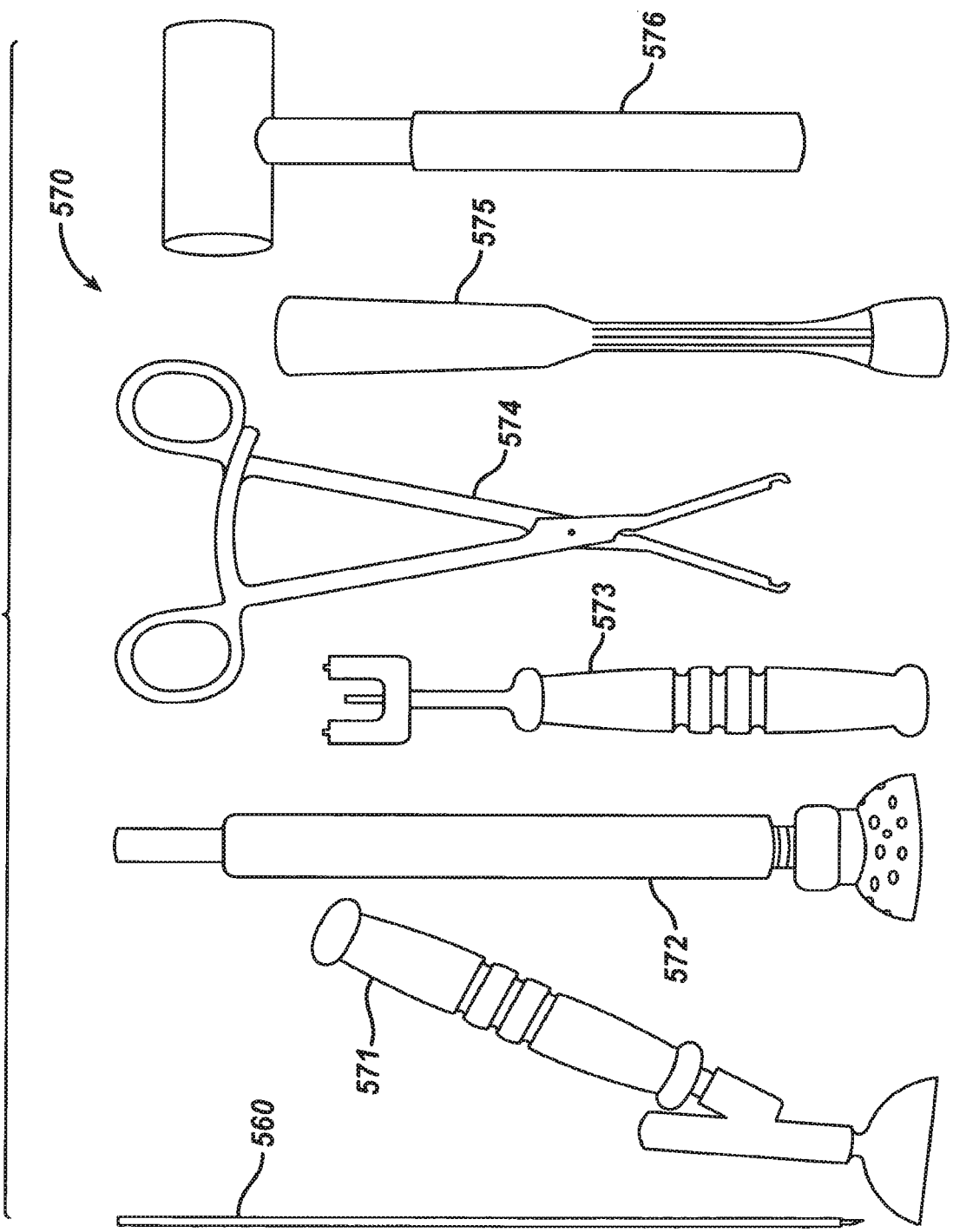
FIG. 8 is a plan view of a set of instruments for use with the trial set and implant set of the present invention.

Referring now to FIG. 8, a kit 570 for use when performing an arthroplasty to implant the prosthesis of the present invention is shown. The kit 570 includes the guide pin 560 and a guide pin alignment tool 571 for assisting in aligning the guide pin and positioning it into the humerus. The instrument kit 570 also includes a cutting tool assembly 572 for preparing the humeral head. The instrument kit 570 further includes a cutting tool assembly wrench 573 for assembling and disassembling the cutting tool from the cutting tool assembly 572. The instrument kit 570 also includes forceps 574 for securely gripping items. The instrument kit 570 also includes a humeral head impactor 575 that is used with a surgical mallet 576 to drive the implant into its final seat.

Figure 9:
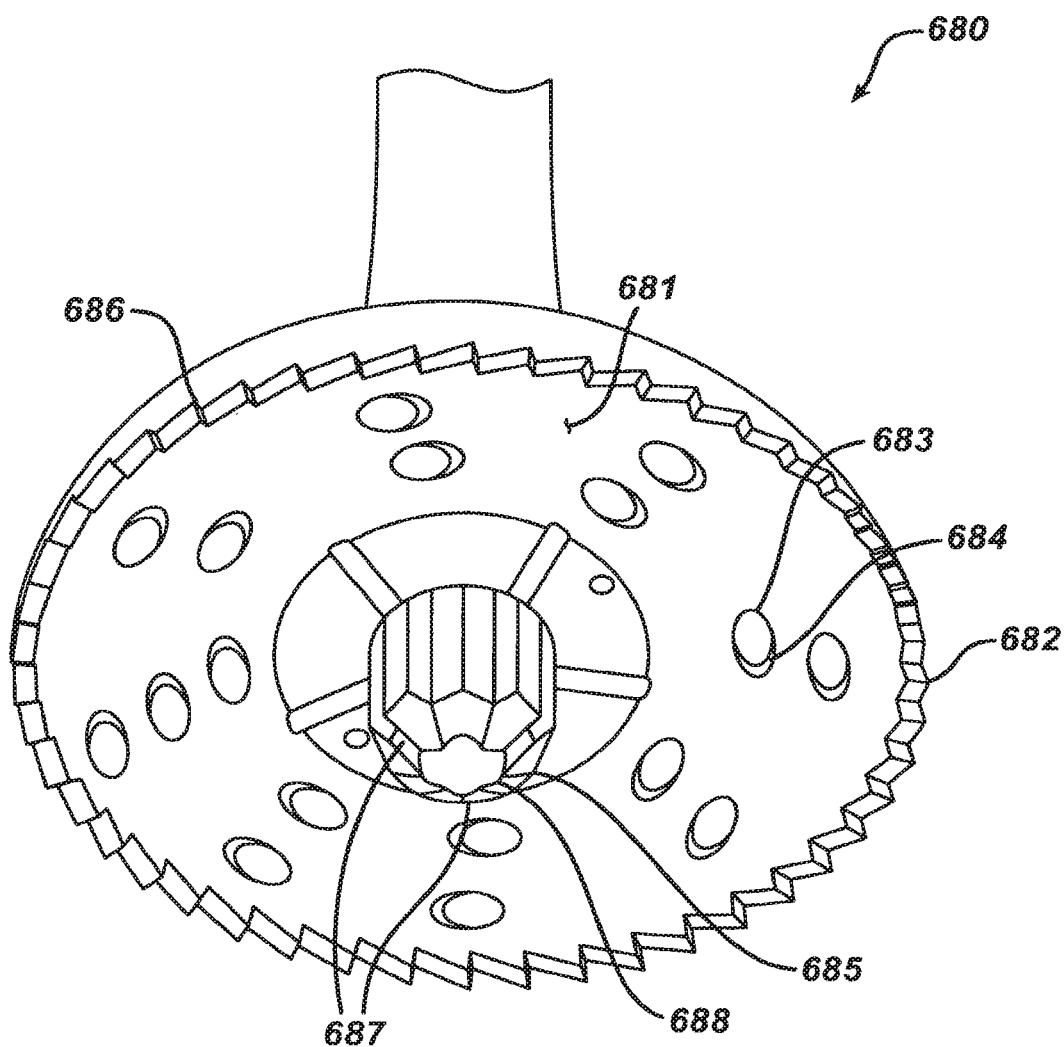
FIG. 9 is a perspective view of a reamer for use in preparing a humerus to receive the trials and implants of the present invention.
Figure 10:
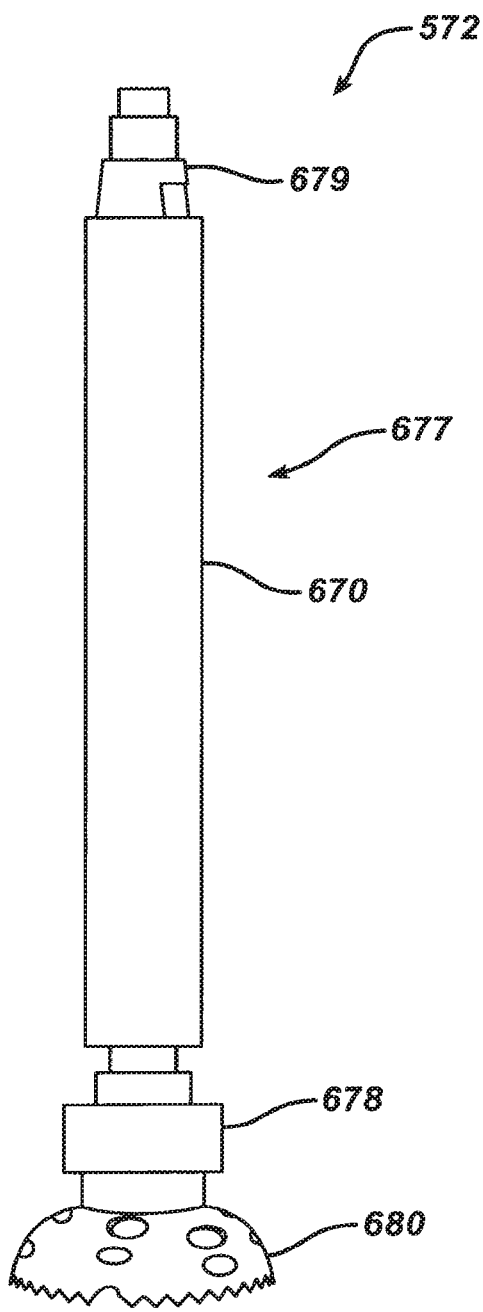
FIG. 10 is a plan view of a reamer assembly for use with the reamer of FIG. 9.

Referring now to FIG. 9, the humeral head configurations required for use with the trials and implants found in FIGS. 1 and 5, may be formed in one step by utilizing the cutting tool assembly 572 of FIG. 10 with a combination cutting tool or reamer 680 as shown in FIG. 9. Applicants have found that the cutting tool or reamer 680 may be provided which simultaneously provides the hemispherical shape, the central opening for the stem of the prosthesis, a counter bore, as well as a planar surface. This cutting tool or reamer 680 includes a hemispherical body 681. The hemispherical body 681 is hollow, including a plurality of openings 683 leaving cutting edges 684 on the edge of the openings 683 for removing the material necessary to form the hemispherical shape on the humerus. The cutting tool or reamer 680 also includes a cylindrical reamer 685 for preparing the humerus for receiving a trial prosthesis. The reamer or cutting tool 680 may also include a series of circumferential saw teeth 686 located on the outer periphery of the body 682. The cylindrical reamer 685 may include a counter bore area 687 to provide a counter bore for the stem of the trial. Further, the cutting tool or reamer 680 may include a central opening 688 for receiving a guide pin to stabilize the reamer during cutting and assure its proper position.

Referring now to FIG. 10, the cutting tool assembly 572 is shown in greater detail. The cutting tool assembly 572 includes a tool holder 677 to which the cutting tool 680 in the form of, for example, a hemispherically shaped reamer is attached. The tool holder 677 includes a drive adapter 679 for attaching a power device (not shown) to the cutting tool assembly 572. The tool holder 677 further includes a tool holder adapter 678 for securing the cutting tool 680 to the tool holder 677.

Figure 11:
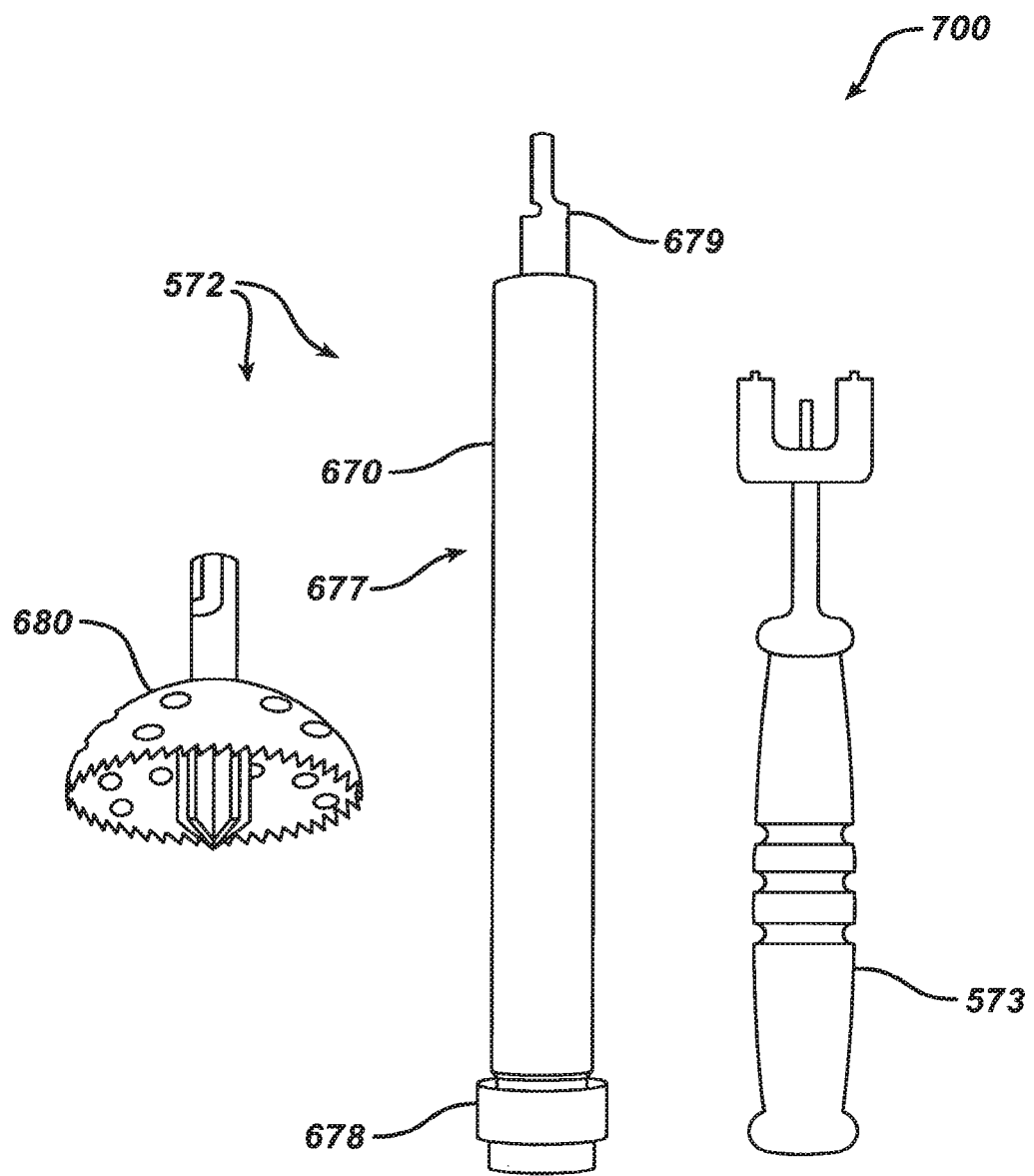
FIG. 11 is a plan and perspective view a tool kit including the reamer assembly of FIG. 10 shown disassembled as well as a plan view of an assembly tool used to install the cutting reamer onto the reamer handle.

Referring now to FIG. 11, a cutting tool assembly kit 700 is used with the trial and implant kit and surgical method of the present invention. The cutting tool assembly kit 700 includes the tool holder 677, a cutting tool in the form of reamer 680 and the cutting tool assembly wrench 573. The tool holder 677 includes a body 670 and the tool holder adapter 678 located on one end of the body 670. A rotational sleeve 699 fits over body 670 for grasping by the surgeon. The tool holder adapter 678 is utilized to secure the reamer 680. The tool holder 677 further includes a driver adapter 679 located on the opposite end of the body 670. The driver adapter 679 is utilized to secure the tool holder 677 to a power source (not shown). The tool holder 677 and the reamer 680 combine to form the cutting tool assembly 572.

Figure 12:
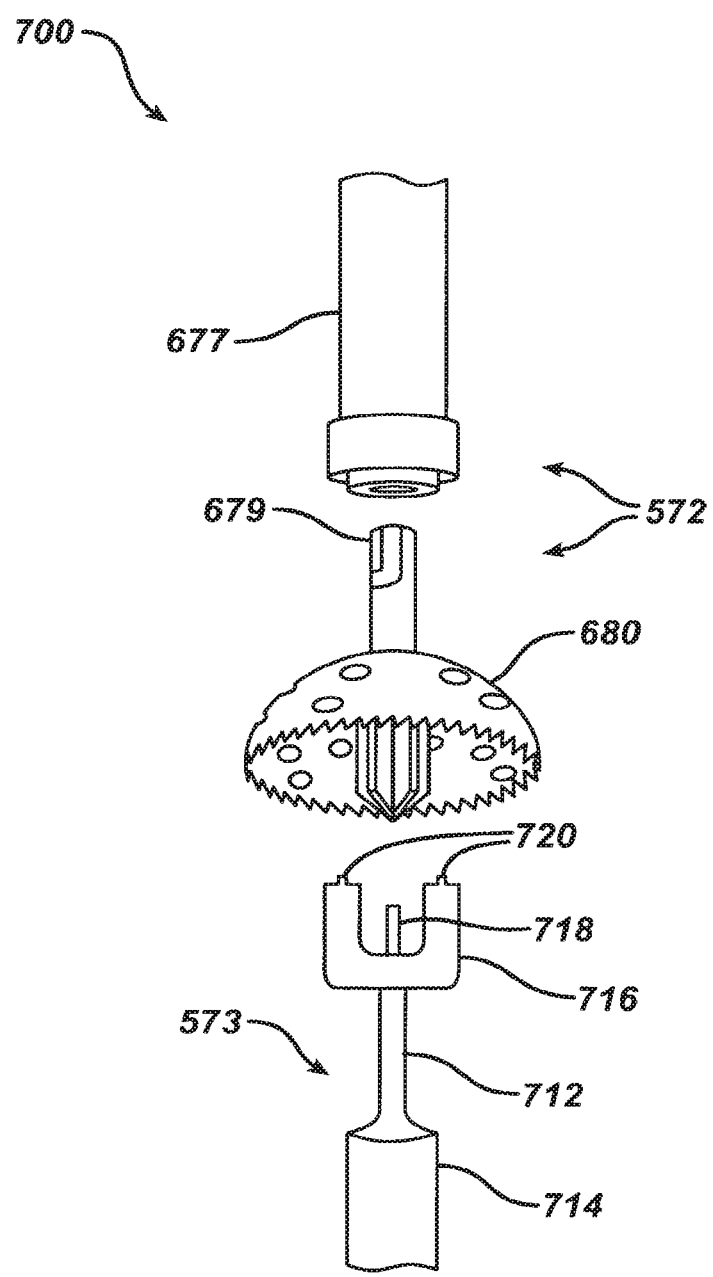
FIG. 12 is an exploded perspective view of the tool kit of FIG. 11.

Referring now to FIG. 12, the cutting tool assembly wrench 573 is shown in greater detail. The wrench 573 includes a body 712. At a first end of the body 712 is a handle 714 for securing and rotating the wrench 573. At the opposed end of the body 712 is a fork 716. Extending centrally from the fork 716 is a guide pin 718 for engagement with the cutting tool 680 to orient the wrench 573 with respect to the cutting tool 680. The fork 716 further includes a pair of drive engagement pins 720. The drive engagement pins are utilized to cooperate with the cutting tool 680 to transfer torque from the wrench 573 to the cutting tool 680.

Figure 12A:
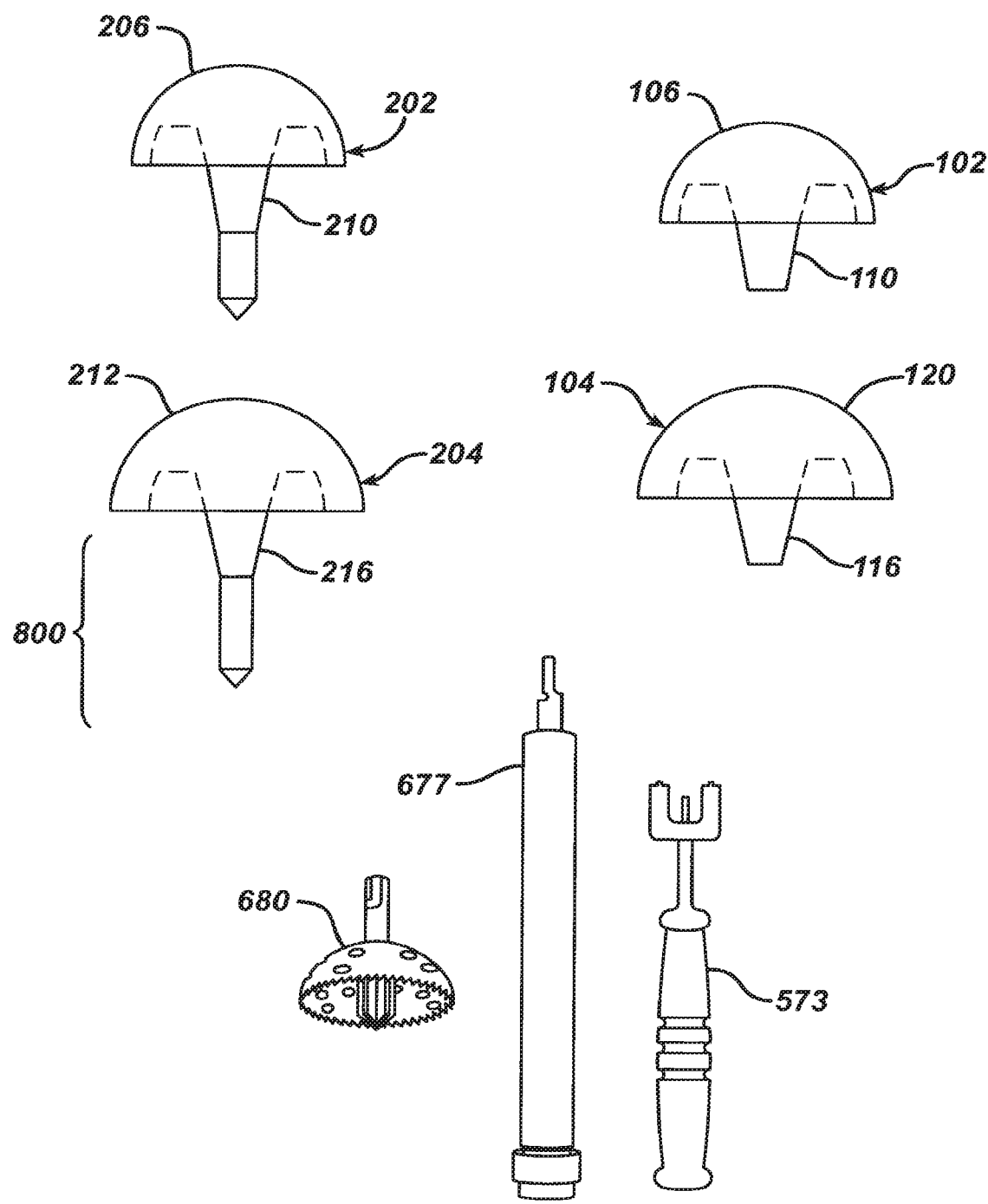
FIG. 12A is a plan and perspective view of another embodiment of a trial and implant kit including instruments according to the present invention for use in performing shoulder arthroplasty on a diseased humerus.

Referring now to FIG. 12A, another embodiment of the present invention is shown as trial implant and tool kit 800. The kit 800 includes the first trial 102 and the second trial 104. The kit 800 further includes the first implant 202 and the second implant 204. The kit 800 also includes the tool holder 677 and the cutting tool 680. The kit 800 further includes the wrench 573.

Referring now to FIG. 13, the cutting tool assembly 572 is shown in position with the cutting tool 680 in engagement with the head 5 of humerus 4. The tool holder 677 includes the drive adapter 679, which is engageable with a power source (not shown), and an adapter 678. The cutting tool 680 is secured by the adapter 678 to the tool holder 677.

Referring now to FIG. 14, another embodiment of the present invention is shown as method 900. Method 900 includes the first step 902 of providing an instrument for repairing a surface on a long bone. The method 900 also includes the second step 904 of a providing a plurality of trials, each of the trials being adapted to mate with the surface. The method 900 also includes the third step 906 of selecting one of a plurality of trials and the fourth step 908 of performing a trial reduction on one of the plurality of trials. The method 900 also includes a fifth step 910 of determining if one of the plurality of trials is satisfactory. The method 900 also includes the sixth step 912 of performing additional trial reductions as required and the seventh step 914 of selecting one of the plurality of joint prostheses corresponding to one of the plurality of trials based upon the trial reductions. The method 900 further includes the eighth step 916 of implanting the selected one prosthesis into the long bone.

Figure 15:
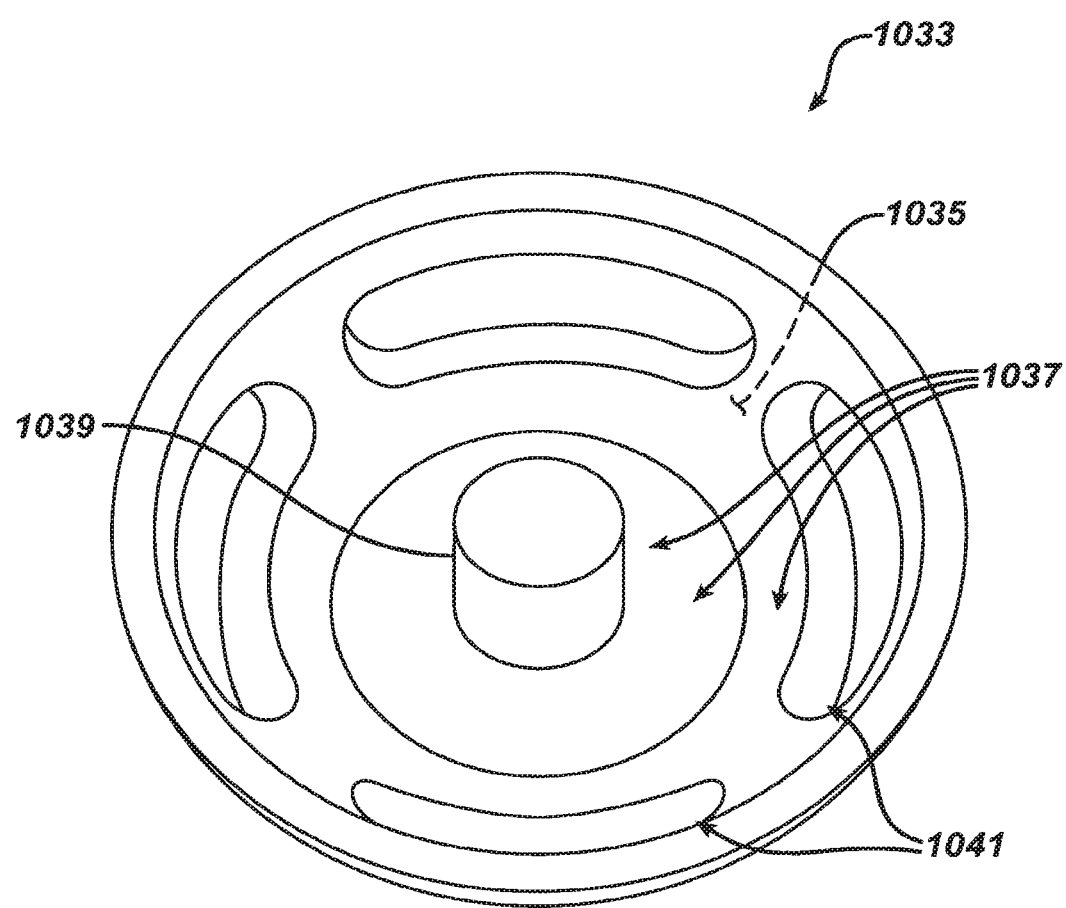
FIG. 15 is a perspective view of a trial according to an embodiment of the present invention.

Referring now to FIG. 15, a trial 1033 for use with the gauge and surgical method of the present invention is shown. A trial 1033 is utilized during shoulder arthroplasty to verify the proper selection of the prosthetic member by implanting the trial 1033 into the humeral head and performing trial reductions on the arm to verify the selection of the particularly sized trial and corresponding prosthesis.

The trial 1033 may be removed and replaced with the corresponding prosthesis. The trial 1033 may be reused after sterilization. The trial 1033 may therefore be made of any suitable durable material and may, for example, be made of a durable plastic that may be sterilized by standard sterilization methods, such as an autoclave.

Figure 17:
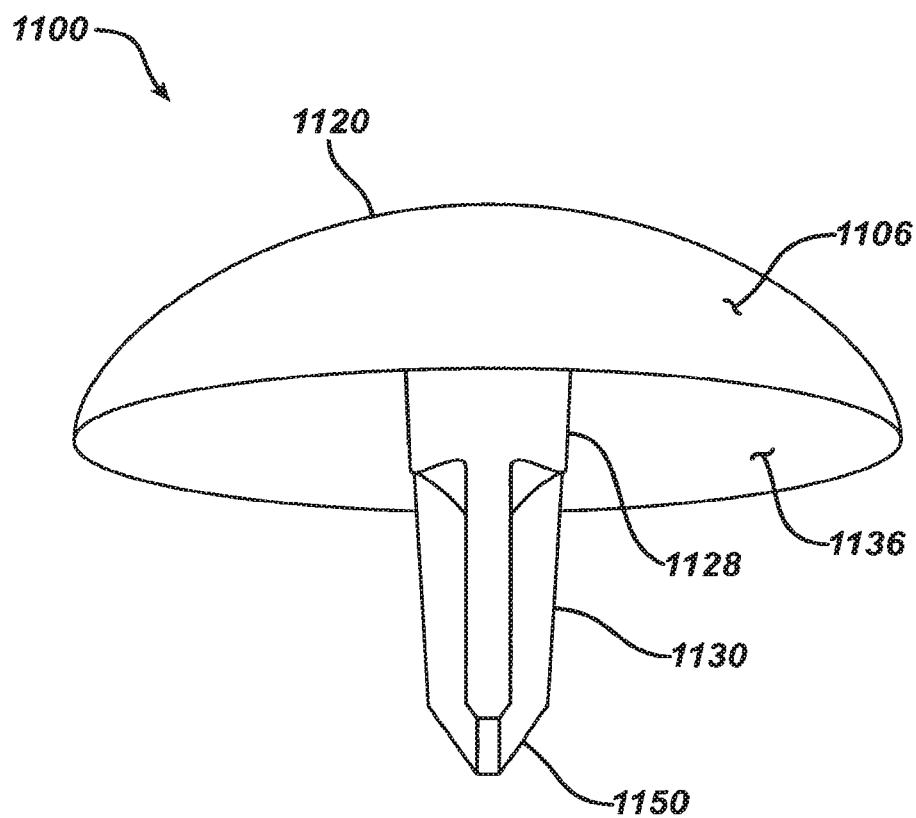
FIG. 17 is another perspective view of the implant of FIG. 16.

The trial 1033 mimics the size and shape of the prosthesis. The trial 1033 therefore includes an articulating surface 1035 and an opposed support surface 1037. The trial 1033 further includes a stem 1039 extending outwardly from the support surface 1037. As shown in FIG. 17, the trial 1033 may also include a plurality of spaced-apart openings 1041 to grasp with a tool (not shown) in the removal of the trial 1033. The openings 1041 also serve to provide viewing of the support surface and the humerus 4 to visually assure the proper seating of the trial.

Figure 16:
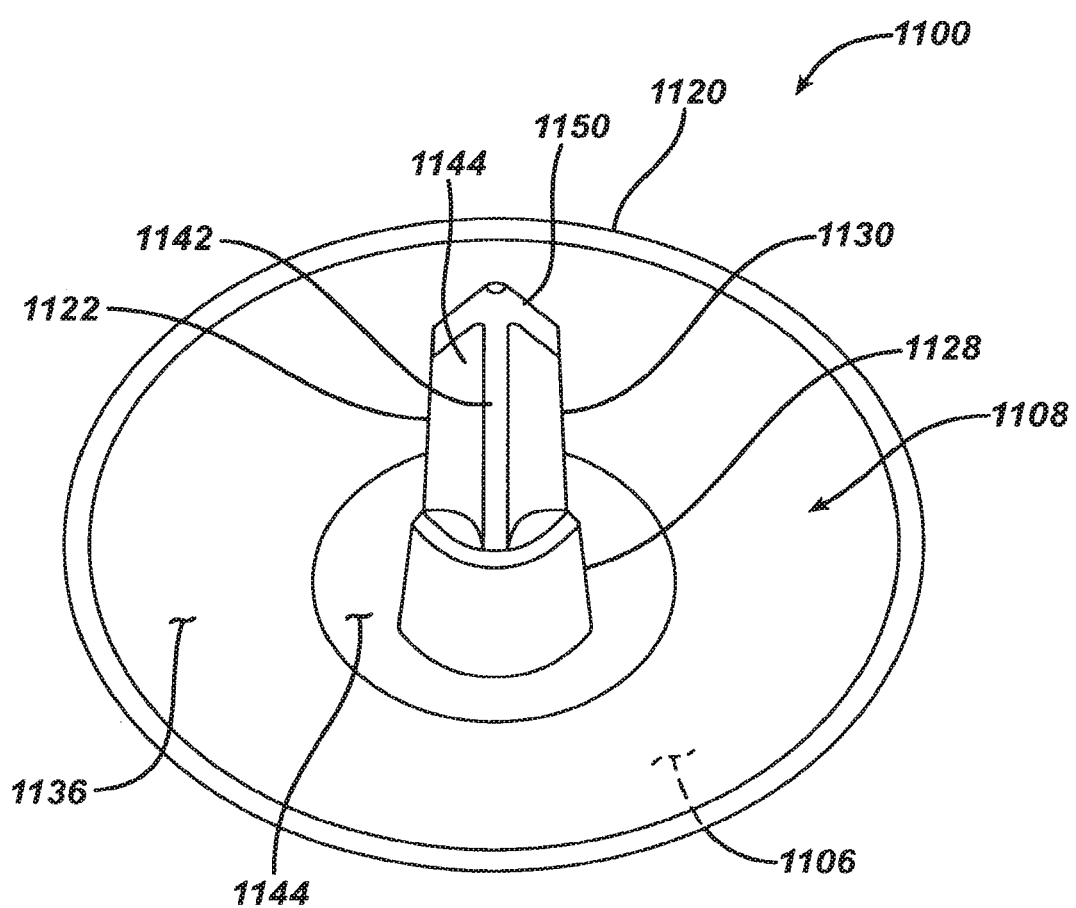
FIG. 16 is a perspective view of an implant according to an embodiment of the present invention.

Referring now to FIGS. 16 and 17, an implant 1100 is shown which may be used with the tool kit, implant kit and method of the present invention. The implant 1100 is similar to the first implant 202 of FIG. 5. The implant 1100 may include a body 1120. The body 1120 may be in the form of a hollow hemisphere. The body 1120 may include an articulating surface 1106. The articulating surface 1106 may be arcuate and in particular may be convex and have a generally hemispherical shape. The body 1120 may further include a mounting surface 1108 opposed to the articulating surface 1106. The implant 1100 may further include a stem 1122 extending from the mounting surface 1108 of the body 1120. The mounting surface 1108 of the implant 1100 may include a planar portion 1144 and a concave portion 1136.

The stem 1122 may include a positioning portion 1128 adjacent the planar portion 1144 of the mounting surface 1108. The positioning portion 1128 may be generally conifrustrical. The stem 1122 may further include a securing portion 1130 extending from the positioning portion 1128 of the stem 1122. The securing portion 1130 may include a plurality of spaced apart lands 1142. Each of the lands 1142 may be separated by recesses 1144. The stem 1122 may further include a nose 1150 extending outwardly from the securing portion 1130.

The nose 1150 and the lands 1142 and the recesses 1144 of the securing portion 1130 serve to reduce the force necessary to implant the implant 1100. Further, the lands 1142 and the recesses 1144 serve to provide rotational stability for the implant 1100.

Figure 18:
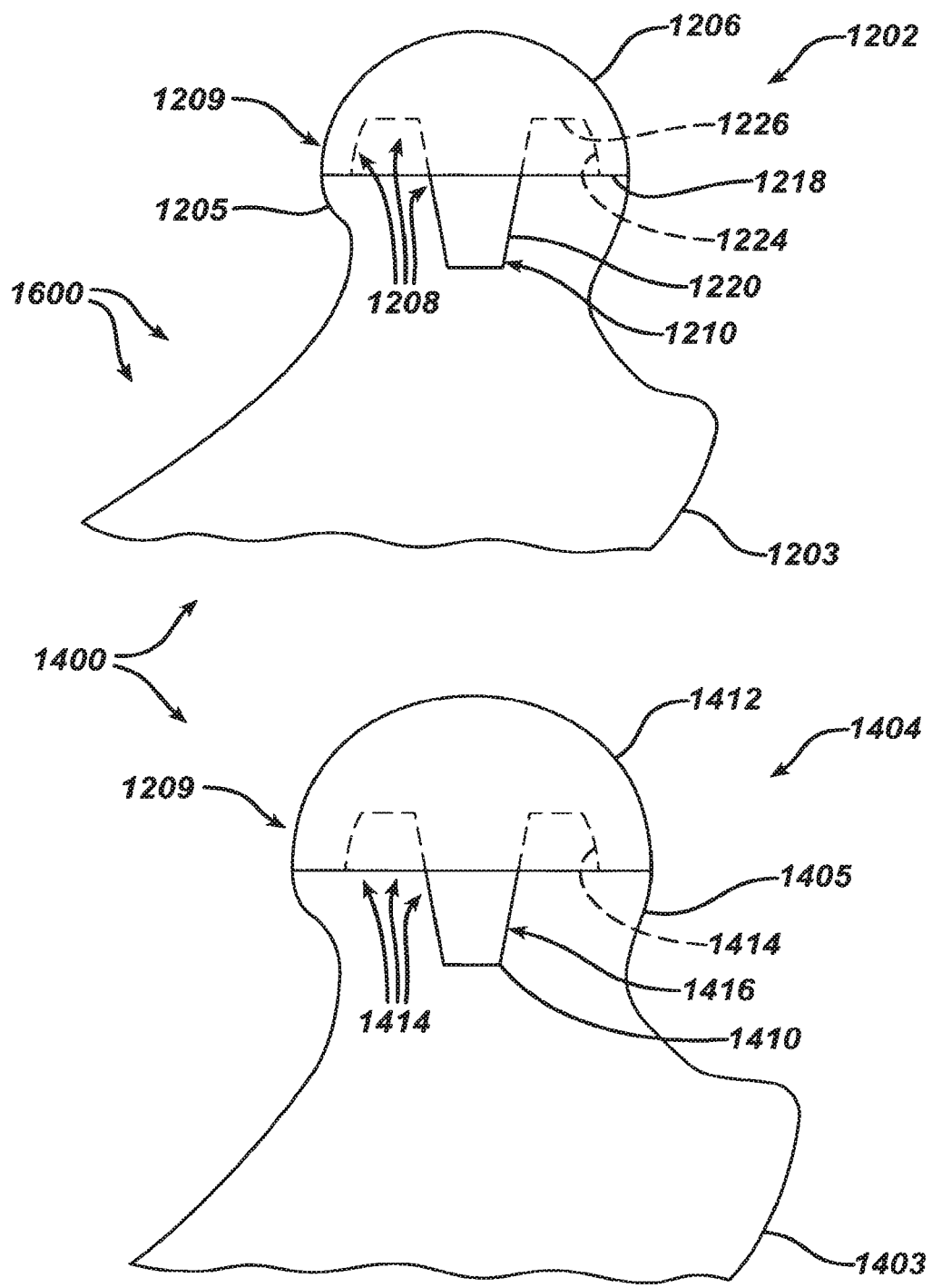
FIG. 18 is a plan view of a trial and a trial set for use with femurs according to another embodiment of the present invention.

Referring now to FIG. 18, another embodiment of the present invention is shown as trial 1202 for use with a femur 1203. The trial 1202 is similar to trial 102 of FIG. 1, but is designed for use with femur 1203. For example, and as shown in FIG. 18, the trial may include a body 1218 and a stem 1220 extending from the body 1218. The body 1218 includes articulating surface 1206.

As shown in FIG. 18, the stem 1220 serves as a location feature and fits into a prepared cavity 1209 in the femur 1203. The stem 1220 includes location feature 1210. The stem may have any suitable shape and may, for example, be in the form of a tapered protrusion, for example, in the form of a truncated cone or a tapered cylinder. The trial 1202 also includes a mounting surface 1208. The mounting surface 1208 may be identical to the mounting surface 108 of the trial 102 of FIG. 1. As shown in FIG. 18, the mounting surface 1208 includes a concave portion 1224 and a planar portion 1226. The planar portion 1226 corresponds with the resected portion of the femur 1205 to accommodate the flattened head resulting from osteoarthritis.

Figure 19:
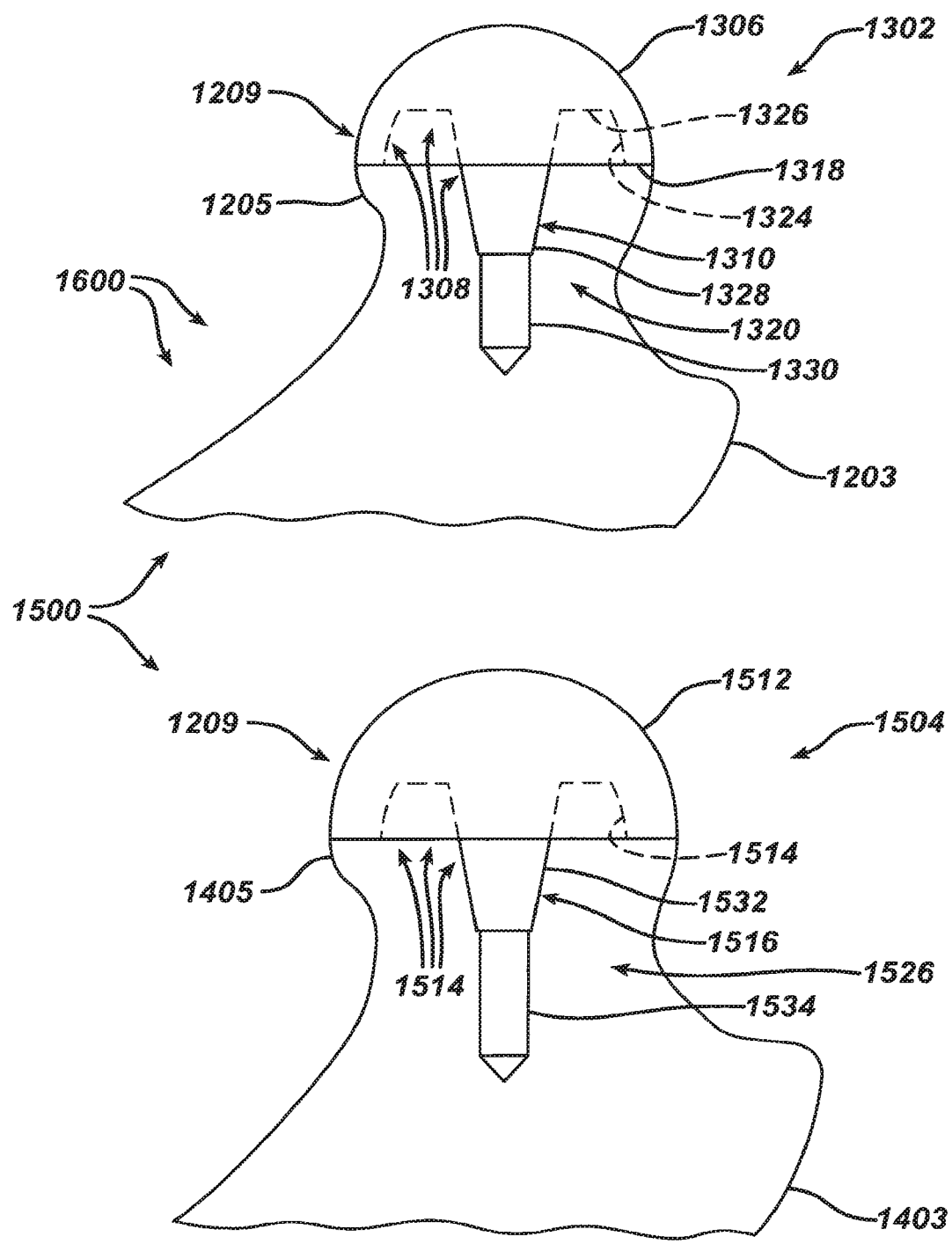
FIG. 19 is a plan view of an implant and an implant set for use with femurs according to another embodiment of the present invention.

Referring now to FIG. 19, another embodiment of the present invention is shown as implant 1302 for use with femur 1203. The implant 1302 is similar to implant 202 of FIG. 5, but is designed for use with femur 1203. For example and as shown in FIG. 19, the implant may include a body 1318 and a stem 1320 extending from the body 1318. The body 1318 includes articulating surface 1306.

As shown in FIG. 19, the stem 1320 serves as a location feature and fits into a prepared cavity 1209 in the femur 1203. The stem 1320 includes location feature 1310. The stem 1320 may have any suitable shape and may, for example, be in the form of a tapered protrusion, for example, in the form of a truncated cone or a tapered cylinder. The implant 1302 also includes a mounting surface 1308. The mounting surface 1308 may be identical to the mounting surface 208 of the implant 202 of FIG. 5. As shown in FIG. 19, the mounting surface 1308 includes a concave portion 1324 and a planar portion 1326. The planar portion 1326 corresponds with the resected portion of the femur 1203 to accommodate the flattened head resulting from osteoarthritis.

Referring again to FIG. 18, another embodiment of the present invention is shown as trial kit 1400 for use with both femur 1203 and a larger femur 1403. The trial kit 1400 is used for performing joint arthroplasty on head 1205 of femur 1203 and on the head 1405 of femur 1403. The trial kit 1400 includes the first trial 1202 as well as a second trial 1404.

The second trial 1404 includes a second trial articulating surface 1412 and an opposed second trial mounting surface 1414. The second trial mounting surface 1414 includes a second trial location feature 1416. The first trial articulating surface 1206 and the second trial articulating surface 1412 have different geometries. The first trial location feature 1210 and the second trial location feature 1416 have substantially identical geometries. It should be appreciated that for the trial kit 1400, the mounting surfaces 1208 and 1414 of trials 1202 and 1404 may be similar to the mounting surface 108A of FIGURE A1 and not have a planar portion.

Referring again to FIG. 19, another embodiment of the present invention is shown as implant kit 1500 for use with femur 1203 and femur 1403. The implant kit 1500 is used for performing joint arthroplasty on heads 1205 and 1405 of femurs 1203 and 1403. The implant kit 1500 includes the first implant 1302 as well as a second implant 1504. The second implant 1504 includes a second implant articulating surface 1512 and an opposed second implant mounting surface 1514. The second implant mounting surface 1514 includes a second implant location feature 1516. The first implant articulating surface 1306 and the second implant articulating surface 1512 have different geometries. The first implant location feature 1310 and the second implant location feature 1516 have substantially identical geometries. It should be appreciated that for the implant kit 1500, the mounting surface 1308 and 1514 of implants 1302 and 1504 may be similar to the mounting surface 108A of FIGURE A1 and not have a planar portion.

For example, and as shown in FIG. 19, the stems 1320 and 1526 may include positioning portions 1328 and 1532, respectively, which have a generally tapered cylindrical shape and securing portions 1330 and 1534, respectively, which have a generally cylindrical shape and extend from the positioning portions 1328 and 1532.

Referring now to FIGS. 18 and 19, another embodiment of the present invention is shown as trial and implant kit 1600. As shown in FIGS. 18 and 19, the kit 1600 includes the first trial 1202, the second trial 1404, the first implant 1302 and the second implant 1504. The first trial 1202 has articulating surface 1206 that is substantially smaller than articulating surface 1412 of the second trial 1404. The locating feature 1210 of the first trial and the locating feature 1416 of the second trial 1404 are substantially similar in size and shape. Therefore, the first trial 1202 and the second trial 1404 can both be placed into the same prepared cavity of a head of the femur.

Similarly, the first implant 1302 has an articulating surface 1306 that is substantially smaller than the articulating surface 1512 of the second implant 1504. The first implant 1302 has a locating feature 1310 that is substantially the same in size and shape as the location feature 1516 of the second implant 1504. It should be appreciated that the location features 1210, 1416, 1310 and 1516 are all of substantially the same size and shape. The articulating surface 1206 of the first trial 1202 corresponds to articulating surface 1306 of the first implant 1302 and similarly the articulating surface 1412 of the second trial 1404 corresponds to the articulating surface 1512 of the second implant 1504.

It should be appreciated that using the trial and implant kit 1600 of the present invention provides for the ability to switch from a first trial to a second trial without affecting the fit of the trial to the cavity formed in the head of the humerus. Therefore, a surgeon in the operating room can freely pick from a range of trials without a need to re-ream or to fit bone graft around a cavity to change from a larger to a smaller trial.

Figure 20:
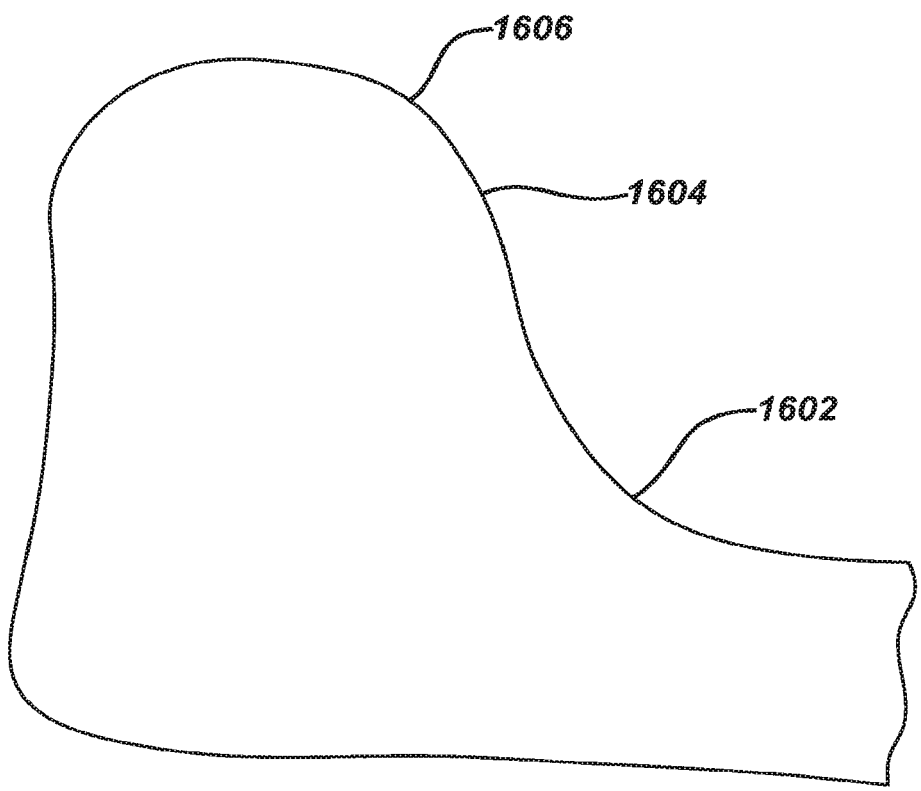
FIG. 20 is a partial plan view of a diseased femur.

Referring now to FIG. 20, a humerus 1602 is shown. The humerus 1602 includes a humeral head 1604 having an outer periphery 1606. The implant of the present invention is adapted to resurface the humeral head 1604 of the humerus 1602.

Figure 21:
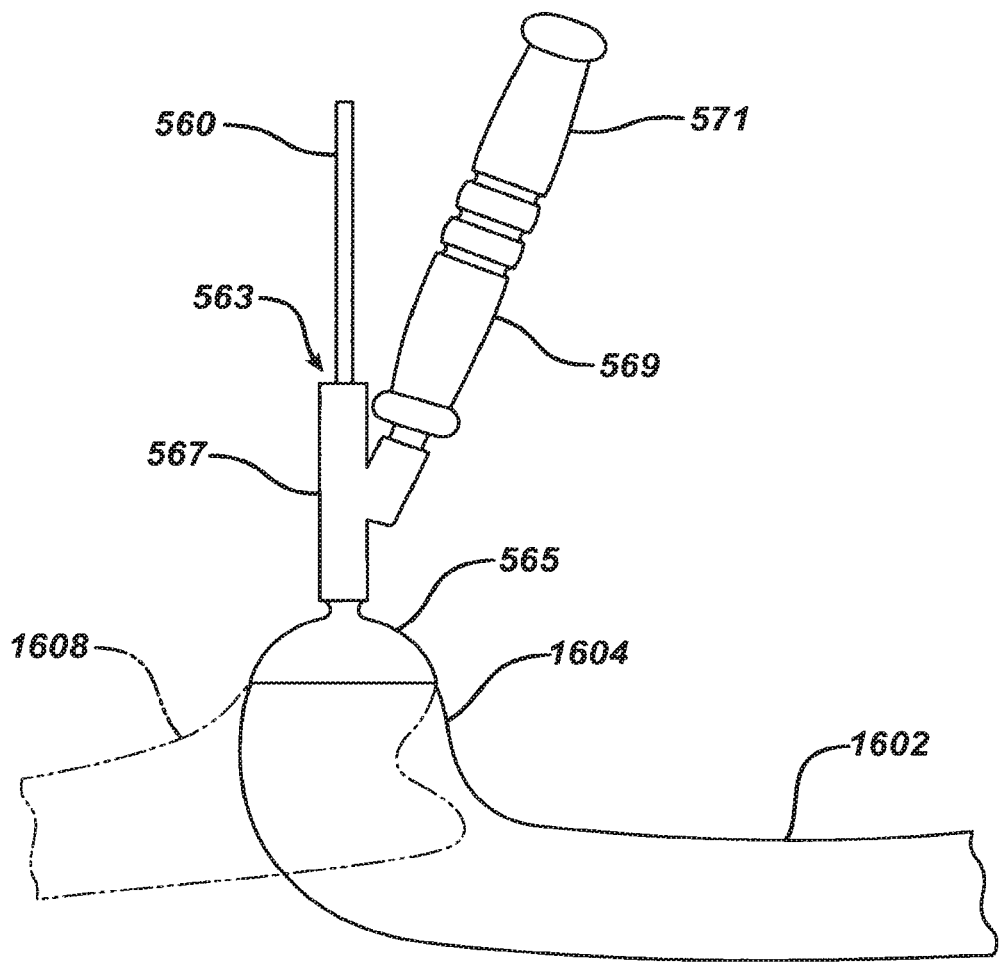
FIG. 21 is a partial plan view, partially in cross section of the guide pin alignment tool of FIG. 8 in position on the diseased humerus.

Referring now to FIG. 21, guide pin alignment tool 571 is shown in position on humeral head 1604 of the humerus 1602. The guide pin alignment tool 571 includes a body 567 having a hollow hemispherical portion 565. The tool 571 is manually moved about the periphery 1606 of the humeral head 1602 by handle 569 until the hollow hemispherical portion 565 is placed into the position where the implant should be placed. The body 567 of the alignment 571 includes a central opening 563 for receiving the guide pin 560. Once the alignment tool 571 is in the proper position, the guide pin 560 is inserted into the opening 563 and screwed into position in the humeral head 1604 of the humerus 1602.

It should be appreciated that the guide pin alignment tool 571 may be utilized with any long bone having a spherical head. For example, the guide pin alignment tool 571 maybe used with a femur, for example femur 1608 as shown in FIG. 21 in phantom.

Figure 22:
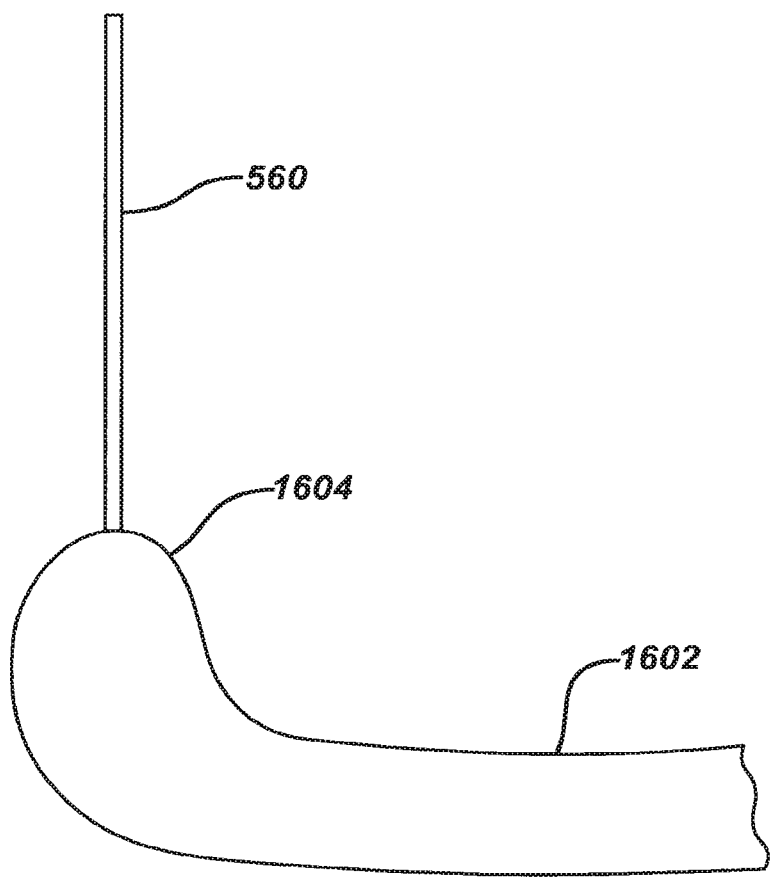
FIG. 22 is a partial plan view, partially in cross section of the guide pin of FIG. 8 in position on the diseased humerus.

Referring now to FIG. 22, the guide pin 560 is shown positioned in the humeral head 1604 of the humerus 1602.

Figure 23:
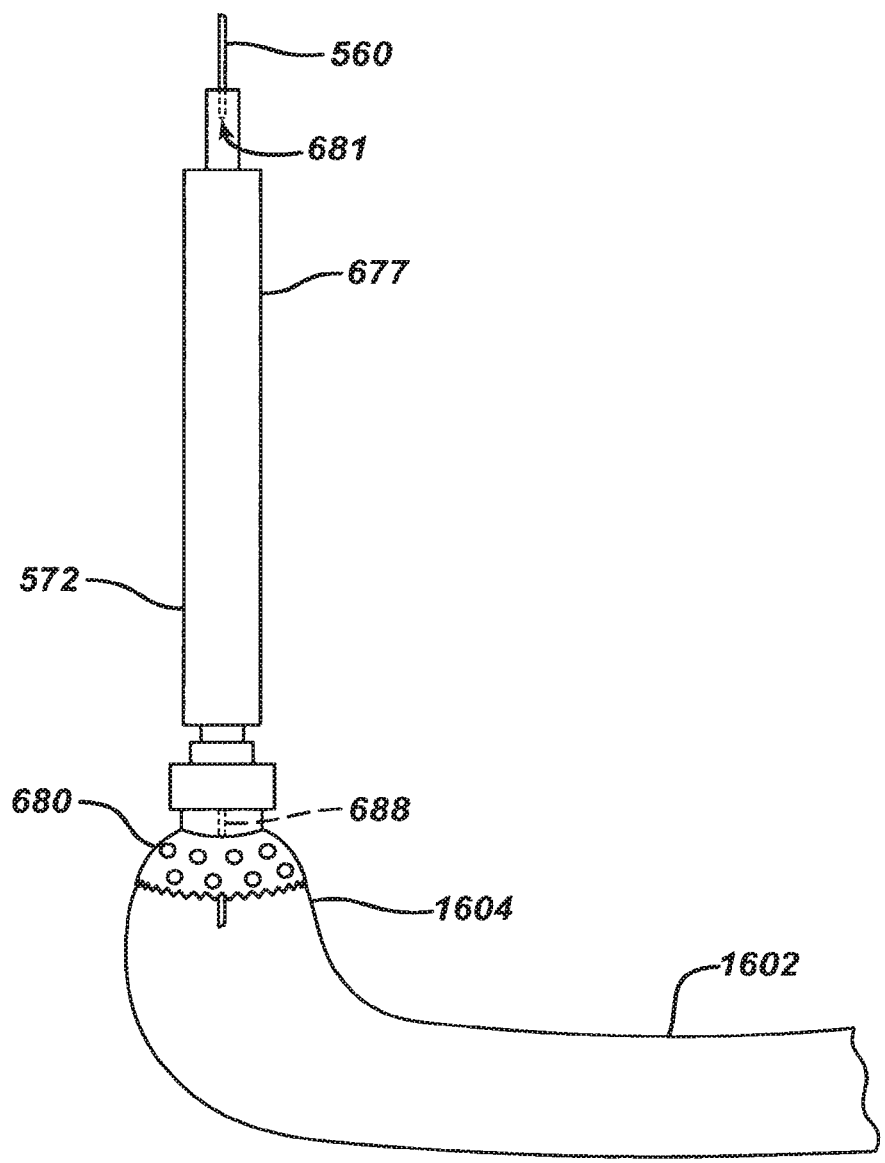
FIG. 23 is a partial plan view, partially in cross section of the cutter of FIG. 9 in position on the diseased humerus.

Referring now to FIG. 23, the combination cutting tool or reamer 680 is shown in position on the head 1604 of the humerus 1602. The reamer 680 is utilized to prepare the head 1604 for receiving the implant or prosthesis. The reamer 680 made for example, may be supported by a tool holder 677 which together with the reamer 680 forms the cutting tool assembly 572. The tool assembly 572 may fit over a guide pin 560 through a central opening 688 of the tool 680 as well as a central opening 681 in the tool holder 677. The guide pin 560 thus positions and steadies the reamer 680 to provide an accurate prepared surface for receiving the prosthesis in the desired position.

Figure 24:
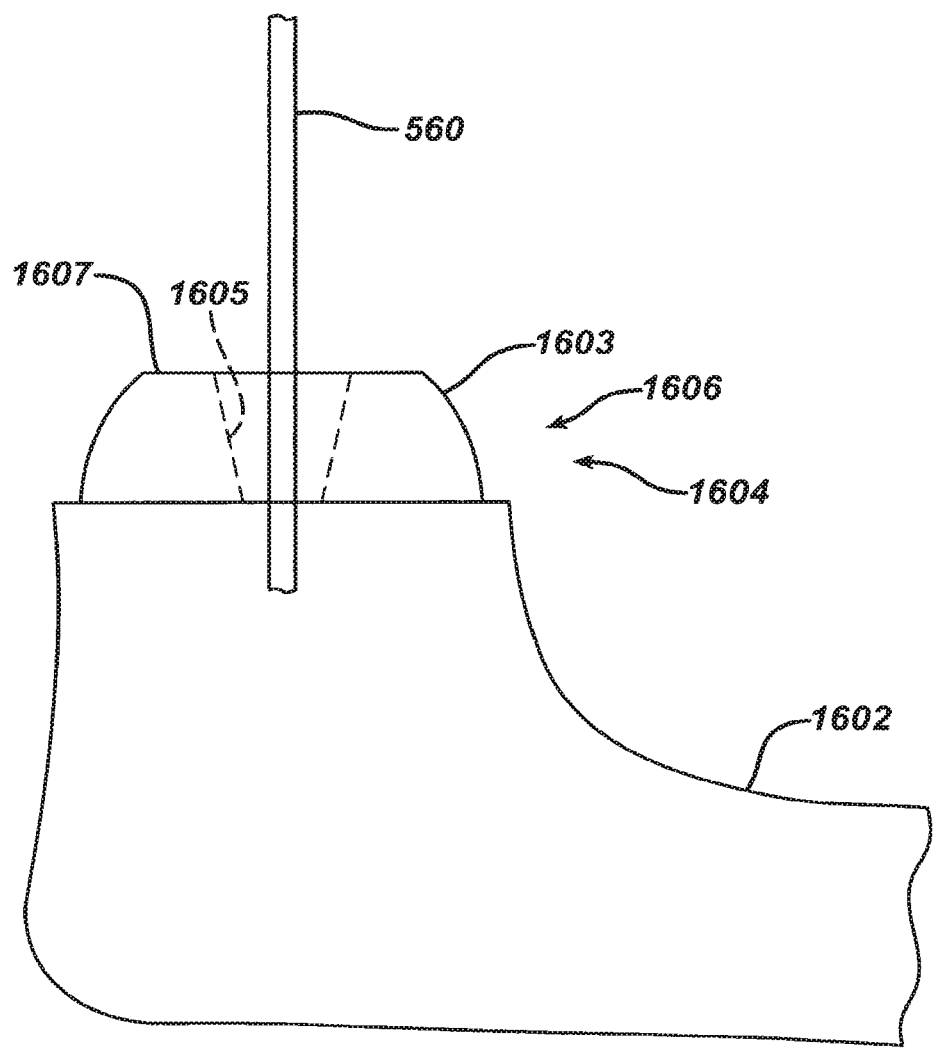
FIG. 24 is a partial plan view, partially in cross section of the humerus with a cavity prepared with the cutter of FIG. 9.

Referring now to FIG. 24, the humerus 1602 is shown with the prepared surface after being prepared by the reamer 680 of the FIG. 23. The periphery 1606 of the head 1604 of the humerus 1602, is prepared by the reamer 680 of FIG. 23 and includes a hemispherical convex surface 1603 and a tapered reamed pilot hole 1605 centrally positioned inside the hemispherical reamed convex surface 1603. Positioned between the hemispherical surface 1603 and the pilot hole 1605 is flat, milled, or planar surface of face 1607. As can be seen in FIG. 24, the guide pin 560 maybe centrally positioned about the head 1604.

Figure 25:
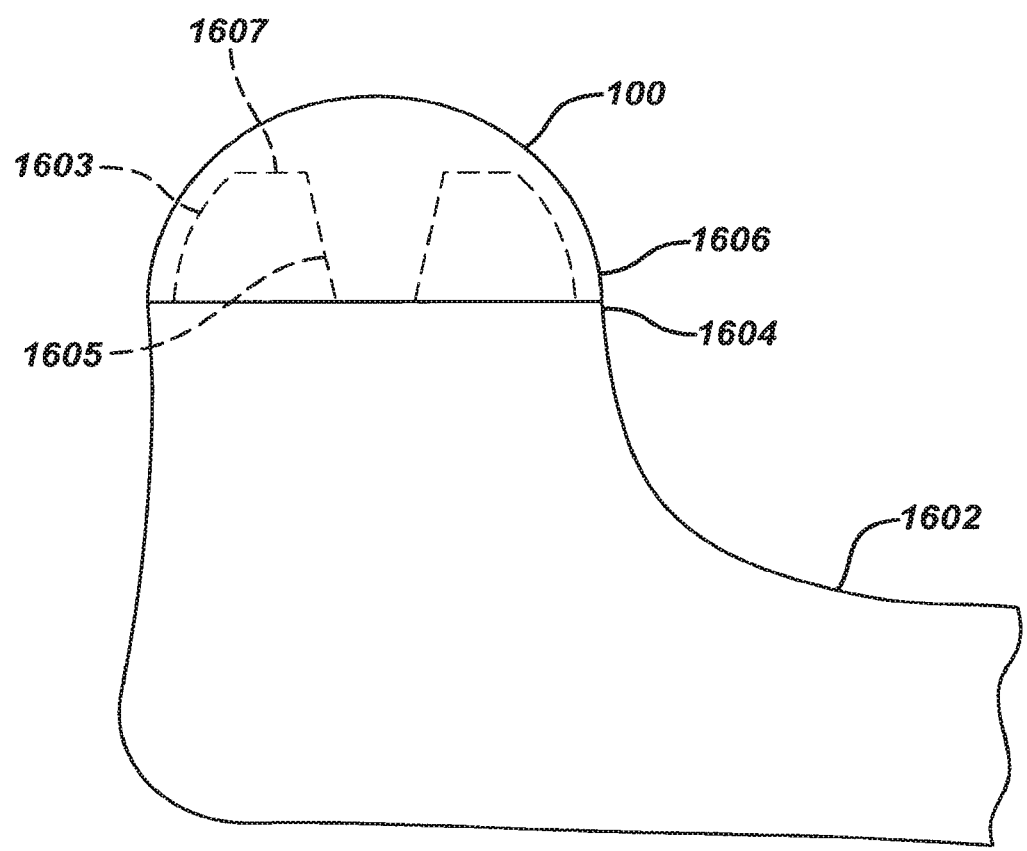
FIG. 25 is a partial plan view, partially in cross section of the trial of FIG. 15 in position on the humerus.

Referring now to FIG. 25, the trial 100 is shown positioned over periphery 1606 of the head 1604 of the humerus 1602. The trial 100 includes portions, which mate with the milled face or planar face 1607, the convex surface 1603, and the pilot hole 1605 of the periphery 1604 of the humerus 1602. As described earlier in this application, various trials having common interior surfaces can be placed on the periphery 1606 to accommodate a different range of motion and desired shoulder motion, each of the various trials to corresponding to one of various resulting implants.

Figure 26:
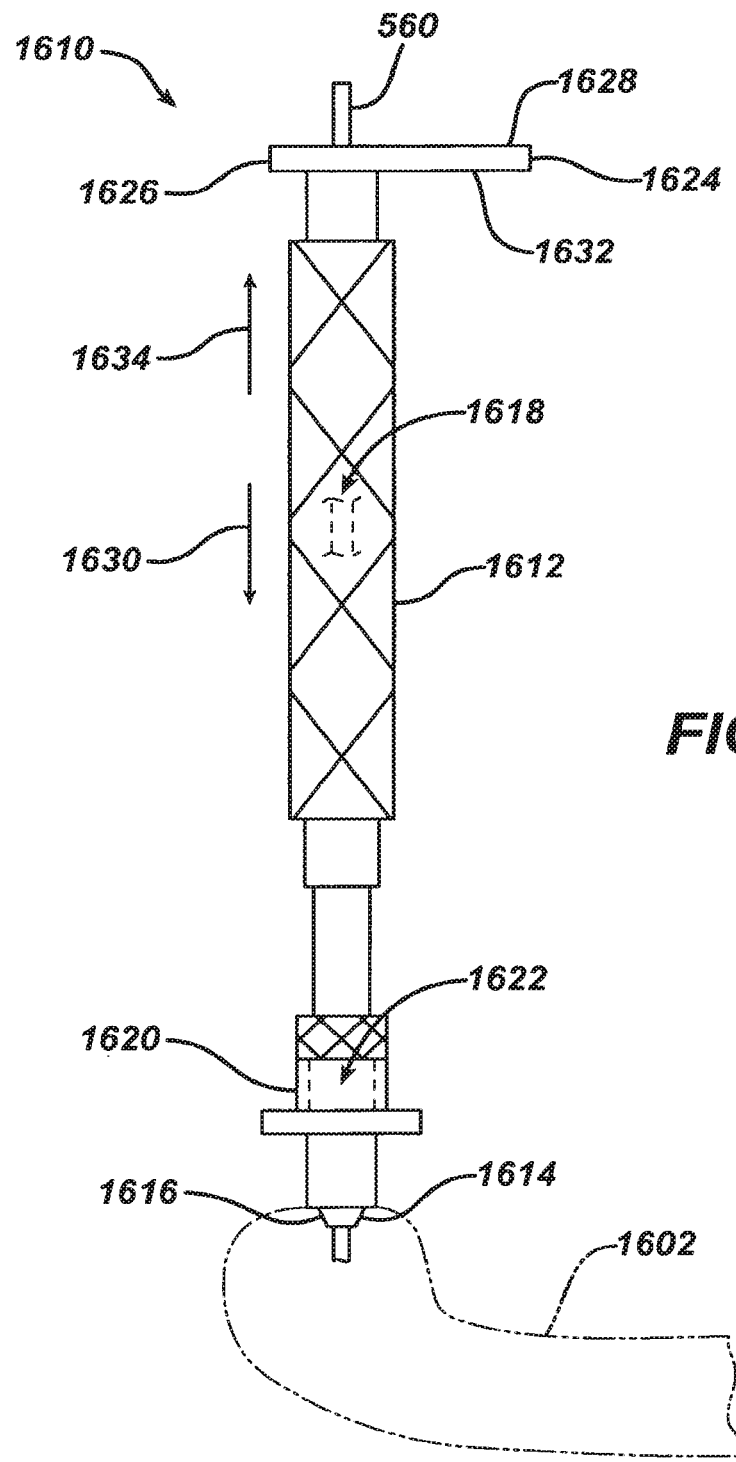
FIG. 26 is a plan view of a punch or impactor according to an embodiment of the present invention.

Referring now to FIG. 26, instrument 1610 according to present invention is shown. The instrument 1610 is utilized to prepare a cavity for a stem of a prosthetic implant for use in forming surface arthroplasty of a head of a long bone. The instrument 1610 includes a body 1612 and a punch 1614 extending from the body 1612. Punch 1614 includes a portion 1616 thereof, having a shape similar to the shape of the stem of the implant.

As shown in FIG. 26, the instrument 10 may further include a guide wire 560. The body 1612 of the instrument 1610 may include a central opening or aperture 1618 in the body 1612 for receiving the guide wire 560.

As shown in FIG. 26, the body 1612 and the punch 1614 may be integral with each other. Alternatively, the punch 1614 and body 1612 maybe made of separate components.

As shown in FIG. 26, the instrument 1610 also includes a stop 1620 for limiting the advancement of the portion 1616 of the punch 1614 into the long bone. The stop 1620 may have any suitable size and shape, for example and is shown in FIG. 26, the stop may define a longitudinal opening 1622 thru the stop 1620. The stop 1620 may be slidable along the punch 1614.

The instrument 1610 including the stop 1620, the punch 1614 and the body 1612 may each be made of any suitable, durable material, for an example a metal, a plastic material, or a composite material. Preferably the material is compatible with the human body. The instrument 1610 may, for example, be made of a metal, for example, a cobalt chromium alloy, a stainless steel alloy or a titanium alloy. Preferably the instrument 1610 is made of a material that may be sterilized by standard sterilization methods, such as autoclave.

To assist in securing, the instrument 1610 into the long bone 1602 and to assist in removing the instrument 1610 from the long bone 1602, the body 1612 of the instrument 1610 may include a feature 1624 for striking the instrument 1610, which will assist in inserting the instrument 1610. As shown in FIG. 26, the feature 1624 may be in the form of, for example, a generally planar plate extending outwardly from the body 1612 at the end 1626 of the body 1612. The feature 1624 may include an upper surface 1628 for striking with, for example, a hammer (not shown) in the direction of arrow 1630 for assisting in securing the implant. Similarly, the features 1624 may include a lower surface 1632 for striking in the direction of arrow 1634 for assisting in removing an implant.

It should be appreciated that alternatively the hammer may be in the form of a slap hammer or a cylindrical member (not shown) that has a central opening which is slidably fitted to the body 1612 of the instrument 1610 and restrained to the instrument at the ends of the body 1612. The outer periphery of the slap hammer is grabbed by the hand to strike the slap hammer.

Figure 27:
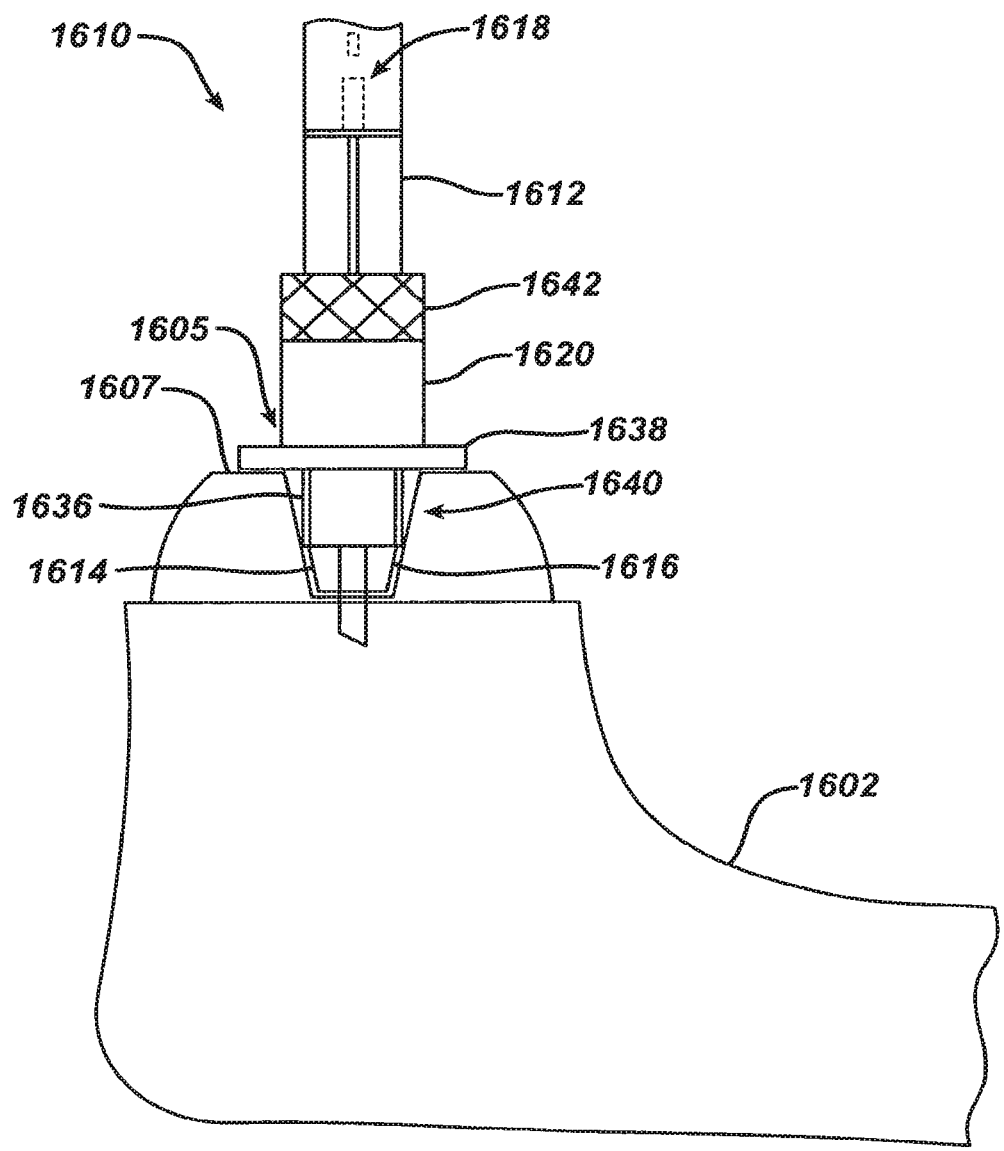
FIG. 27 is a partial plan view, partially in cross section, of the impactor of FIG. 26 in position on the humerus.

Referring now to FIG. 27, the instrument 1610 is shown in position, partially in pilot hole 1605 of long bone 1602. As shown in FIG. 27, the stop 1620 of the instrument 1610 includes a pilot 1636 extending downwardly from collar 1638 of the stop 1620. The pilot 1636 is preferably sized to mate with pilot hole 1605 and the collar 1638 is preferably designed to rest against planar face 1607 of the long bone 1602.

As shown in FIG. 27, the stop 1620 is shown in first position 1640 with the pilot 1636 of the stop 1620 seated against pilot hole 1605 of the humerus 1602 with the collar 1638 resting against planar face 1607 of the humerus 1602.

As shown in FIG. 27, the stop 1620 may include a surface 1642 in the form of, for example, a knurl. The knurl 1642 may assist in the moving, for example, the rotating of the stop 1620 relative to the body 1612 to orient the stop axially to permit its use in forming the hole for the implant.

Figure 27A:
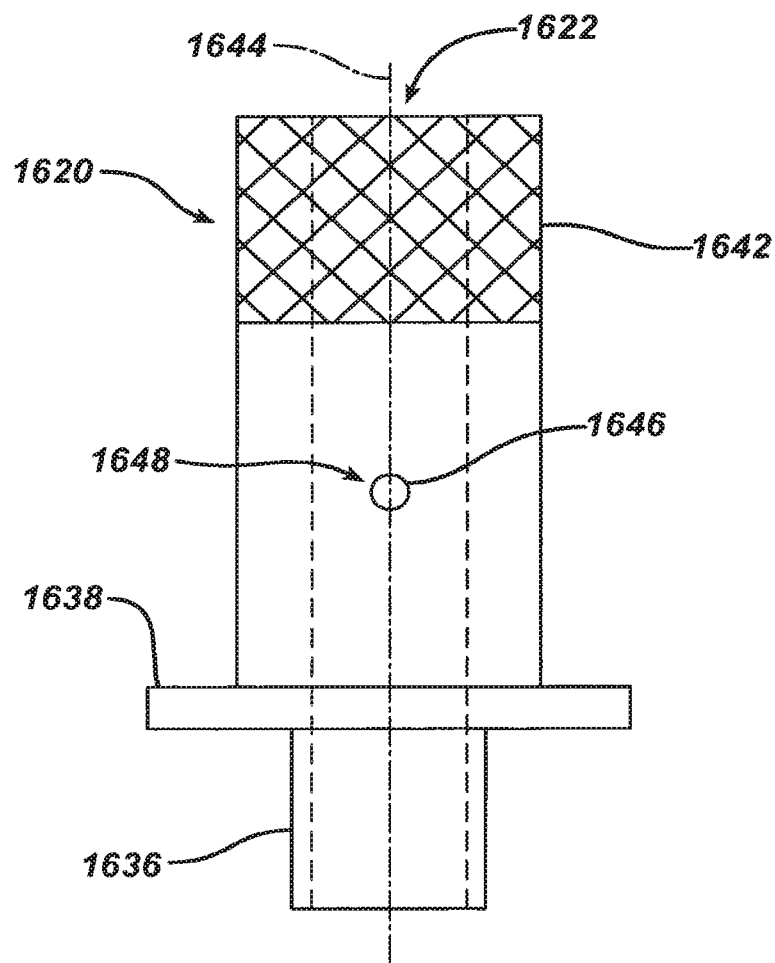
FIG. 27A is a partial plan view of the stop of the impactor of FIG. 27.

Referring now to FIG. 27A, the stop 1620 is shown in greater detail. The stop 1620 includes the central opening 1622 along which stop 1620 slides relative to the body 1612.

The stop 1620 preferably includes a feature for limiting the motion along longitudinal axis 1644 of the body of the 1612. For example and as is shown in FIG. 27A, the feature may be in the form of, for example, a pin 1646 which may protrude inwardly through the opening 1622 and cooperate with the body 1612 to limit the motion of the stop 1620 along longitudinal axis 1644. The pin 1646 may be a separate component that can be interferencely fitted in the opening 1648 or may be formed in the stop 1620.

Figure 27B:
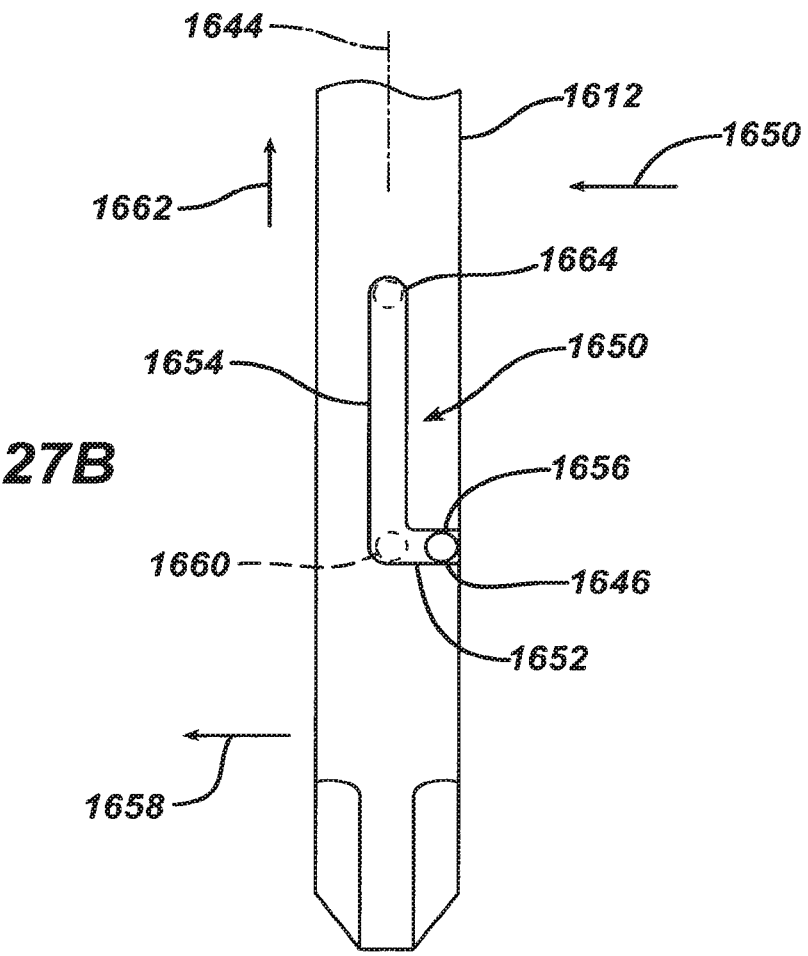
FIG. 27B is a partial plan view of the body of the impactor of FIG. 27.

Referring now to FIG. 27B, the body 1612 of the instrument 1610 is shown in greater detail. The body 1612 may include a feature 1650 which will cooperate with the feature, for example, opening 1648 of the stop 1620 for limiting motion of the stop 1620 along the body 1612 in the direction of longitudinal axis 1644. For example and is shown in FIG. 27B, the feature 1650 may be in the form of a J-channel. J-channel 1650 maybe in the form of a groove having a radial portion 1652 and a longitudinal portion 1654.

As shown in FIG. 27, the pilot 1636 of the stop 1620 is in first position 1640. The pin 1646 is in first pin position 1656 as shown in solid in FIG. 27B. When the stop is rotated in the direction in the arrow 1658, the pin 1646 may move from first position 1656 shown solid to second position 1660 as shown in phantom. When pin 1646 is in second position 1660, the stop 1620 may move in the direction of arrow 1662 permitting the pin to move to third position 1664 as shown phantom. When the pin 1646 is in the third position 1664, the punch 1614 may be utilized to form the recess for receiving the implant.

Figure 27C:
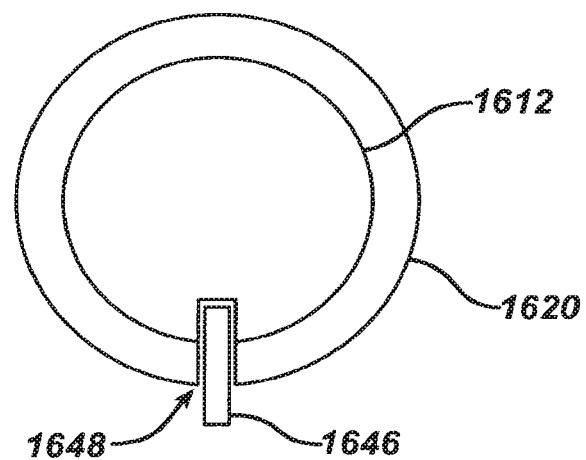
FIG. 27C is a partial plan view of the stop of the impactor engaged with the body of the impactor of FIG. 27.

As shown in FIG. 27C, the pin 1646 may be fixedly attached to the stop 1620 and slidably cooperable with to the body 1612.

Figure 28:
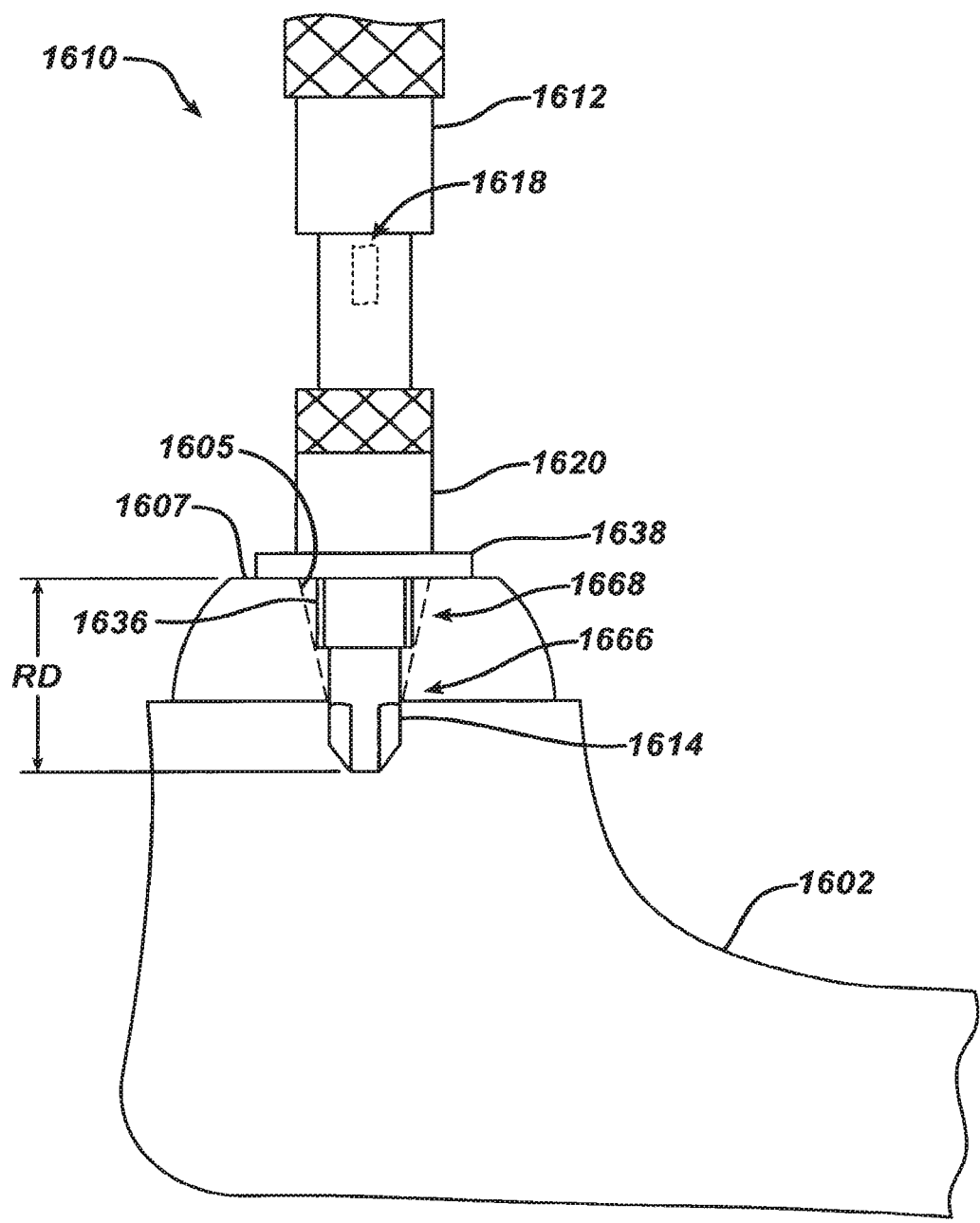
FIG. 28 is a partial plan view of the impactor of FIG. 26, partially in cross section, in position on the humerus and with the punch fully engaged into the humerus.

Referring to FIG. 28, the instrument 1610 is shown in second position 1666. The second position 1666 is permissible when the J-channel 1640 is rotated to permit the pin 1646 to advance to third position 1664, which is shown in FIG. 27B.

As shown in FIG. 28, the punch 1640 is spaced a distance RD from planar face 1607 forming the recess depth of the recess 1668 formed in the humerus 1602. The collar 1638 of the stop 1620 rests against planar face 1607 of the long bone 1602. The pilot 1636 matingly fits in pilot hole 1605 of the long bone 1602.

Figure 29:
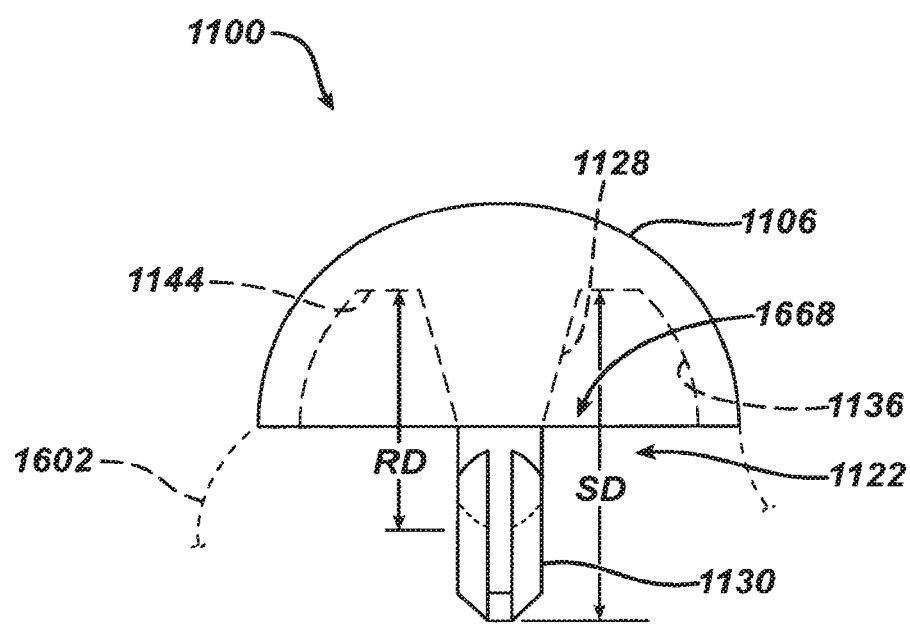
FIG. 29 is a plan view, partially in cross section, of an implant for use with the impactor of FIG. 26.

Referring now to FIG. 29, an implant 1100 is shown engaged in the long bone or humerus 1602. The implant 1100 includes an outer convex articulating surface 1106 and an opposed concave surface portion 1136. The implant 1106 further includes a stem 1122, which is fitted into the recess 1668 formed by the punch 1614 of the instrument 1610 of the present invention.

The stem 1122 includes a positioning portion 1128 and a securing portion 1130 extending from the positioning portion 1128. The securing portion 1130 and the positioning 1128 form a stem depth SD, which is greater than the recess depth RD of the recess 1668 so that the implant 1100 may be securely driven into an undisturbed portion of the long bone or humerus 1602 for a secure stem fit there to.

Figure 30:
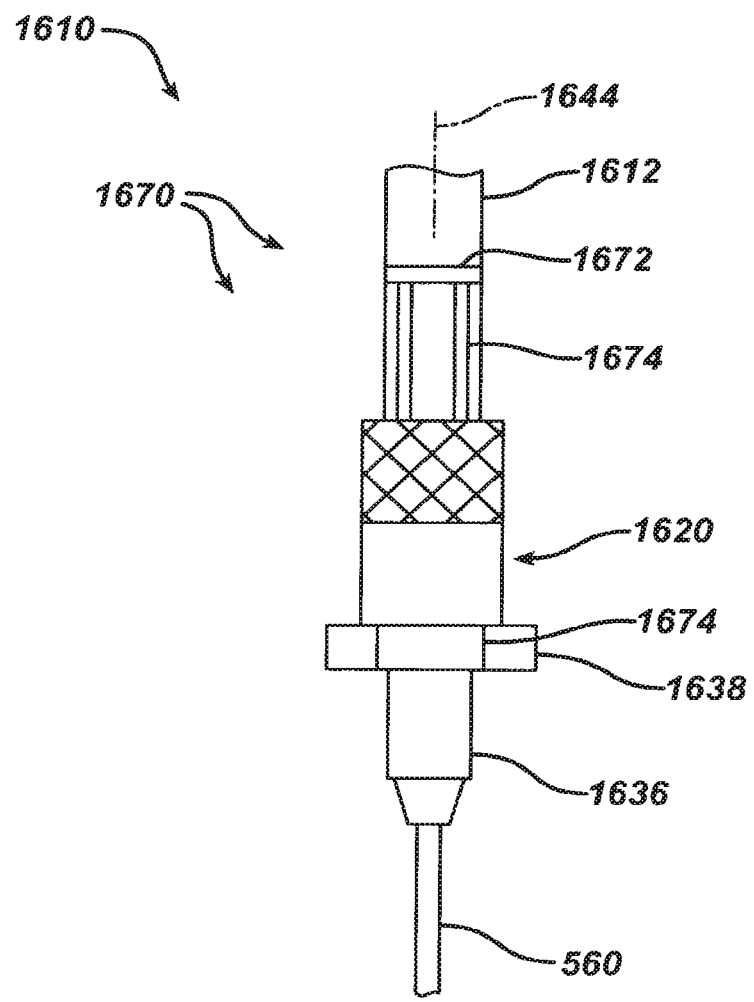
FIG. 30 is a partial plan view of the impactor of FIG. 26 showing the indicia in greater detail.

Referring now to FIG. 30, the instrument 1610 is shown with the indicia in the form of, for example, laser markings 1670. The markings 1670 may be applied to the instrument 1620 by any suitable method such as by painting, machining, or etching, such as by laser etching. As shown in FIG. 30, the markings 1670 include both a transverse position mark 1672 to and longitudinal position marks 1674. The transverse position mark 15 used to indicate when the stop 1620 is fully advanced outwardly for the formation of a complete recess or in the second position 1666 as shown in FIG. 28.

The longitudinal position marks 1674 are utilized to align the fin 1676 (see FIG. 31) in the proper position on the humerus. If, for example, there are four spaced apart separate fins 1676 then, as shown in FIG. 30, there are four similarly spaced-apart longitudinal marks 1674 extending parallel to the longitudinal axis 1644 of the body 1612. The longitudinal position marks 1674 may be spaced apart by 90 degrees and may extend the full length of the axis 1644 on the collar 1638 of the stop 1620. The longitudinal position marks 1674 may be positioned on the body 1612 or on collar 1638 or on both. For example, the stop 1620 moves along the body 1612.

Figure 31:
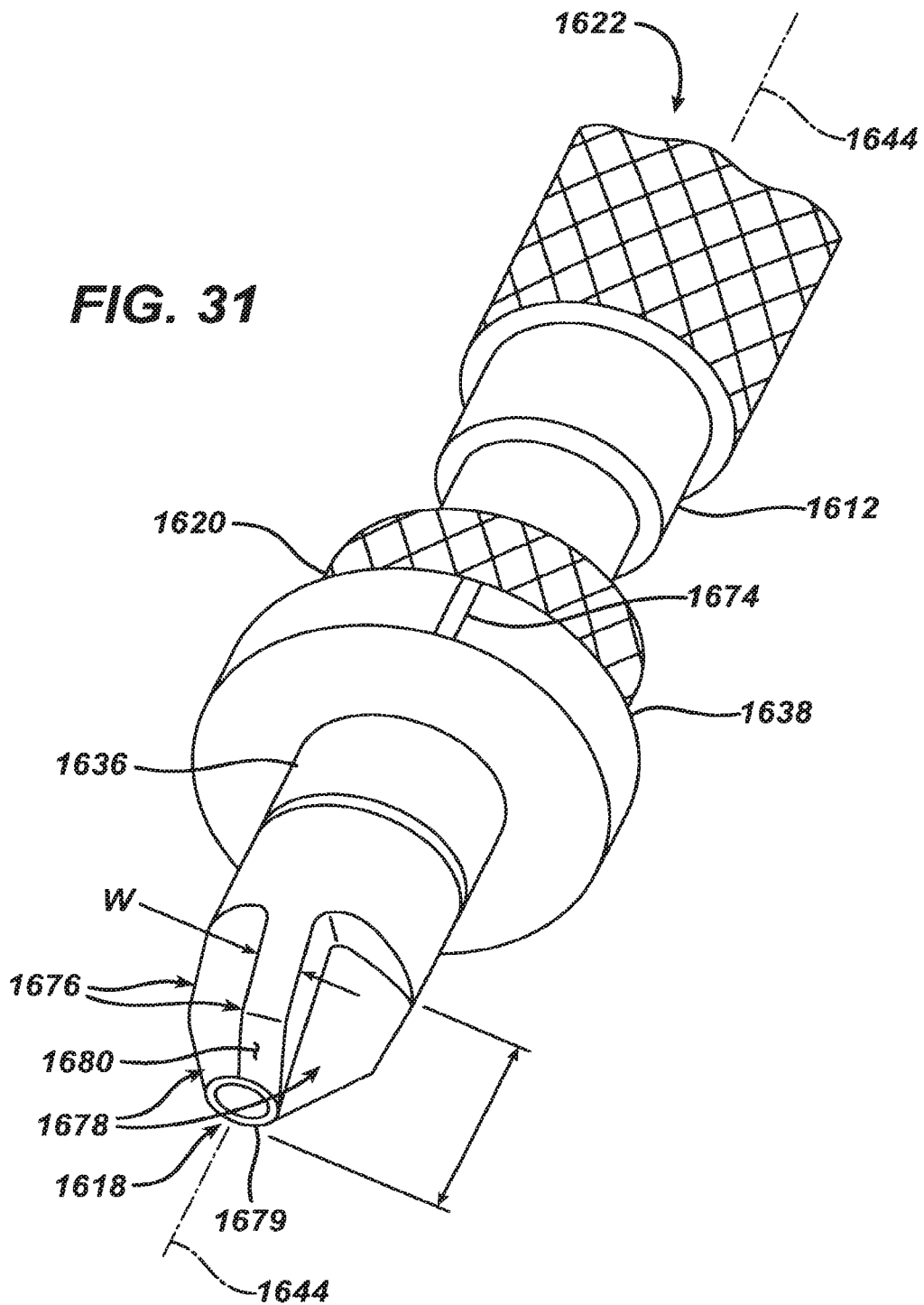
FIG. 31 is a partial perspective view of the impactor of FIG. 26 showing the indicia on the collar in greater detail.

Referring now to FIG. 31, the stop 1620 of the instrument 1610 is shown in greater detail. As shown in FIG. 31, the instrument 1610 may include a plurality of rotational stabilizing features in the form of, for example, fins 1676. It should be appreciated that a solitary fin 1676 or any number, for example, 2, 3, 4, 5, or more fins maybe utilized.

For simplicity and optimum fixation the fins 1676 may be equally spaced. The fins 1676 define voids 1678 spaced between the adjoining fins 1676. The fins 1676 may have any suitable shape and may have a uniform width along the axis 1644 and may extend the length L from end 1679 of the body 1612. The fins 1676 may define a chamfer 1680 located on and extending from end 1679 of the body 1612.

Figure 32:
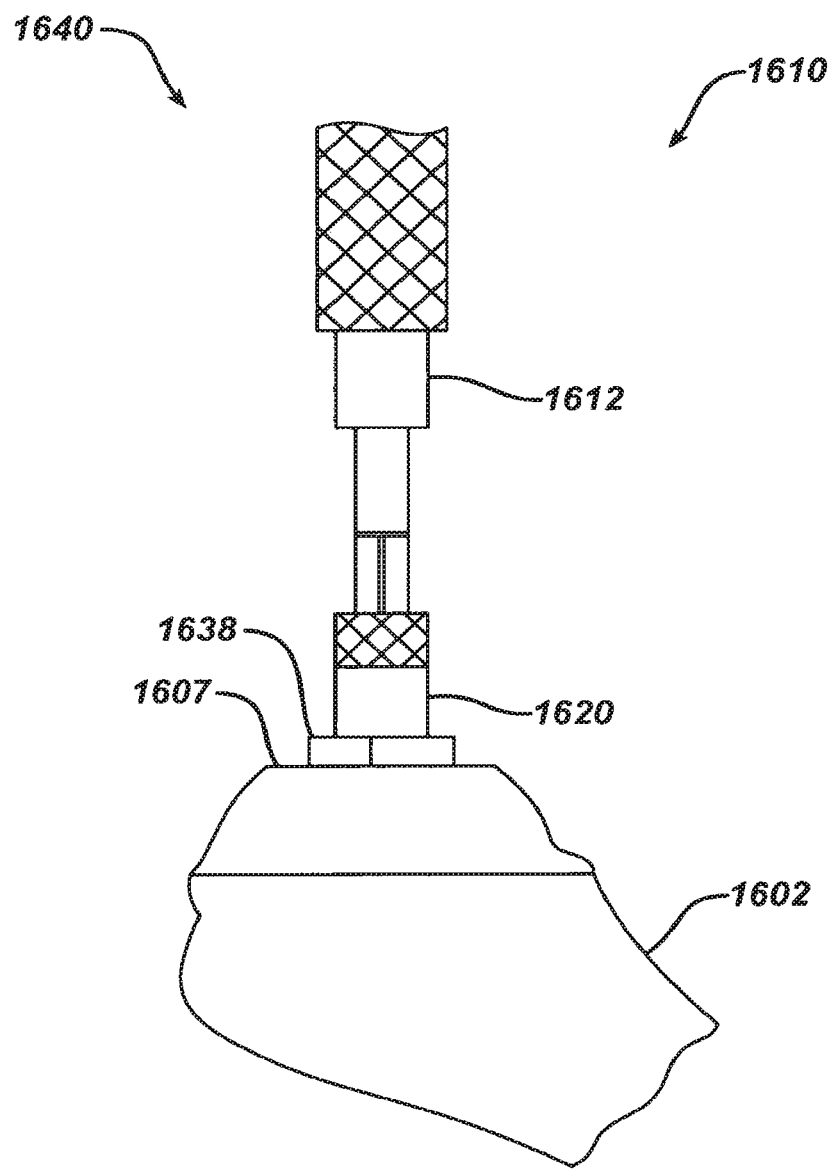
FIG. 32 is a partial plan view, partially in cross section of the impactor of FIG. 26 in position on the humerus.

Referring now to FIG. 32, the instrument 1610 is shown in first position 1640 in engagement with the long bone 1602. The collar 1638 of the stop 1620 of the instrument 1610 is seated against planar face 1607 of the long bone 1602.

Figure 33:
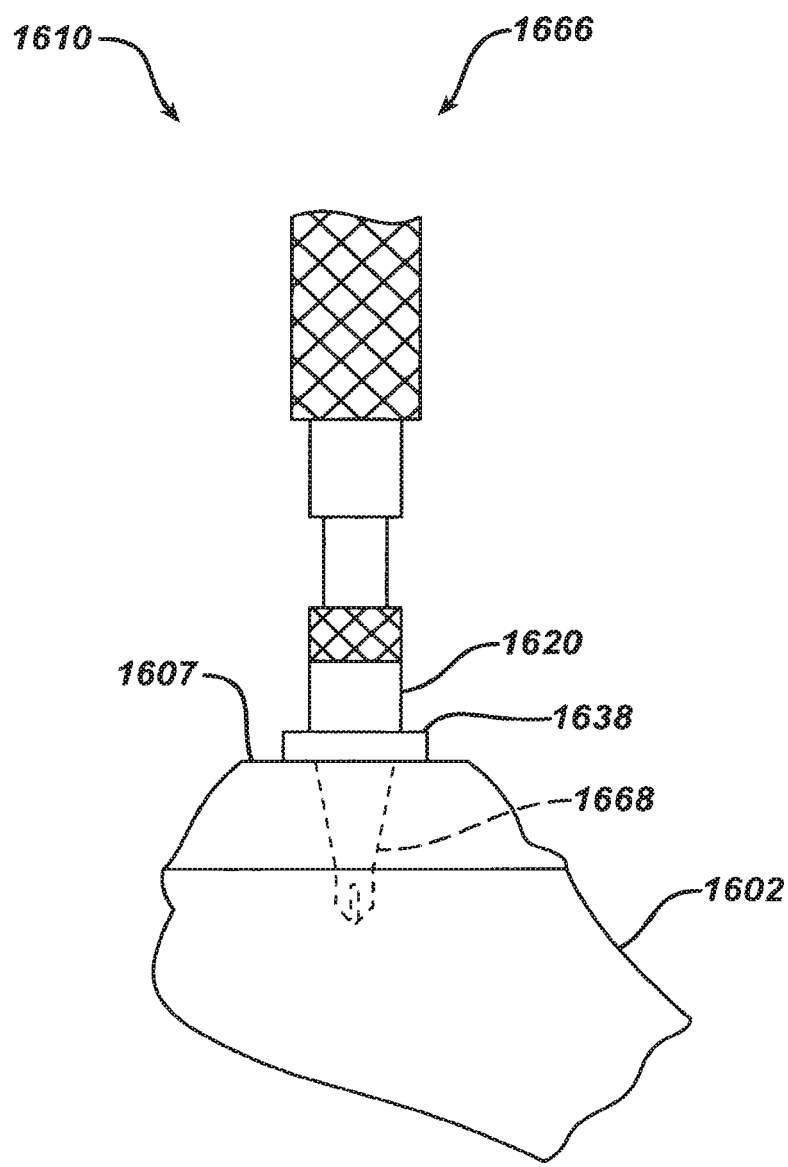
FIG. 33 is a partial plan view, partially in cross section of the impactor of FIG. 26 in position on the humerus with the punch fully engaged into the humerus.

Referring now to FIG. 33, the instrument 1610 is shown in the second position 1666 with the recess 1668 formed by the instrument 1610 in the long bone. The collar 1638 of the stop 1620 is positioned against the planar face 1607 of the long bone 1602.

Figure 34:
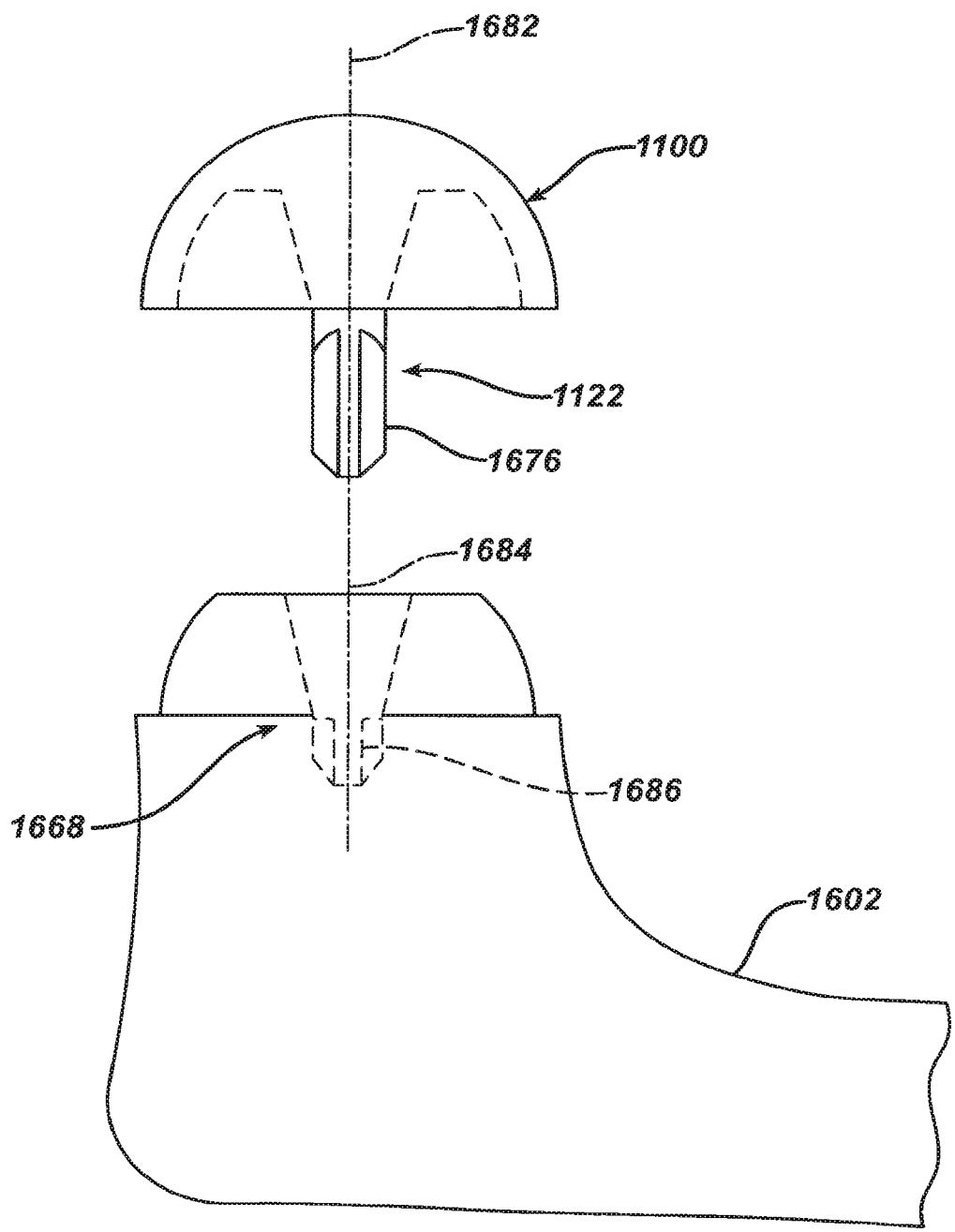
FIG. 34 is a plan view, partially in cross section of the implant of FIG. 29 in position spaced above the humerus.
Figure 35:
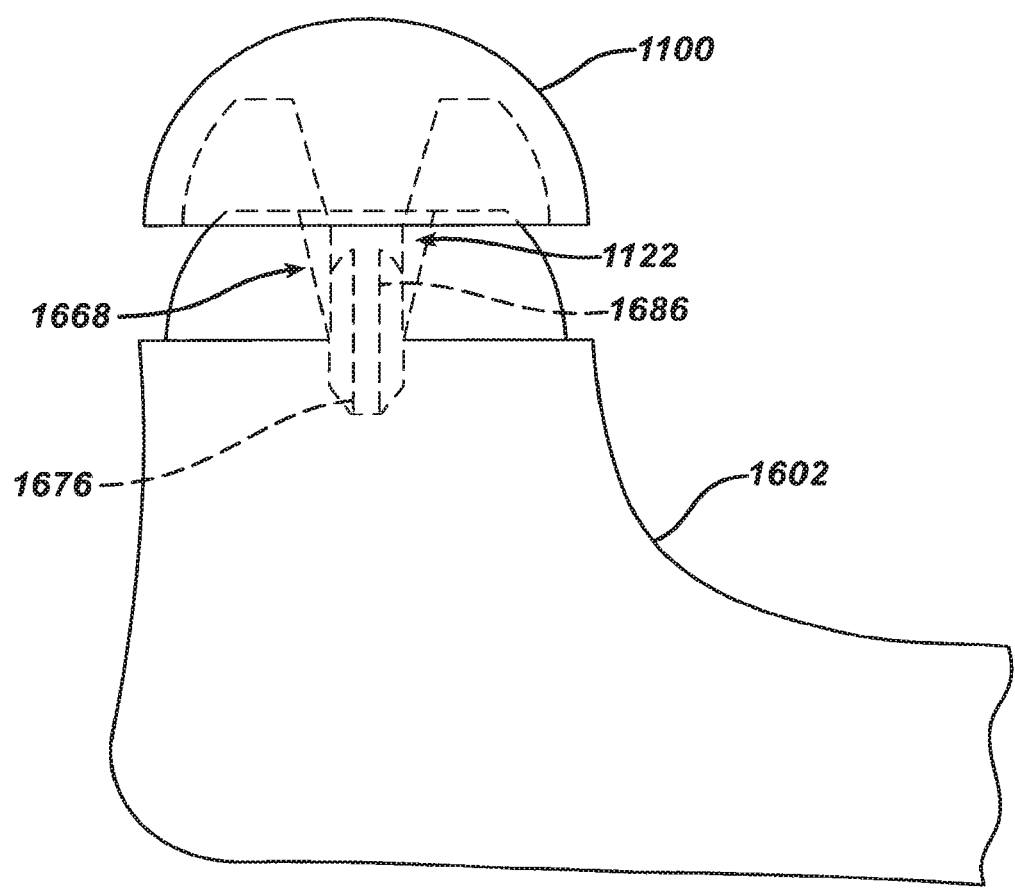
FIG. 35 is a plan view, partially in cross section of the implant of FIG. 29 in position directly above the humerus.
Figure 36:
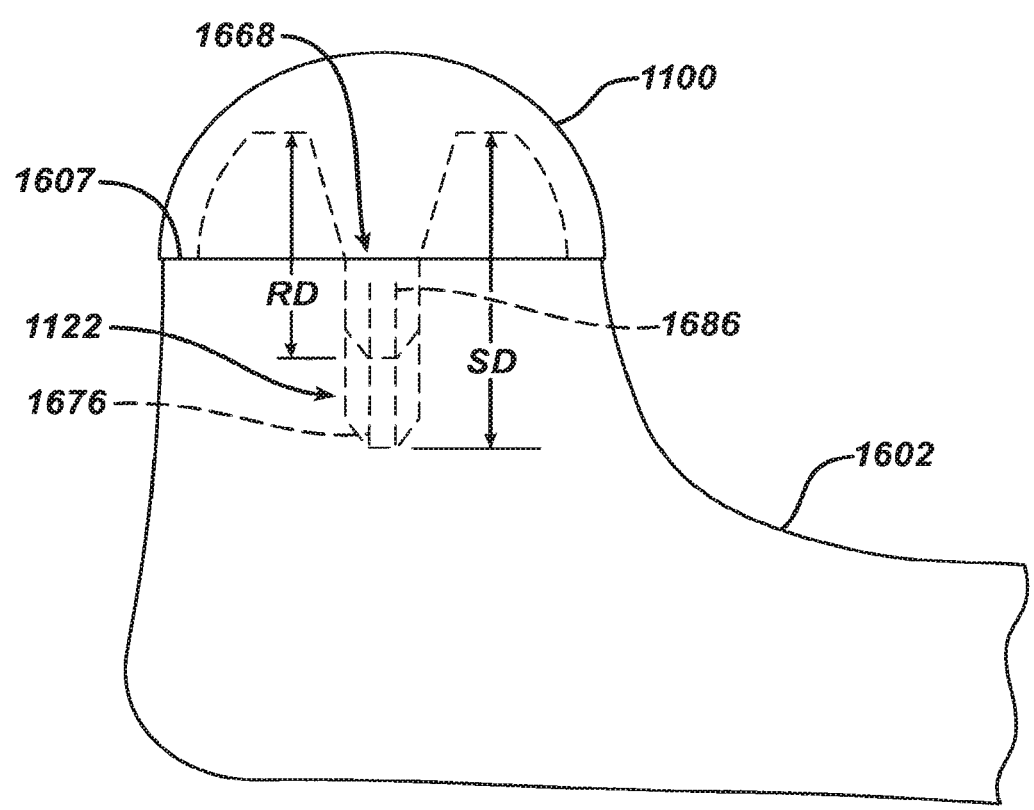
FIG. 36 is a plan view, partially in cross section of the implant of FIG. 29 in position on the humerus.

Referring now to FIGS. 34, 35, and 36 implant 1100 is shown for engagement with the long bone or humerus 1602. Referring now to FIG. 34, the implant 1100 is shown with implant 1100 in position over the humerus 1602. Implant centerline 1682 of implant 1100 is in alignment with recess centerline 1684 of the recess 1668 of the humerus 1602. Visually the fins 1676 of the stem 1122 of the implant 1100 are in visual alignment with fin grooves 1686 formed in the recess 1668 of the humerus 1602.

Referring now to FIG. 35, the implant 1100 is shown in actual engagement with the humerus 1602. The stem 1122 of the implant 1100 is fitted into the recess or depression 1668 of the long bone 1602. It should be appreciated that the fins 1676 of the stem 1122 are preferably aligned with the fin grooves 1686 formed in the recess 1668.

Referring now to FIG. 36, the implant 1100 is shown fully seated against the planar surface 1607 of the long bone 1602. The implant 1602 may be seated by any suitable method for example and for simplicity, by use of the mallet or hammer with a soft or plastic contact surface.

As shown in FIG. 36, the stem 1122 of the implant 1100 is shown fully engaged in humerus 1602. The fin grooves 1686 of the recess 1668 are in radial alignment with the fins 1676 of the stem 1122. It should be appreciated that the stem 1122 has a stem depth SD, which is greater than the recess depth RD. Such a difference in the depths permits the stem 1122 of the implant 1100 to engage an unpunched portion of the long bone 1602 for improved attachment of the implant 1100 to the bone 1602.

Figure 37:
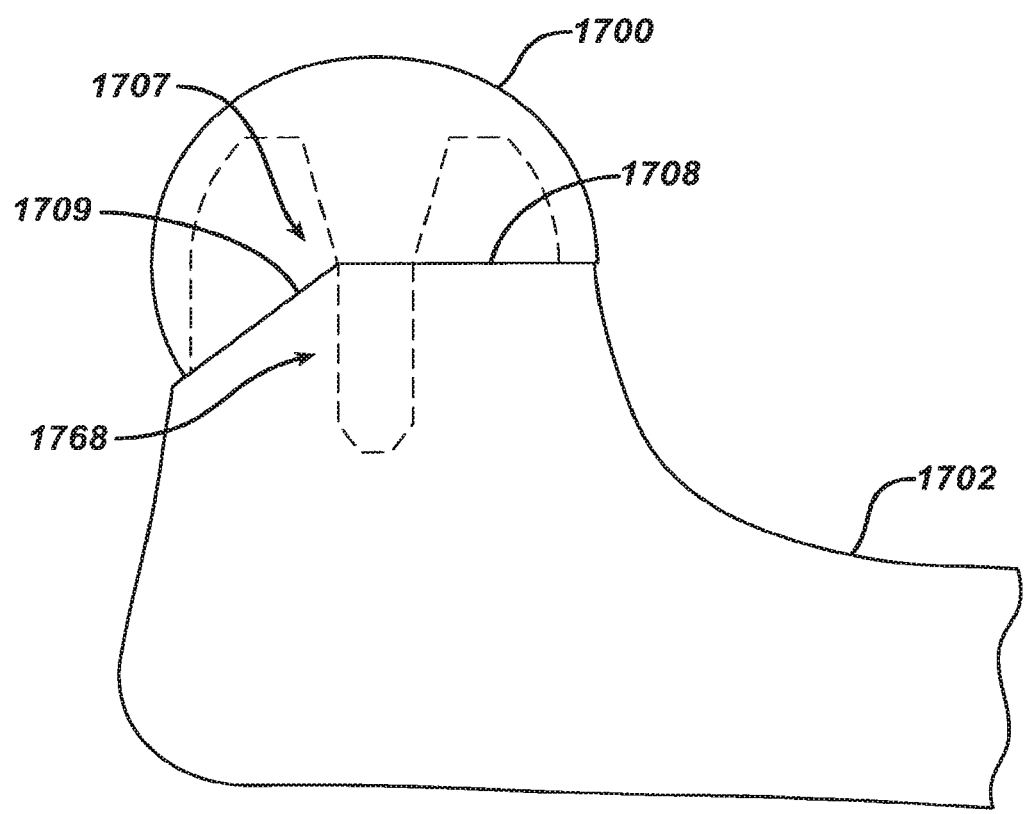
FIG. 37 is a plan view, partially in cross section of another embodiment of the present invention in the form of an extended articulation implant in position on the humerus.

The instrument 1610 may be utilized to prepare a recess stem for any suitable surface replacement prosthesis. For example and is shown in FIG. 37, the instrument of the present invention, may form recess 1768 in long bone 1702. Recess 1768 may be positioned against surface 1702 that includes a planar portion 1708 as well as an angled portion 1709. The face 1707 may be utilized to accept for example, an extended articulation implant 1700 for use, for example, for shoulders with rotator cuff tear anthrophy.

Figure 38:
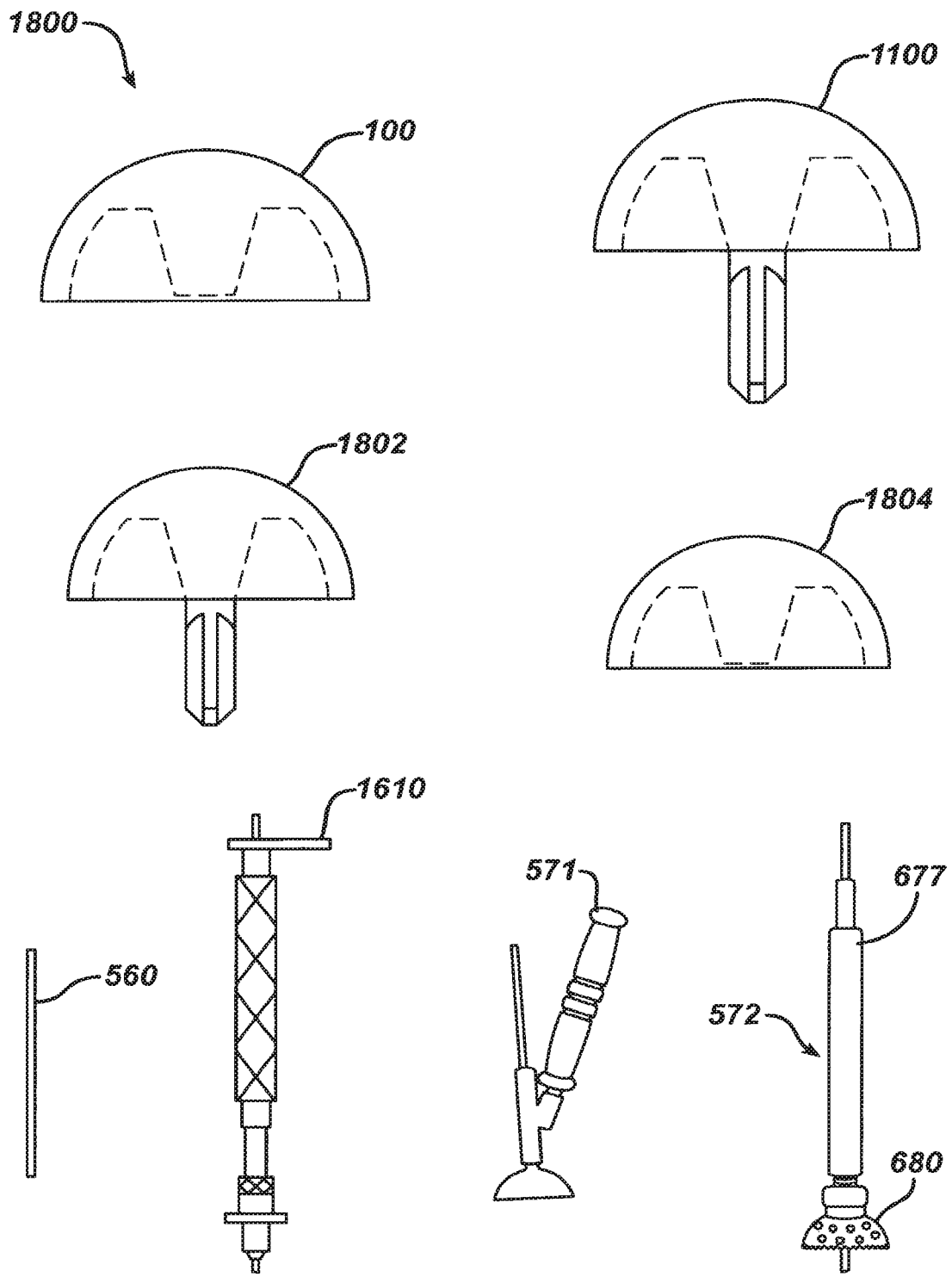
FIG. 38 is a plan view, partially in cross section, of another embodiment of the present invention in the form of a kit.

Referring now to FIG. 38, the kit 1800 is shown. The kit 1800 may include an instrument 1610 as well as first implant 1100. The kit 1800 may also include a first trial 100.

The kit 1800 may include additional implants that may be available for the surgeon in case the first implant is not found to be the proper size during surgery. For example, the kit 1800 may include a second implant 1802. To assist the patient in forming the trial reduction or motion of the joint to verify the proper selection of, the implant, the kit 1800 may include a second trial 1804. It should be appreciated that the first implant 1100 may correspond to the first trial 100 while the second implant 1802 may correspond to the second trial 1804.

The surgeon may implant the first trial and prepare a trial reduction. If the first trial 100 is found to be proper, then the first implant 1100 will be implanted. If the first trial 100 is found to be sub-optimal another trial, for example, the second trial 1804 may be implanted. If the second trial 1804 after the trial reduction is found to be optimum, then the second implant 1802 would be utilized.

It should be appreciated that additional implants, for example, a third implant or a third trial (not shown) may be included in the kit 1800.

Further the kit 1800 may include other instruments in addition to the instrument 1610. For example, the kit 1800 may include a guide pin alignment tool 571 for aligning a guide pin or a guide wire 560. The kit 1800 may also include the guide wire 560. Further the kit 1800 may include an instrument for preparing long bone. For example, it may include a tool assembly 572 including a cutting tool 680 and a tool holder 677. It should be appreciated additional implants, instruments, and trials may be included in the kit 1800.

Figure 39:
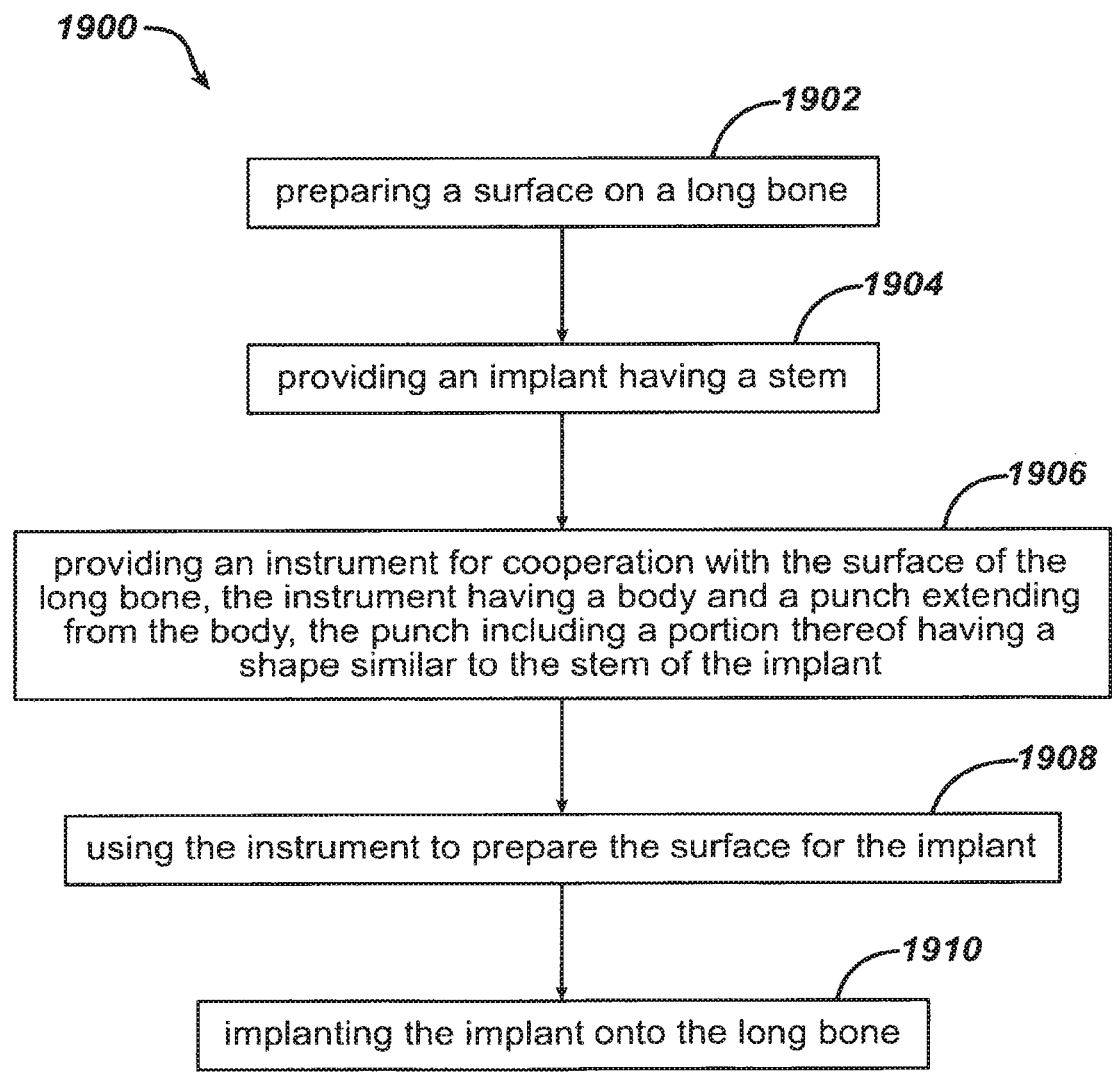
FIG. 39 is a process flow chart of a method of performing arthroplasty surgery according to another embodiment of the present invention.

Referring now to FIG. 39, another embodiment of the present invention is shown as method 1900. Method 1900 includes the first step 1902 of preparing a surface on a long bone. The surgical procedure or method 1900 may also include a second step 1904 of providing an implant having a stem.

The method 1900 may further step for providing an instrument for cooperation with the surface of the long bone. The instrument may have a body and a punch extending from the body. The punch may include a portion of the punch having a shape similar to the stem of the implant.

The method 1900 may further include a fourth step 1908 of using the instrument to prepare the surface for implant. The method further includes a fifth step 1910 of implanting the implant into the long bone.

Although the present invention and its advantages have been described in detail, it should be understood that various changes, substitutions, and alterations can be made therein without departing from the spirit and scope of the present invention as defined by the appended claims.

We claim:

1. A method for providing joint arthroplasty comprising:
   preparing a flat surface on a long bone;
   providing an implant having a stem with a shape;
   providing an instrument having a body and a punch extending from the body, the punch including a portion thereof having a shape similar to the stem of the implant;
   supporting a stop with the flat surface;
   rotating the stop with respect to the surface of the long bone based upon an indicia on one of the body and the stop so as to position the punch rotationally with respect to the surface to a first orientation with the body at least partially inserted into the stop;
   using the instrument to form a cavity in the long bone with the punch at the first rotational orientation by moving the body axially with respect to the stop, the cavity having a shape similar to the stem of the implant; and
   implanting the stem of the implant into the cavity.

2. The method of claim 1, wherein rotating the stop comprises:
   rotating the stop prior to using the instrument to form a cavity in the long bone and after supporting the stop with the flat surface.

3. The method of claim 1, wherein rotating the stop comprises:
   rotating the stop with respect to the body with the body at least partially inserted into the stop.

4. The method of claim 1, wherein the stop includes a central opening and a pin and the body includes a slot, the method further comprising:
   moving the slot with respect to the pin while using the instrument to form the cavity.

5. The method of claim 4, further comprising:
   moving the slot laterally with respect to the pin within a first slot portion of the slot prior to using the instrument to form the cavity, wherein moving the slot with respect to the pin while using the instrument to form the cavity comprises:
   moving the slot vertically with respect to the pin within a second slot portion of the slot while using the instrument to form the cavity.

6. The method of claim 4, wherein using the instrument to form the cavity further comprises:
   limiting movement of the punch into the long bone by impingement of the pin against an end portion of the slot.

7. The method of claim 4, further comprising:
   forming a pilot hole in the long bone, the pilot hole extending downwardly from the flat surface; and
   inserting a pilot extending downwardly from a collar of the stop into the formed pilot hole, wherein positioning the stop on the flat surface comprises:
   positioning the collar on the flat surface as the pilot is inserted into the pilot hole.

8. The method of claim 7, wherein rotating the stop comprises:
   rotating the stop prior to using the instrument to form a cavity in the long bone and after supporting the stop with the flat surface.

9. The method of claim 7, wherein rotating the stop comprises:
   rotating the stop with respect to the body with the body at least partially inserted into the stop.

10. The method of claim 1, further comprising:
    forming a pilot hole in the long bone, the pilot hole extending downwardly from the flat surface; and
    inserting a pilot extending downwardly from a collar of the stop into the formed pilot hole, wherein positioning the stop on the flat surface comprises:
    positioning the collar on the flat surface as the pilot is inserted into the pilot hole.

11. The method of claim 10, wherein rotating the stop comprises:
    rotating the stop prior to using the instrument to form a cavity in the long bone and after supporting the stop with the flat surface.

12. The method of claim 10, wherein rotating the stop comprises:
    rotating the stop with respect to the body with the body at least partially inserted into the stop.

13. A method for providing joint arthroplasty comprising:
    preparing a flat surface on a long bone;
    providing an implant having a stem with a shape;
    providing an instrument having a body and a punch extending from the body, the punch including a portion thereof having a shape similar to the stem of the implant;
    positioning a stop on the flat surface, wherein the stop includes a central opening and a pin and the body includes a slot;
    using the instrument to form a cavity in the long bone with the punch, the cavity having a shape similar to the stem of the implant;
    moving the slot with respect to the pin while using the instrument to form the cavity; and
    implanting the stem of the implant into the cavity.

14. The method of claim 13, further comprising:
    moving the slot laterally with respect to the pin within a first slot portion of the slot prior to using the instrument to form the cavity, wherein moving the slot with respect to the pin while using the instrument to form the cavity comprises:
    moving the slot vertically with respect to the pin within a second slot portion of the slot while using the instrument to form the cavity.

15. The method of claim 13, wherein using the instrument to form the cavity further comprises:
    limiting movement of the punch into the long bone by impingement of the pin against an end portion of the slot.

16. The method of claim 13, further comprising:
    forming a pilot hole in the long bone, the pilot hole extending downwardly from the flat surface; and
    inserting a pilot extending downwardly from a collar of the stop into the formed pilot hole, wherein positioning the stop on the flat surface comprises:
    positioning the collar on the flat surface as the pilot is inserted into the pilot hole.

17. The method of claim 13, further comprising:
    rotating the stop with respect to the surface of the long bone based upon an indicia on one of the body and the stop so as to position the punch rotationally with respect to the surface to a first orientation prior to using the instrument to form the cavity in the long bone.

18. The method of claim 17, wherein rotating the stop comprises:
rotating the stop after inserting a pilot of the stop into a pilot hole formed in the long bone.

* * * * *